(12) United States Patent
Ning et al.

(10) Patent No.: US 7,196,190 B2
(45) Date of Patent: *Mar. 27, 2007

(54) METHODS AND COMPOSITIONS FOR SCREENING FOR ANGIOGENESIS MODULATING COMPOUNDS

(75) Inventors: Zhang Ning, Alameda, CA (US); Pamela Reilly Contag, San Jose, CA (US); Anthony F. Purchio, Alameda, CA (US)

(73) Assignee: Xenogen Corporation, Alameda, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/738,968

(22) Filed: Dec. 15, 2000

(65) Prior Publication Data

US 2001/0037016 A1    Nov. 1, 2001

Related U.S. Application Data

(63) Continuation-in-part of application No. 09/465,978, filed on Dec. 16, 1999, now Pat. No. 6,867,348.

(51) Int. Cl.
*C07H 21/04* (2006.01)
*C12N 15/00* (2006.01)
*C12N 15/63* (2006.01)
*C12N 5/00* (2006.01)
*A01K 67/027* (2006.01)

(52) U.S. Cl. .................. 536/24.1; 435/320.1; 435/325

(58) Field of Classification Search ............. 435/320.1, 435/325, 455; 536/24.1
See application file for complete search history.

(56) References Cited

U.S. PATENT DOCUMENTS

| 5,650,135 | A | 7/1997 | Contag et al. |
| 6,020,121 | A | 2/2000 | Bao et al. |
| 6,217,847 | B1 | 4/2001 | Contag et al. |

FOREIGN PATENT DOCUMENTS

| WO | WO 94/11499 | 5/1994 |
| WO | WO 96/40979 | 12/1996 |
| WO | WO 9700957 A | 1/1997 |
| WO | WO 97/11690 A2 | 4/1997 |
| WO | WO 97/11690 A3 | 4/1997 |
| WO | WO 97/18841 | 5/1997 |
| WO | WO 97/40381 | 10/1997 |
| WO | WO 98/28971 | 7/1998 |
| WO | WO 98/30715 | 7/1998 |
| WO | WO 98/55638 A | 12/1998 |
| WO | WO 00/08726 | 2/2000 |
| WO | WO 00/36106 | 6/2000 |
| WO | WO 00/54581 A2 | 9/2000 |
| WO | WO 00/54581 A3 | 9/2000 |
| WO | WO 01/18195 | 3/2001 |
| WO | WO 01/18225 | 3/2001 |
| WO | WO 01/37195 | 5/2001 |

OTHER PUBLICATIONS

Shima et al. The mouse gene for vascular endothelial growth factor pp. 3877-3883 vol. 271, No. 7 1996.*

Aiello et al., "Suppression of Retinal Neovascularization Iin Vivo by Inhibition of Vascular Endothelial Growth Factor (VEGF) Using Soluble VEGF-Receptor Chimeric Proteins," *Proc. Natl. Acad. Sci. U.S.A.* 92:10457-10461 (1995).

Asahara et al., "Bone Marrow Origin of Endothelial Progenitor Cells Responsible for Postnatal Vasculogenesis in Physiological and Pathological Neovascularization," *Circ. Res.* 85:221-228 (1999).

Bais et al., "G-Protein-Coupled Receptor of Kaposi's Sarcoma-Associated Herpes Virus is a Viral Oncogene and Anglogenesis Activator," *Nature* 391:86-89 (1998).

Benjamin et al., "Conditional Switching of Vascular Endothelial Growth Factor (VEGF) Expression in Tumors: Induction of Endothelial Cell Shedding and Regression of Hemangioblastoma-Like Vessels by VEGF Withdrawal," *Proc. Natl. Acad. Sci. U.S.A.* 94:8761-8766 (1997).

Berse, B., "Vascular Permeability Factor (Vascular Endothelial Growth Factor) Gene is Expressed Differentially in Normal Tissues, Macrophases, and Tumors," *Molecular Biology of the Cell* 3:211-220 (1992).

Contag et al., "Visualizing Gene Expression Living Mammals Using a Bioluminescent Reporter," *Photochemistry and Photobiology* 66(4):523-531 (1997).

Disalvo et al., "Purification and Characterization of Naturally Occurring Vascular Endothelial Growth Factor-Placenta Growth Factor Heterodimer," *The Journal of Biological Chemistry* 270(13):7717-7723 (1995).

Dumont, et al., "Dominant-Negative and Targeted Null Mutations in the Endothelial Receptor Tyrosine Kinase, *Tek*, Reveal a Critical Role in Vasculogenesis of the Embryo," *Genes & Development* 8:1897-1909 (1994).

(Continued)

*Primary Examiner*—Quang Nguyen
(74) *Attorney, Agent, or Firm*—Robins & Pasternak LLP

(57) ABSTRACT

The present invention relates to novel transcription control elements, including promoters, derived from angiogenesis-related genes, particularly the mouse VEGF gene, the mouse VEGFR-2 receptor gene, and the mouse Tie2 gene. Also disclosed are isolated polynucleotides comprising such promoters, as well as nucleic acid constructs comprising such promoters operatively linked to genes encoding a gene product, such as, a reporter, a protein, polypeptide, hormone, ribozyme, or antisense RNA, and to recombinant cells and transgenic animals comprising such nucleic acid constructs. The present invention further relates to screening methods using those recombinant cells and transgenic animals, particularly methods of screening for therapeutic compounds that modulate tumorigenesis and angiogenesis.

12 Claims, 28 Drawing Sheets

OTHER PUBLICATIONS

Dvorak et al., "Distribution of Vascular Permeability Factor (Vascular Endothelial Growth Factor) in Tumors: Concentration in Tumor Blood Vessels," *J. Exp. Med.* 174:1275-1278 (1991).

Ferrara et al., "The Biology of Vascular Endothelial Growht Factor," *Endocr. Rev.* 18:(1):4-25 (1997).

Ferrara et al., "Heterozygous Embryonic Lethality Inducted by Targeted Inactivation of the VEGF Gene," *Nature* 380:439-442 (1996).

Fong et al., "SU5416 Is a Potent and Selective Inhibitor of the Vascular Endothelial Growth Factor Receptor (Flk-1/KDR) That Inhibits Tyrosine Kinase Catalysis, Tumor Vascularization, and Growth of Multiple Tumor Types," *Cancer Research* 59:99-106 (1999).

Forsythe et al., "Activation of Vascular Endothelial Growth Factor Gene Transcription by Hypoxia-Inducible Factor 1," *Molecular and Cellular Biology* 16(9):4604-4613 (1996).

Fukumura et al., "Tumor Induction of VEGF Promoter Activity in Stormal Cells," *Cell* 94:715-725 (1998).

Hanahan, D., "Signaling Vascular Morphogenesis and Maintenance," *Science* 277:48-50 (1997).

Ikeda et al., "Hypoxia-Induced Transcriptional Activation and Increased mRNA Stability of Vascular Endothelial Growth Factor in C6 Glioma Cells," *The Journal of Biological Chemistry* 270(34):19761-19765 (1995).

Jain, R.K., "Endothelial Cell Death, Augiogenesis, and Microvascular Function After Casteration in an Andgrogen-Dependent Tumor: Role of Vascular Endothelial Groth Factor," *Proc. Natl. Acad. Sci. U.S.A.* 95:10820-10825 (1998).

Jeltsch et al., "Hyperplasia of Lymphatic Vessels in VEGF-C Transgenic Mice," *Science* 276:1423-1425 (1997).

Kaipainen, et al., "Enhanced Expression of the Tie Receptor Tyrosine Kinase Messenger RNA in the Vascular Endothelium of Metastatic Melanomas," *Cancer Research* 54:6571-6577 (1994).

Kappel et al., "Identification of Vascular Endothelial Growth Factor (VEGF) Receptor-2 *(Flk-1)* Promother/Enhancer Sequences Sufficient for Angioblast and Endothelial Cell-Specific Transcription in Transgenic Mice," *Blood* 93(12):4284-4292 (1999).

Kim et al., "Inhibition of Vascular Endothelial Growth Factor-Induced Angiogenesis Suppresses Tumour Growth *In Vivo,*" *Nature* 362:841-844 (1993).

Kitsukawa et al., "Overexpression of Membrane Protein, Neuropilin, in Chimeric Mice Causes Anomalies in the Cardiovascular System, Nervous System and Limbs," *Development* 121:4309-4318 (1995).

Larcher et al., "VEGF/VPF Overexpression in Skin of Transgenic Mice Induces Angiogenesis, Vascular Hyperpermeability and Accelerated Tumor Development," *Oncogene* 17:303-311 (1998).

Millauer, B., "High Affinity VEGF Binding and Developmental Expression Suggest Flk-1 as a Major Regulator of Vasculogenesis and Angiogenes," *Cell* 72:835-846 (1993).

Millauer, B., "Glioblastoma Growth Inhibited *In Vivo* by a Dominant-Negative Flk-1 Mutant," *Nature* 367:576-579 (1994).

Millauer, B., "Dominant-Negative Inhibition of Flk-1 Suppresses the Growth of Many Tumor Types *In Vivo,*" *Cancer Res.* 56:1615-1620 (1996).

Mukhopadhyay et al., "Wild-Type p53 and v-Src Exert Opposing Influences on Human Vascular Endothelial Growth Factor Gene Expression," *Cancer Res.* 15:6161-6165 (1995).

Mukhopadhyay et al., "Hypoxic Induction of Human Vascular Endothelial Growth Factor Expression Through c-Src Activation," *Nature* 375:577-581 (1995).

Oh et al., "VEGF and VEGF-C: Specific Induction of Angiogenesis and Lyphangiogenesis in the Differentiated Avian Chorioallantoic Membrane," *Developmental Biology* 188:96-109 (1997).

Okamoto et al., "Transgenic Mice With Increased Expression of Vascular Endothelial Growth Factor in the Retinal," *American Journal Pathology* 151:281-291 (1997).

Olofason et al., "Vascular Endothelial Growth Factor B, a Novel Growth Factor for Endothelial Cells," *Proc. Natl. Acad. Sci. U.S.A.* 93:2576-2581 (1996).

Patterson et al., "Cloning and Functional Analysis of the Promoter for KDR/flk-1, a Receptor for Vascular Endothelial Growth Factor," *The Journal of Biological Chemistry* 270(39):23111-23118 (1995).

Plate et al., "Vascular Endothelial Growth Factor is a Potential Tumour Angiogenesis Factor in Human Gliomas *In Vivo,*" *Nature* 359:845-848 (1992).

Plate et al., "Up-Regulation of Vascular Endothelial Growth Factor and Its Cognate Receptors in a Rat Glioma Model of Tumor Angiogenesis," *Cancer Research* 53:5822-5827 (1993).

Puri et al., "The Receptor Tyrosine Kinase TIE is Required for Integrity and Survival of Vascular Endothelial Cells," *EMBO Journal* 14(23):5884-5891 (1995).

Rönicke et al., "Characterization of the Endothelium-Specific Murine Vascular Endothelial Growth Factor Receptor-2 (Flk-1) Promoter," *Circulation Research* 79(2):277-285 (1996).

Shalaby et al., "Failure of Blood-Island Formation and Vasculogenesis in Flk-1-Deficient Mice," *Nature* 376:62-65 (1995).

Shweiki et al., "Vascular Endothelial Growth Factor Induced by Hypoxia may Mediate Hypoxia-Initiated Angiogenesis," *Nature* 359:843-845 (1992).

Shweiki et al., "Induction of Vascular Endothelial Growth Factor Expression by Hypoxia and by Glucose Deficiency in Multicell Spheroids: Implications for Tumor Angiogenesis," *Proc. Natl. Acad. Sci. U.S.A.* 92:768-772 (1995).

Siemeister et al., "An Antagonistic Vascular Endothelial Growth Factor (VEGF) Variant Inhibits VEGF-Stimulated Receptor Autophosphorylation and Proliferation of Human Endothelial Cells," *Proc. Natl. Acad. Sci. U.S.A.* 95:4625-4629 (1998).

Soker et al., "Neuropilin-1 is Expressed by Endothelial and Tumor Cells as an Isoform-Specific Receptor for Vascular Endothelial Growth Factor," *Cell* 92:735-745 (1998).

Soker et al., "Characterization of Novel Vascular Endothelial Growth Factor (VEGF) Receptors on Tumor Cells that Bind VEGF $_{165}$ Via Its Exon 7-Encoded Domain," *Journal of Biological Chemistry* 271:5761-5767 (1996).

Soker et al., "Inhibition of Vascular Endothelial Growth Factor (VEGF)-Induced Endothelial Cell Proliferation by a Peptide Corresponding to the Exon 7-Encoded Domain of VEGF $_{165}$," *Journal of Biological Chemistry* 272(50):31582-31588 (1997).

Stratmann A., "Cell Type-Specific Expression of Angiopoietin-1 and Angiopoietin-2 Suggests a Role in Glioblastoma Angiogenesis," *American Journal of Pathology* 153(5):1459-1466 (1998).

Suri et al., "Requisite Role of Angiopoietin-1, a Ligand for the TIE2 Receptor, During Embryonic Angiogenesis," *Cell* 87:1171-1180 (1996).

Takahashi et al., "Markedly Increased Amounts of Messenger RNAs for Vascular Endothelial Growth Factor and Placenta Growth Factor in Renal Cell Carcinoma Associated with Angiogenesis," *Cancer Res.* 54:4233-4237 (1994).

Terman et al., "Identification of a New Endothelial Cell Growth Factor Recptor Tyrosine Kinase," *Oncogene* 6(9):1677-1683 (1991).

Tischer et al., "The Human Gene for Vascular Endothelial Growth Factor," *Journal of Biological Chemistry*: 266 (18):11947-11954 (1991).

Waltenberger, J., "Different Signal Transduction Properties of KDR and Flt1, Two Receptors for Vascular Endothelial Growth Factor," *Journal of Biological Chemistry* 269(43):26988-26995 (1994).

Yoshiji et al., "Vascular Endothelial Growth Factor is Essential for Initial but not Continued *in Vivo* Growth of Human Breast Carcinoma Cells," *Center Research* 57:3924-3928 (1997).

Yuan et al., "Time-Dependent Vascular Regression and Permeability Changes in Established Human Tumor Xenografts Induced by an Anti-Vascular Endothelial-Growth Factor/Vascular Permeability Factor Antibody," *Proc. Natl. Acad. Sci. U.S.A.* 93:14765-14770 (1996).

\* cited by examiner

| VEGF | VEGFR2 | Tie2 |
|---|---|---|
| Screening primers | Screening primers | Screening primers |
| Primers: VF1-VR1A<br>Product size: 0.69Kb | Primers: KF1-KR1<br>Product size: 0.45Kb | Primers: TF3-TR1<br>Product size: 0.45Kb |
| PCR program | PCR program | PCR program |
| Hot start | Hot start | Hot start |
| 94°C 40 sec<br>65°C 1 min 30 sec<br>72°C 1 min 30 sec | 94°C 40 sec<br>58°C 1 min 30 sec<br>72°C 1 min 30 sec | 94°C 40 sec<br>58°C 1 min 30 sec<br>72°C 1 min 30 sec |
| 40 cycles | 40 cycles | 40 cycles |
| Confirmation primers | Confirmation primers | Confirmation primers |
| Primers: VF2-VR2<br>Product size: 0.98Kb | Primers: KF2-KR2<br>Product size: 0.58Kb | Primers: TF2-TR1<br>Product size: 0.47Kb |
| PCR program | PCR program | PCR program |
| Hot start | Hot start | Hot start |
| 94°C 40 sec<br>65°C 1 min 30 sec<br>72°C 1 min 30 sec | 94°C 40 sec<br>65°C 1 min 30 sec<br>72°C 1 min 30 sec | 94°C 40 sec<br>58°C 1 min 30 sec<br>72°C 1 min 30 sec |
| 40 cycles | 40 cycles | 40 cycles |

*FIG. 1*

```
attctggggt tacaagcatg tggtcccttc ccatcccctt cccttctttc acctaggtgt 60
ggagtatatc tcttctccca gccctccctg actctagcca gatcatattg gcttgggaaa 120
tgaaccagat aagcacacgt acatcaactc ttacacctct ctacaaccct ggcaggaggc 180
aacaacactt tccatttcac agatgagaag actgaggctc acagctccgg aaatagtgaa 240
ccagatttgt gctccgtctg ccatgttttc ccattcctcg gtatgggttg ggtgggggtg 300
tggggtgtag cagaagccaa ggctcttcac agtgagggat caccaaccag tgacttcaag 360
gaagatgagg ctagttggtt atgcgtatga ctaattctag taatcccact acttgaaaat 420
ttgaggcagg aggattatga attccaagcc agcctgggat acatagtaag accaaaagat 480
gaagataaaa cagaaacaag ctgaaactaa aatgactgag gaggggttag aagagggagt 540
tggagtttcc tgtcttctgg gctgaaggtg tgtctcgcct ccattaaccg gtgctaggcc 600
ccggatgtca ccatggcatt cctgctagat ttttttggtg ttaaacattg ctctcttcaa 660
gagtcataag gacacaggcc acccgaagac gtgacatttg gtatcaagga acagtctcag 720
ctgtcactgt ctctagtgac tcagagctag gaatcttgc ctagaagtgg agggccagca 780
gcaggactgg tgaactggtg ctgaccaagg tcacactgcc tgtggccttc tcagctctcc 840
tggaggcagg gacagactag agaaagtgtt atcctgcttt gtgctctggt ctagccaact 900
ggccctgggc ttatcccagg ttgctgctta gggcaaacga tggccccagc actcagtata 960
tgactagacc tacctctact gtctggatgg tttttttaa aacactctct ggggacgtat 1020
tacttccttc ctggtagggg actgccaaga aagcagcgtg gaacttaccc ctgacagaac 1080
agtattgtcc cctgggctct gtctaggatg ttccttaaaa caatccctca gctgggccta 1140
ccctctaagt ctttatcctc agcccagaa gaggacctgg gaggcagcct tacagaaatc 1200
tctagaaatc ccttgtctct tctccccagt tcaccccaat ggctaaattc ctgaaactcc 1260
tgcttctccc ccaaaaccca actgaacgtg tcaggtcctt caggatggcg tcacctgctc 1320
ctagcagtta tgtagcccat cactttagcc ttttgctcac ctgcagacgg gaagtctctt 1380
ccacactgtg ggaaaacagg gtcctgccca aatcagagct gcccgagga atgtggcaac 1440
cgctagggag tctgtgcccc atgccacttc atgcaggaag catttgggc cagccaatat 1500
ggctgctttg ctggctaatg ctgaaagact tttccccccc acattgcctt tggtatacta 1560
ttaaaagata agaaaaatga cgagaaggaa gaggaagagg aggaagagga ggaagaagaa 1620
gatgaggagg aggaggagga ggaggaaaga tcgatttttt tggcctttac tttgaagggg 1680
ctgacatggc tgccccacgc ccctggtttg agaaaggttt caacgtgaag cctaggttct 1740
gcttatttta tgaatctcct gagtgttggg gattccagat gagcattccc atgcccaacc 1800
tgactttatt tcagttctga caatctcctc cctgtctctg aacaagattc tctgaagatg 1860
tcactgacta accaaccacc tagtggattg ctccctagag ccccatgatg ccaggaaaag 1920
attcatcctg gttggtctga cttcgttag ccagcatgag atcgacaggg gaaccccca 1980
tttctttggg ggtacactgt ttaaataggt tgagagacac agggatctgt ttagaatatt 2040
tcatgtctgc caggcccact acactcccat gtctcctgtc ctgcagtgac ctggggggaga 2100
gacgctgaat agaatctatt ctgggaaatg agccccagg aagagcagga atagtgggat 2160
acttgtcact tcccctcttc tttctagatt ccctgaggtt tcattaagtg acacttacta 2220
ggtccatatc agtgtacgga tgacaccatt gtggaatgtg ttggaggcaa tgtgcagctt 2280
gtatggaatc cagaagtgac ccttcctctg acccagcttc agattgtgtc tctaaaatgc 2340
atgacggagg tagttggccc atccctaccc tgatccgggt tactccaaac ccttcaggcc 2400
aagtttcagt ctttgcatgg ctttagtgct ttggagaggg aaatgtgcag cgtcactgct 2460
ctggctccct gtacaggctc atctgggaac accttataca tatatataca catatactac 2520
```

*FIG. 2A*

```
atgtatatat acatatacta tacatataca tatcatggct atctcaggat aggaggagga 2580
gtctaaagcc gtgaagtcga aagagctga ttcccctcaa agtctcttca ttttgctcca 2640
aacctcagaa tcctttactg agtccctctt ctgtaggccc gtggcctttc ccaagaccac 2700
agaactgtgg ttctcagcct tcctaatgct gagacccttt agtacagttc ctcatgttgt 2760
ggtgacccc ccagccccc cccacaggca acataaaaat attttttgttg ctacttcata 2820
actgtaattt tgttactatt atggatcata atgaactctc tgacatgcag gccatctgat 2880
atgcgacccc tgtgaaaggg ttgttggaca gtccctccaa agggttgagg gttgagaatc 2940
acagctggag gaggtggaga tgagaagggc agcgctttgg gagccttcag tgtctacagc 3000
ctctgttatg ccacgatgag agacaggggc cccctgacag ggagctacat ttggtgttct 3060
tgcggttaga gacagacacg tgagacattt ggtggctttc ctttctgact cctcttagtt 3120
gcttagagca gggatcagga tcaggtgagg aaacccacag gagggctctg gnccagcaaa 3180
catttactaa ctactacttt ccctgctaca agagagccat ccaggagggg actcgggact 3240
agtaatgatg ggcaggaagg gatagcgtga ggagccagct cccttcctca taagatcctc 3300
atactactgc tccattggaa attggggtgc ccaagaggtg ccagcacccc acccagcttc 3360
agtactgtgt gcagagggat gagatagtgg attacactgg gggggggggg caataggaag 3420
attgttgagt tctcttctc agaagtccag cagatctggg tgagggctgg gactggttgg 3480
tccctctctt cccacaggta tcggagcccc ctcttgttcc caggggagcc taggagcagc 3540
tgggccaaag cccaaccagg aattttttcca ggctggttcc tatatccaag ggtgggttag 3600
aggtggggt tttggagagc tcttaaggaa gacactgagg acatggagaa gggacttag 3660
tagaaagaga gggacagag ccacacgggc taagtgtgca agcatagaga aatagccaag 3720
ggttttaggg agaatgggag gacagagtac accccctgaat tctgtttaga agatgaaccg 3780
taagcctagg ctagaactga gggagcctct actcccaccc ttccgagggt tggcggcagc 3840
gctgggcagc tggcctacct acctttctga atgctagggt aggtttgaat caccatgccg 3900
gcctggcccg cttctgcccc cattggcacc ctggcttcag ttccctggca acatctctgt 3960
gtgtgtgtgt gtgtgtgaga gagagagatc aggaggaaca agggcctctg tctgcccagc 4020
agttgtctct ccttcagggc tctgccagac tacacagtgc atacgtgggt ttccacaggt 4080
cgtctcactc cccgccactg actaactcca gaactccacc cccgttctca gtgccacaaa 4140
tttggtgcca aattctctcc agagaagcct ctctggaaac ttcccagagg atcccattca 4200
cccagggcc ctagctcctg atgactgcag atcagacaag ggctcagata agcatactcc 4260
cccccccccg taaccccctc cccacatata aacctacagt tatgcttccg aggtcaaaca 4320
cgcaactttt tgggtgtgtg tgtatgtcag aaacacgcaa ttatttggga gctcaaagtc 4380
tgccgcactc aagaatcatc tctcacccc tttccaagac ccgtgccatt tgagcaagag 4440
ttggggtgtg cataatgtag tcactagggg gcgctcggcc atcacgggga gatcgtaact 4500
tgggcgagcc gagtctgcgt gagggaggac gcgtgtttca atgtgagtgc gtgcatgctg 4560
tgtgtgtgtg tgtagtgtgt gtgtgaggtg ggggagaaag ccaggggtca ctctagttgt 4620
ccctatcctc atacgttcct gccagctctc cgccttccaa ccccactttt ctcctatatc 4680
ctgggaaagg gaattgtctt agaccctgtc cgcatataac ctcactctcc tgtctcccct 4740
gattcccaat actctgggat tcccagtgtg ttcctgagcc cagtttgaag gggtgcacag 4800
ataattttga ggccgtggac cctggtaagg ggtttagctt tccatttcgc ggtagtggcc 4860
tagggggctcc ccgaaaggcg gtgcctggct ccaccagacc gtccccgggg cgggtctggg 4920
cggggcttgg gggtggagct agatttcctc ttttcttcc accgctgtta ccggtgagaa 4980
gcgcagaggc ttggggcagc cgagctgcag cgaggccgcg cactggggg cgagctgagc 5040
ggcggcagcg gagctctgtc gcgagacgca gcgacaaggc agactattca gcggactcac 5100
cagcccggga gtctgtgctc tgggatttga tattcaaacc tcttaatttt tttttcttaa 5160
actgtattgt tttacgcttt aatttatttt tgcttcctat tcccctctta aatcgtgcca 5220
acggtttgag gaggttggtt cttcactccc tcaaatcact tcggattgtg gaaatcagca 5280
gacgaaagag gtatcaagag ctccagagag aagtcaagga agagagagag agaccggtca 5340
gagagagcgc gctggcgagc gaacagagag agggacaggg gcaaagttga cttgaccttg 5400
ctttggggg tgaccgccag agcgcggcgt gacctccccc ttcgatcttg catcggacca 5460
gtcgcgctga cggacagaca gacagacacc gccccagcc cagcgccca cctcctcgcc 5520
ggcgggctgc cgacggtgga cgcggcggcg agccgaggaa ccgaagcccg cgcccggagg 5580
cggggtggag ggggtcgggg ctcgcgggat tgcacggaaa cttttcgtcc aacttctggg 5640
ctcttctcgc tccgtagtag ccgtggtctg cgccgcagga gacaaaccga tcggagctgg 5700
gagaagtgct agctcgggcc tggagaagcc ggggcccgag aagagagggg aggaagagaa 5760
```

*FIG. 2B*

```
ggaagaggag aggggccgc agtgggcgct cggctctcag gagccgagct catggacggg 5820
tgaggcggcc gtgtgcgcag acagtgctcc agccgcgcgc gcgccccagg ccccggcccg 5880
ggcctcggtt ccagaaggga gaggagcccg ccaaggcgcg caagagagcg ggctgcctcg 5940
cagtccgagc cggagaggga gcgcgagccg cgccggcccc ggacggcctc cgaaaccatg 6000
```

```
       2210      2220      2230      2240      2250      2260      2270      2280      2290      2300
CCCAAAACAAGTGTAAAGTATTTCCCTATGTGTGTGGAGGGAGGGAGTATAGGAGGCTGATTTCACTGAGATCCTGTTAAATTTGGGTGCCATAGCCAAT
GGGTTTTGTTCACATTTCATAAAGGGATACACACACCTCCCTCCCTCATATCCTCCGACTAAAGTGACTCTAGGACAATTTAAACCCACGGTATCGGTTA 2310      2320      2330      2340      2350      2360      2370      2380      2390      2400
CAAAGACGCATCGTTTCCTCTAAGAATTCTAAATGGGGCGATTACCACGGGCCTGCAGGTTCTGGTTTGTATTAGAGGAGACACTGTCTTCTTAAGTAAA
GTTTCTGCGTAGCAAAGGAGATTCTTAAGATTTACCCCGCTAATGGTGCCCGGACGTCCAAGACCAAACATAATCTCCTCTGTGACAGAAGAATTCATTT 2410      2420      2430      2440      2450      2460      2470      2480      2490      2500
ACATAGAAGGGGAAGTGTCCAGAATTGTAAATAAGGCTTCGAGAGAAGCCTTGTCTGGCCACCGGGATGGAGAAGACCTACCTTCGCCTATCCAGGATCC
TGTATCTTCCCCTTCACAGGTCTTAACATTTATTCCGAAGCTCTCTTCGGAACAGACCGGTGGCCCTACCTCTTCTGGATGGAAGCGGATAGGTCCTAGG 2510      2520      2530      2540      2550      2560      2570      2580      2590      2600
ATCGTCCCTCCCTCTACCCAGATCTGACAGCCCTCCTTGGCTCTTTTGCTGAGGTTTGTTTGAGTTTGTTTTACTCTCTGCAAGAGAAGTTTCCTTAAAC
TAGCAGGGAGGGAGATGGGTCTAGACTGTCGGGAGGAACCGAGAAAACGACTCCAAACAAACTCAAACAAAATGAGAGACGTTCTCTTCAAAGGAATTTG 2610      2620      2630      2640      2650      2660      2670      2680      2690      2700
ATTCTACCCTGTTCACAAGTAAATACACCTCTTAGCTAAGAGGCCACACACCCAGGGGAACACCGATAAAAAGAACAAGCCAGAACCTTCAGAACGCTGT
TAAGATGGGACAAGTGTTCATTTATGTGGAGAATCGATTCTCCGGTGTGTGGGTCCCCTTGTGGCTATTTTTCTTGTTCGGTCTTGGAAGTCTTGCGACA 2710      2720      2730      2740      2750      2760      2770      2780      2790      2800
CGATAGGTACACCAAGCAGCCTTCATACGGAGTTTTCATTCGTGAGGAGCTGAATATACAACAAAGCTAAATGTGAGCAGACCAGGCATGCCTCTGCTAA
GCTATCCATGTGGTTCGTCGGAAGTATGCCTCAAAAGTAAGCACTCCTCGACTTATATGTTGTTTCGATTTACACTCGTCTGGTCCGTACGGAGACGATT 2810      2820      2830      2840      2850      2860      2870      2880      2890      2900
ATGAGGATGCCCACACAAACATGCCCAAGATCTTCAAGTATAATTTATTATATAGATTCGCTATGTGTTGACATGTTTTTATAGTGAACCTGGATTTT
TACTCCTACGGGTGTGGTTTGTACGGGTTCTAGAAGTTCATATTAAATAATATATCTAAGCGATACACAACTGTACAAAAATATCACTTGGACCTAAAA 2910      2920      2930      2940      2950      2960      2970      2980      2990      3000
ACAAACCCTCCTGGTTTGCCACCTGCTTCTGGCACCATACTTGAGGCTTAGGCACGTGATAAAGGAGCATGCCTGTTTCCCCCCTTATTTTTTTTAAAGA
TGTTTGGGAGGACCAAACGGTGGACGAAGACCGTGGTATGAACTCCGAATCCGTGCACTATTTCCTCGTACGGACAAAGGGGGGAATAAAAAAAATTTCT 3010      3020      3030      3040      3050      3060      3070      3080      3090      3100
AAAGCACCATGTTACATCATTAATCATGCATATCAGTGTAGTTTAGATCCGATGTAGAGACAATAATCTTATCTCTTTGTCTGGCTGAAAGACTGTCCTT
TTTCGTGGTACAATGTAGTAATTAGTACGTATAGTCACATCAAATCTAGGCTACATCTCTGTTATTAGAATAGAGAAACAGACCGACTTTCTGACAGGAA 3110      3120      3130      3140      3150      3160      3170      3180      3190      3200
TAAACTATCATTCTAAATGCATTTGGTTTTTGCCAGGAGTAAAACATGTCACAAGATATTTGTTGTCATTTCCCAGGCGTGGAAGGAAAGGAATGGAAAG
ATTTGATAGTAAGATTTACGTAAACCAAAAACGGTCCTCATTTTGTACAGTGTTCTATAAACAACAGTAAAGGGTCGGCACCTTCCTTTCCTTACCTTTC 3210      3220      3230      3240      3250      3260      3270      3280      3290      3300
AAAACGAGGGGTGAAGGCTGCTGTTCCTCTCTAGTCGCTACTTGAAGTCTACATAGCTGGGGGGGGGGGGGGGACTGTTCACATGGGACCGGTTTCCTCT
TTTTGCTCCCCACTTCCGACGACAAGGAGAGATCAGCGATGAACTTCAGATGTATCGACCCCCCCCCCCCCCTGACAAGTGTACCCTGGCCAAAGGAGA 3310      3320      3330      3340      3350      3360      3370      3380      3390      3400
TTGTTCCTACACTGGCGCCTCTGGCAAGAAACTCTCCCTTCTCTTCCCCCCAAGCATATCTTGGCTGAAAGGTCAGCTCTGAAAAGGGGCCTGGCCAAAG
AACAAGGATGTGACCGCGGAGACCGTTCTTTGAGAGGGAAGAGAAGGGGGGTTCGTATAGAACCGACTTTCCAGTCGAGACTTTTCCCCGACCGGTTTC 3410      3420      3430      3440      3450      3460      3470      3480      3490      3500
TTACTGTAGGGGACCGTGGTCATGGAACTGGGTAGACAAAAGCACTCTAGCAGCCACTGGAAGGACCGGGGGCTCTTCTCTGTGCATTTGCCCTGGAG
AATGACATCCCCTGGCACCAGTACCTTGACCCATCTGTTTTCGTGAGATCGTCGGTGACCTCTTCCTGGCCCCCGAGAAGAGACACGTAAACGGGACCTC 3510      3520      3530      3540      3550      3560      3570      3580      3590      3600
CCCTGACCACCGCCAGCCTCCCTGCATCTCCTTGCTATGGGTTTTCTGGACCGAGCCAGGCAGGAGTTCACAACCGAAATGTCTTCTAGGGCTAATCAGGT
GGGACTGGTGGCGGTCGAGGGACGTAGAGGAACGATACCCAAAAGACCTGGCTCGGTCCGTCCTCAAGTGTTGGCTTTACAGAAGATCCCGATTAGTCCA 3610      3620      3630      3640      3650      3660      3670      3680      3690      3700
AACTTCGGACGATTTAAAGTTGCCAGATGGACGAGAAAACAGTAGAGGCGTTGGCAACCTGGATAAGCGCCTATCTTCTAATTAAAACATTCAGACGGGG
TTGAAGCCTGCTAAATTTCAACGGTCTACCTGCTCTTTTGTCATCTCCGCAACCGTTGGACCTATTCGCGGATAGAAGATTAATTTTGTAAGTCTGCCCC 3710      3720      3730      3740      3750      3760      3770      3780      3790      3800
CGGGGGATG-CGGTGGCCAAAGCACCATAAAACAAAACTTCCAAGTACTGACCAACTCACTGCAAGTTTGTGCCCCGAGTACATCTAGGTTCAGGGGTCT
GCCCCCTAC-GCCACCGGTTTCGTGGTATTTTGTTTTGAAGGTTCATGACTGGTTGAGTGACGTTCAAACACGGGCTCATGTAGATCCAAGTCCCCAGA 3810      3820      3830      3840      3850      3860      3870      3880      3890      3900
TGTCTTCATGCTCCCAACTGCGGGCGGATTTTTGGTCCCTTGGGACTTTCAGTGCAGCGGCGAAGAGAGTTCTGCACTTGCAGGCCTCCTAATGAGGGCGC
ACAGAAGTACGAGGGTTGACGCCCGCCTAAAAACCAGGGAACCCTGAAAGTCACGTCGCCGCTTCTCTCAAGACGTGAACGTCCGAGGATTACTCCCGCG 3910      3920      3930      3940      3950      3960      3970      3980      3990      4000
AGTGGGCCTCGTGTTTCTGGTGATGCTTCCCAGGTTGCTGGGGGCAGCAAGTGTCTCAGAGCCCATTACTGGCTACATTTTACTTCCACCAGAAACCGAG
TCACCCGGAGCACAAAGACCACTACGAAGGGTCCAACGACCCCCGTCGTTCACAGATGTCGGGTAATGACCGATGTAAAATGAAGGTGCTTTGGCTC 4010      4020      4030      4040      4050      4060      4070      4080      4090      4100
CTGCCGTCCAGATTTGCTCTCAGATGCGACTTGCCGCCCGGCACAGTTCCGGGGTAGTGGGGGAGTGGGCGTGGGAAAACCGGGAAACCCAAACCTGGTATC
GACGCAGGTCTAAACGAGAGTCTACGCTGAACGGCGGGCCGTGTCAAGGCCCCATCACCCCCTCACCCGCACCCTTGGCCCTTTGGGTTTGGACCATAG 4110      4120      4130      4140      4150      4160      4170      4180      4190      4200
CAGTGGGGGCGTGGCCGGACGCAGGGAGTCCCCACCCCTCCCGGTAATGACCCCGCCCCCATTCGCTAGTGTGTAGCCGGCGCTCTCTTTCTGCCCTGA
GTCACCCCCCGCACCGGCCTGCGTCCCTCAGGGGTGGGGAGGGCCATTACTGGGGCGGGGGTAAGCGATCACACATCGGCCGCGAGAGAAAGACGGGACT 4210      4220      4230      4240      4250      4260      4270      4280      4290      4300
GTCCTCAGGACCCCAAGAGAGTAAGCTGTGTTTCCTTAGATCGCGCGACCCGCTACCCGGCAGGACTGAAAGCCCAGACTGTGTCCCGCAGCCGGGATAA
CAGGAGTCCTGGGGTTCTCTCATTCGACACAAAAGGAATCTAGCGCGCTGGCGATGGGCCGTCCTGACTTTCGGGTCTGACACAGGCGTCGGCCCTATT 4310      4320      4330      4340      4350      4360      4370      4380      4390      4400
CCTGGCTGACCCGATTCCGCGGACACCGCTGCAGCCGCGGCTGGAGCCAGGGCGCCGGTGCCCCGCGCTCTCCCCGGTCTTGCGCTGCGGGGCGCATAC
GGACCGACTGGGCTAAGGCGCCGTGTGGCGACGTCGGCGCCGACCTCGGTCCCGCGGCGCACGGGGCGCGAGAGGGCCAGAACGCGACGCCCCGCGTATG
```

FIG. 3B

```
        4410      4420      4430      4440      4450      4460      4470      4480
CGCCTCTGTGACTTCTTTGCGGGCCAGGGACGGAGAAGGAGTCTGTGCCTGAGAACTGGGCTCTGTGCCCAGCGCGAGGTGCAGATG
GCGGAGACACTGAAGAAACGCCCGGTCCCTGCCTCTTCCTCAGACACGGACTCTTGACCCGAGACACGGGTCGCGCTCCACGTCTAC
```

FIG. 3C

```
        10        20        30        40        50        60        70        80        90       100
AAATGTGCTGTCTTTAGAAGCCACTGCCTCAGCTTCTGCAGCTCAGATACCAAAGGAAGTCTGGTACACAGCATGATAAAAGACAATGGGACGGGGTCAC
TTTACACGACAGAAATCTTCGGTGACGGAGTCGAAGACGTCGAGTCTATGGTTTCCTTCAGACCATGTGTCGTACTATTTTCTGTTACCCTGCCCCAGTG 110       120       130       140       150       160       170       180       190       200
AGTGGCTCCCGTCCCTTTCAGGGGTATGGAGACGAGCTGTAGAGAGATGTCTCCAGGGAGTTTTCATTAATCAGCAATTTAGTCAGATCTGTGCATCCTA
TCACCGAGGGCAGGGAAAGTCCCCATACCTCTGCTCGACATCTCTCTACAGAGGTCCCTCAAAAGTAATTAGTCGTTAAATCAGTCTAGACACGTAGGAT 210       220       230       240       250       260       270       280       290       300
TGCTTTACAAGAAATGTCAGTGGGCCTGAGATCATCAGATGGAGGTTCATCGGGTTTCAATGTCCCGTATCCTTTTGTAAGACCTTGAAGTTGGCAACGC
ACGAAATGTTCTTTACAGTCACCCGGACTCTAGTAGTCTACCTCCAAGTAGCCCAAAGTTACAGGGCATAGGAAAACATTCTGGAACTTCAACCGTTGCG 310       320       330       340       350       360       370       380       390       400
AGGAAAACAGGAACTCCACCCTGGTGCCGTGAATTGCAGAGCTGTTGTGTTGGTTTGTGACCATCTGCCCATTCTTCCTGTTATGACAGAGCTTGTGAAC
TCCTTTTGTCCTTGAGGTGGGACCACGGCACTTAACGTCTCGACAACACAACCAAACACTGGTAGACGGGTAAGAAGGACAATACTGTCTCGAACACTTG 410       420       430       440       450       460       470       480       490       500
TTTAACTGGGACTGGGGCAAAGTCAATCCCACCTTTATACAATGAATTGCTGAAGAGGCCTTTTAAAACTTGGAGTGTGCATTGTTTATGGAAGGGCTTT
AAATTGACCCTGACCCCGTTTCAGTTAGGGTGGAAATATGTTACTTAACGACTTCTCCGGAAAATTTTGAACCTCACACGTAACAAATACCTTCCCGAAA

510
CCTATTGGATC
GGATAACCTAG
```

```
        4410      4420      4430      4440      4450      4460      4470      4480      4490      4500
AACTAACCCTCAGAGCTCCCAGAGACTAAGCCACCAACTAAAGAGCATACATGGGCTGGTTTGTGGTCCCTGGCAGAGGACTGCCTTGTCTGGCCTCAGT
TTGATTGGGAGTCTCGAGGGTCTCTGATTCGGTGGTTGATTTCTCGTATGTACCCGACCAAACACCAGGGACCGTCTCCTGACGGAACAGACCGGAGTCA 4510      4520      4530      4540      4550      4560      4570      4580      4590      4600
AGGAGAGGATGTGCCTAATCCTCTAGAGACTTGATGCCCCAGGGAAGGGGACAAGGAGGGGACAAGGTGGGGATTGGTGTGGGGTAGTGGGGGTTGGGGG
TCCTCTCCTACACGGATTAGGAGATCTCTGAACTACGGGGTCCCTTCCCCTGTTCCTCCCCTGTTCCACCCCTAACCACACCCCATCACCCCCAACCCCC 4610      4620      4630      4640      4650      4660      4670      4680      4690      4700
TGGGGGTGGGGATGTGAATGGGTGAGTGAGGGAGGGAATGAGTGAGTGGGTGGTACAGCATCCTCTCAGAGGCAAAGGGGAAGGGGAGTGGATAACAAAC
ACCCCCACCCCTACACTTACCCACTCACTCCCTCCCTTACTCACTCACCCACCATGTCGTAGGAGAGTCTCCGTTTCCCCTTCCCCTCACCTATTGTTTG 4710      4720      4730      4740      4750      4760      4770      4780      4790      4800
TCTGGGAGCAGGGACGGGGAAGGAGGGCAACATTTGTAATTAAATAAATAAAATAATTTAATAAAAAAAATGAAGAACAGGATAACTTGGGAATGGTTA
AGACCCTCGTCCCTGCCCCTTCCTCCCGTTGTAAACATTAATTTATTTATTTTATTAAATTATTTTTTTACTTCTTTGTCCTATTGAACCCTTACCAAT 4810      4820      4830      4840      4850      4860      4870      4880      4890      4900
CAGCAGGGCTGGGATTAGAACCCAAAAAGTTTATTCTGAGACTCTTTTCCAATACCAAGCTTAAAGTTTTCTTCAGAATTCTATAGAATGCCTTTTTGGC
GTCGTCCCGACCCTAATCTTGGGTTTTTCAAATAAGACTCTGAGAAAAGGTTATGGTTCGAATTTCAAAAGAAGTCTTAAGATATCTTACGGAAAAACCG 4910      4920      4930      4940      4950      4960      4970      4980      4990      5000
AGAAGTTCTTTGGACTTTAATAAAGAACATATTGAAGAGATGAAAAGAAGCTTACTAAGATCTAATGAAAATCAAGATGCTAGGCACAGTGCCAGATACT
TCTTCAAGAAACCTGAAATTATTTCTTGTATAACTTCTCTACTTTTCTTCGAATGATTCTAGATTACTTTTAGTTCTACGATCCGTGTCACGGTCTATGA 5010      5020      5030      5040      5050      5060      5070      5080      5090      5100
TTAACATAGTAATATGACTCTTTAGAGTTTTGAGACAGGGCCTCATATAGTTTATGATGAATTCACTGTTTTGTCAAAGATGACCTTGAACTCTTAATCC
AATTGTATCATTATACTGAGAAATCTCAAAACTCTGTCCCGGAGTATATCAAATACTACTTAAGTGACAAAACAGTTTCTACTGGAACTTGAGAATTAGG 5110      5120      5130      5140      5150      5160      5170      5180      5190      5200
ATTCCCAAAGTGTTGTTGTCATATGTTTGCACCACTCCTGGCTTCATAGTGTTTTTAAAACACCCATGGAGAGTCGGGTGTGAAGATCCACACGTCTAAC
TAAGGGTTTCACAACAACAGTATACAAACGTGGTGAGGACCGAAGTATCACAAAAATTTTGTGGGTACCTCTCAGCCCACACTTCTAGGTGTGCAGATTG 5210      5220      5230      5240      5250      5260      5270      5280      5290      5300
CTCAGCATCTGGTGAATCAAGGCAGGAGGGCGGGTGGTTGCAGGCTGGCTATAATATCTAAGTTTCAGTTAGTAAGGGCTGCATAATGAAACACTGTCTT
GAGTCGTAGACCACTTAGTTCCGTCCTCCCGCCCACCAACGTCCGACCGATATTATAGATTCAAAGTCAATCATTCCCGACGTATTACTTTGTGACAGAA 5310      5320      5330      5340      5350      5360      5370      5380      5390      5400
AAACACAAAACCAAAACCCATGAAGGAGATACTATTGCCATTTAAAAGTCTCTGGAATGGAAATAGCTATCATAATCTTACCTCTGAGCCAGTGTCTGCC
TTTGTGTTTTGGTTTTGGGTACTTCCTCTATGATAACGGTAAATTTTCAGAGACCTTACCTTTATCGATAGTATTAGAATGGAGACTCGGTCACAGACGG 5410      5420      5430      5440      5450      5460      5470      5480      5490      5500
CTCAGGTGTGCCTGAGGACTGAACAGGGCTATGCACTCCTCAGGTTGGAAACATTACTAGTCCTCAGTGTCTGCTCTTGACCTGTTAACAGCTGAGTCAG
GAGTCCACACGGACTCCTGACTTGCTCCCGATACGTGAGGAGTCCAACCTTTGTAATGATCAGGAGTCACAGACGAGAACTGGACAATTGTCGACTCAGTC 5510      5520      5530      5540      5550      5560      5570      5580      5590      5600
GGTCTGCCCTCAGCTGTGCCTGAGGACAGAGCTGAGCTATCTACCCCTGCAGATTGGAAGCATTACAGGCACTCAAGATCAGCCCTGAAGTGATAAAACC
CCAGACGGGAGTCGACACGGACTCCTGTCTCGACTCGATAGATGGGGACGTCTAACCTTCGTAATGTCCGTGAGTTCTAGTCGGGACTTCACTATTTTGG 5610      5620      5630      5640      5650      5660      5670      5680      5690      5700
TAAGGCAGAAATCCACCAAGACTAGCAGTGCCTCCGTGTCTCTTCCTGTGGCTGGTGGGAAAGAGAGGGGCAGTCCTTCCTTGATGCAAGGTCGTGTGTC
ATTCCGTCTTTAGGTGGTTCTGATCGTCACGGAGGCACAGAGAAGGACACCGACCACCCTTTCTCTCCCGTCAGGAAGGAACTACGTTCCAGCACACAG 5710      5720      5730      5740      5750      5760      5770      5780      5790      5800
TAGTGGCACGCTTCCTTCATTCCCAGTGAGAGCAAGTGATCACCTGGGTAAGGAAGGTTCAGGTGCCTGAGCTCGCTGGAGAATTCATCACTCATCCATC
ATCACCGTGCGAAGGAAGTAAGGGTCACTCTCGTTCACTAGTGGACCCATTCCTTCCAAGTCCACGGACTCGAGCGACCTCTTAAGTAGTGAGTAGGTAG 5810      5820      5830      5840      5850      5860      5870      5880      5890      5900
ACTCTGCTCCTGTAGACATAATCACTTCTGTTGGGTCTTTATAGAGATGATTTATAACTTTGTTGTTTATAGTTTTTATGAATGTGTGTATTCATTTAGG
TGAGACGAGGACATCTGTATTAGTGAAGACAACCCAGAAATATCTCTACTAAATATTGAAACAACAAATATCAAAAATACTTACACACATAAGTAAATCC 5910      5920      5930      5940      5950      5960      5970      5980      5990      6000
TCACATGGGAGGTACACATTTTCAGGTGTCTGTCTTTCCATCACACGGGCTTTGAATTAAACTCAGTCTTGGTTTTACCGGCTGAGCCATCTCACCTGCC
AGTGTACCCTCCATGTGTAAAAGTCCACAGACAGAAAGGTAGTGTGCCCGAAACTTAATTTGAGTCAGAACCAAAATGGCCGACTCGGTAGAGTGGACGG 6010      6020      6030      6040      6050      6060      6070      6080      6090      6100
TGATTATTTAAAAATCTCCGGAGTAATCCAGGAGTGTGGTTTATGATTGTAGTATCAACACTCGGGAGGCTGAGGGAGCATCGTTATCATGAGCTCCAGG
ACTAATAAATTTTTAGAGGCCTCATTAGGTCCTCACACCAAATACTAACATCATAGTTGTGAGCCCTCCGACTCCCTCGTAGCAATAGTACTCGAGGTCC 6110      6120      6130      6140      6150      6160      6170      6180      6190      6200
CTAGTTCCAGGCTTGCCTAAGCTGTAGAGCAAGTCACTCTCTTAAAAAGTGCCTCTCCCATATTTTTGTATATAATTTGCATCTGAAATTCTGTTTGCCA
GATCAAGGTCCGAACGGATTCGACATCTCGTTCAGTGAGAGAATTTTTCACGGAGAGGGTATAAAAACATATATTTAAACGTAGACTTTAAGACAAACGGT 6210      6220      6230      6240      6250      6260      6270      6280      6290      6300
ATAACTATGAAATTATTCACATTACTAAAATCTTCCTGTGCCAAGTTCTCCAACGAATTAGATCACACTCAGATGAAATGCTAATAAAAATTAAAGCTGT
TATTGATACTTTAATAAGTGTAATGATTTTAGAAGGACACGGTTCAAGAGGTTGCTTAATCTAGTGTGAGTCTATTTACGATTATTTTTAATTTCGACA 6310      6320      6330      6340      6350      6360      6370      6380      6390      6400
AGCCAGTAGCATGCGTATATTTGGGCTCAGGGCCAACAGGCAGGCGATCTGGGTGTAAGAAAATAGGCTAATGGCTGTGGAATCTGGTCTCTAGTGGCTC
TCGGTCATCGTACGCATATAAACCCGAGTCCCGGTTGTCCGTCCGCTAGACCCACATTCTTTTATCCGATTACCGACACCTTAGACCAGAGATCACCGAG 6410      6420      6430      6440      6450      6460      6470      6480      6490      6500
CGCTGAGAGCTGACCTCAACCACGCTCCCTCAAATTGATTGCCTTCCAGGTTATGATTTCTCATCACAGGAAACTTTGTTGCCCAATTCAAACCCTGTGA
GCGACTCTCGACTGGAGTTGGTGCGAGGGAGTTTAACTAACGGAAGGTCCAATACTAAAGAGTAGTGTCCTTTGAAACAACGGGTTAAGTTTGGGACACT 6510      6520      6530      6540      6550      6560      6570      6580      6590      6600
GTGAAAACAAAAACAGGAGAGCAAGTGCTGCTCCCCGTGCCCCAAAGCCCCTTCGTCAGGGATCCCAAATGCACCCCAGAGAACAGCTTAGCCTGCAAG
CACTTTTGTTTTTGTCCTCTCGTTCACGACGAGGGGCACGGGGTTTCGGGGAAGACAGTCCCTAGGGTTTACGTGGGGTCTCTTGTCGAATCGGACGTTC
```

FIG. 6C

```
       6610      6620      6630      6640      6650      6660      6670      6680      6690     6700
GGCTGGTCCTCATCGCATACCATACATAGGTGGAGGGCTTGTTATTCAATTCCTGGCCTATGAGAGGATACCCCTATTGTTCCTGAAAATGCTGACCAGG
CCGACCAGGAGTAGCGTATGGTATGTATCCACCTCCCGAACAATAAGTTAAGGACCGGATACTCTCCTATGGGATAACAAGGACTTTTACGACTGGTCC 6710      6720      6730      6740      6750      6760      6770      6780      6790     6800
ACCTTACTTGTAACAAAGATCCCTCTGCCCCACAATCCAGTTAAGGCAGGAGCAGGAGCCGGAGCAGGAGCAGAAGATAAGCCTTGGATGAAGGGCAAGA
TGGAATGAACATTGTTTCTAGGGAGACGGGGTGTTAGGTCAATTCCGTCCTCGTCCTCGGCCTCGTCCTCGTCTTCTATTCGGAACCTACTTCCCGTTCT 6810      6820      6830      6840      6850      6860      6870      6880      6890     6900
TGGATAGGGCTCGCTCTGCCCCAAGCCCTGCTGATACCAAGTGCCTTTAAGATACAGCCTTTCCCATCCTAATCTGCAAAGGAAACAGGAAAAAGGAACT
ACCTATCCCGAGCGAGACGGGGTTCGGGACGACTATGGTTCACGGAAATTCTATGTCGGAAAGGGTAGGATTAGACGTTTCCTTTGTCCTTTTTCCTTGA 6910      6920      6930      6940      6950      6960      6970      6980      6990     7000
TAACCCTCCCTGTGCTCAGACAGAAATGAGACTGTTACCGCCTGCTTCTGTGGTGTTTCTCCTTGCCGCCAACTTGTAAACAAGAGCGAGTGGACCATGC
ATTGGGAGGGACACGAGTCTGTCTTTACTCTGACAATGGCGGACGAAGACACCACAAAGAGGAACGGCGGTTGAACATTTGTTCTCGCTCACCTGGTACG 7010      7020      7030      7040      7050      7060      7070      7080      7090
GAGCGGGAAGTCGCAAAGTTGTGAGTTGTTGAAAGCTTCCCAGGGACTCATGCTCATCTGTGGACGCTGGATGGGGAGATCTGGGAAGTATG
CTCGCCCTTCAGCGTTTCAACACTCAACAACTTTCGAAGGGTCCCTGAGTACGAGTAGACACCTGCGACCTACCCCTCTAGACCCCTTCATAC
```

FIG. 6D

```
        10         20         30         40         50         60         70         80         90        100
CTCGAGGTCCAGTATGGCTTCTCAACCTTCTTGGCAAGAAGGCTGCAGGGACGACCAGGAAGTTTGAAACAGTCTTAGAAGAAAATGCTGGCTTAGAGAC
GAGCTCCAGGTCATACCGAAGAGTTGGAAGAACCGTTCTTCCGACGTCCCTGCTGGTCCTTCAAACTTTGTCAGAATCTTCTTTTACGACCGAATCTCTG 110        120        130        140        150        160        170        180        190        200
AGGTGGCAATGGGGGATGGGGAGCAGTATTCTGGTTTGCATAGAGGCAGAGTCCTTCCAAGTGCTGGGAAACAAGGCAGGAGGGCAGGGATAGAGCAAAT
TCCACCGTTACCCCCTACCCCTCGTCATAAGACCAAACGTATCTCCGTCTCAGGAAGGTTCACGACCCTTTGTTCCGTCCTCCCGTCCCTATCTCGTTTA 210        220        230        240        250        260        270        280        290        300
GATGGCTCTGTATGTGTCCCTGTTCAGTTTGCATTTAATCTGAGCAAAATTTGGCTTTTGACATCTGCAACTCAAAAGAAGGTAATTAGGCAAATGACTG
CTACCGAGACATACACAGGGACAAGTCAAACGTAAATTAGACTCGTTTTAAACCGAAAACTGTAGACGTTGAGTTTTCTTCCATTAATCCGTTTACTGAC 310        320        330        340        350        360        370        380        390        400
ACACATAGATATCTTAATAGTCAAGGAATTTTTTTTTTTTTTTGAAGAGTTAGCAGTCAGGGGATGGTAGAAACTGCAAAACCAATCCGTATTCTTTC
TGTGTATCTATAGAATTATCAGTTCCTTAAAAAAAAAAAAAAAACTTCTCAATCGTCAGTCCCCTACCATCTTTGACGTTTTGGTTAGGCATAAGAAAG 410        420        430        440        450        460        470        480        490        500
TTGAGATTTTTAGACAGTTGATGCTACTAGCCACAAAAGAGTTTAAGTGGGAGGAGAGTAAGATGCAGGCACCAAGGTGACAGGCTCCAGGTCTGTAG
AACTCTAAAAATCTGTCAACTACGATGATCGGTGTTTTTCTCAAAATTCACCCTCCTCTCATTCTACGTCCGTGGTTCCACTGTCCGAGGTCCAGACATC 510        520        530        540        550        560        570        580        590        600
CATTAGCTTACAGATGAGATTCTTTACAGAGAGCCAGGCAGCTGCATTGGCTAAAGCAGATCTGGGAGGGGGCCAGGAGATCAGCTGGCGGCACTCCCAG
GTAATCGAATGTCTACTCTAAGAAATGTCTCTCGGTCCGTCGACGTAACCGATTTCGTCTAGACCCTCCCCGGTCCTCTAGTCGACCGCCGTGAGGGTC 610        620        630        640        650        660        670        680        690        700
CCTCCAGGAAAGGCAACCCTTATTTCTGGAATTTTAAACTGATAACCCAATTCCCACCAGCCTGGCCAGGCTCTTCCTTAGCTCACATCACAAACACAGA
GGAGGTCCTTTCCGTTGGGAATAAAGACCTTAAAATTTGACTATTGGGTTAAGGGTGGTCGGACCGGTCCGAGAAGGAATCGAGTGTAGTGTTTGTGTCT 710        720        730        740        750        760        770        780        790        800
AGGATTGTTTTAGATGGAGTCATGCTTGATTCTTTCTATACCTACTTCCAAGACCAATTTTATAAAAGTTTATTTACCGCCCGTGTGTGTGTGTGTGTGT
TCCTAACAAAATCTACCTCAGTACGAACTAAGAAAGATATGGATGAAGGTTCTGGTTAAAATATTTTCAAATAAATGGCGGGCACACACACACACACACA 810        820        830        840        850        860        870        880        890        900
GTGTGTGTGTGTGTGTGTGTGTGTGCATGGTATATATGGATGTCAGAGTTTGGTTCTCTCCTTCTGCAGTGTGGCTCTTAGAGATTGAACTCAGAT
CACACACACACACACACACACACACGTACCATATATACCTACAGTCTCAAACCAAGAGAGGAAGACGTCACACCGAGAATCTCTAACTTGAGTCTA 910        920        930        940        950        960        970        980        990       1000
CATGAGCAAGCACCTTGCTGCCTGCTATGTCCCTCCAGCAGTCTGACCATGTTCCTTCCCCCAAGATTGTGGAAGCTGGACTGAAGATCACAATCTGCCA
GTACTCGTTCGTGGAACGACGGACGATACAGGGAGGTCGTCAGACTGGTACAAGGAAGGGGGTTCTAACACCTTCGACCTGACTTCTAGTGTTAGACGGT 1010       1020       1030       1040       1050       1060       1070       1080       1090       1100
GATGGGCAGAATCTTTACTCTTTGGCACATTTGTTGCTGATGGGGAGTGAATACCCATGGGGACATGGCTGTCATGGTGTGGAAGTGATAGAAATGAAAA
CTACCCGTCTTAGAAATGAGAAACCGTGTAAACAACGACTACCCCTCACTTATGGGTACCCCTGTACCGACAGTACCACACCTTCACTATCTTTACTTTT 1110       1120       1130       1140       1150       1160       1170       1180       1190       1200
CATGTATGGATCTGTCACAGGAGCTGGTGAGGCTGATGGGTGTGTGGGTGGCCACTGTTTGCTCTCTGCTTGTCACAGCCTCTTGTTCAGGGCTTGATCA
GTACATACCTAGACAGTGTCCTCGACCACTCCGACTACCCACACACCCACCGGTGACAAACGAGAGACGAACAGTGTCGGAGAACAAGTCCCGAACTAGT 1210       1220       1230       1240       1250       1260       1270       1280       1290       1300
GGCAGGTGTGTGTGTGTGTGTGTGTGTGTGTGTGTGTGTGTGGTCACACCCATCTCAGCAGATCTGTCAGCTTTCCCGCTTTTGTTAGAGGGTG
CCGTCCACACACACACACACACACACACACACACACACACACACCAGTGTGGGTAGAGTCGTCTAGACAGTCGAAAGGGCGAAAACAATCTCCCAC 1310       1320       1330       1340       1350       1360       1370       1380       1390       1400
ATATCATGCTTCCTGGGGGGAGCTCTGGAAGACAATGAGCAGCCACTTTCCTCTAGATACAATAGGCGGAGTCAGGAAGGTAGTATTGACATTGCTGGGG
TATAGTACGAAGGACCCCCCTCGAGACCTTCTGTTACTCGTCGGTGAAAGGAGATCTATGTTATCCGCCTCAGTCCTTCCATCATAACTGTAACGACCCC 1410       1420       1430       1440       1450       1460       1470       1480       1490       1500
CCTAGGAGCTACTCACTGCTCGGTGGCCGTCAGATGGTGAACCGGCGTAACCTTGGCACACAGGCCTGGGCTGTACAAGGCGTCTGGCTGCAGGGCCAAA
GGATCCTCGATGAGTGACGAGCCACCGGCAGTCTACCACTTGGCCGCATTGGAACCGTGTGTCCGGACCCGACATGTTCCGCAGACCGACGTCCCGGTTT 1510       1520       1530       1540       1550       1560       1570       1580       1590       1600
GAGGACTCCACCCTAGGGACAGGAGTACTTCAGACATCTGGGAATCTGGGATGGGTTTTAAAATTCAGATCCCAATATAAAAAAACAACTCCCAAACAAA
CTCCTGAGGTGGGATCCCTGTCCTCATGAAGTCTGTAGACCCTTAGACCCTACCCAAAATTTTAAGTCTAGGGTTATATTTTTTTGTTGAGGGTTTGTTT 1610       1620       1630       1640       1650
CAGCAGCAATTAAAAAAAAAAAAAAAAACCAGCCTCCCAAGTAAAACAATAATGGTACC
GTCGTCGTTAATTTTTTTTTTTTTTTTTGGTCGGAGGGTTCATTTTGTTATTACCATGG
```

FIG. 7

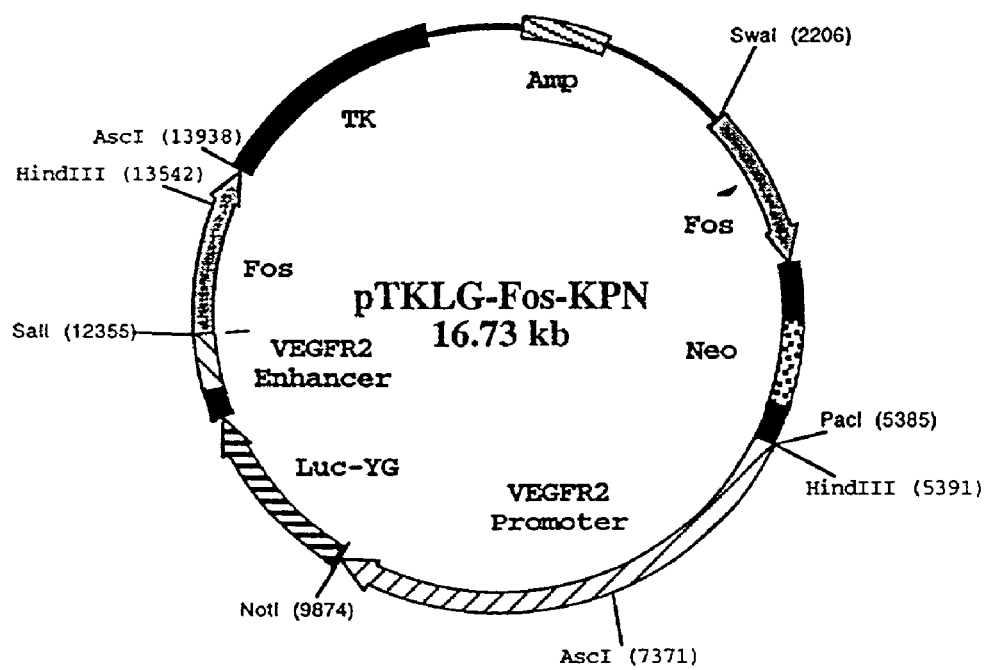
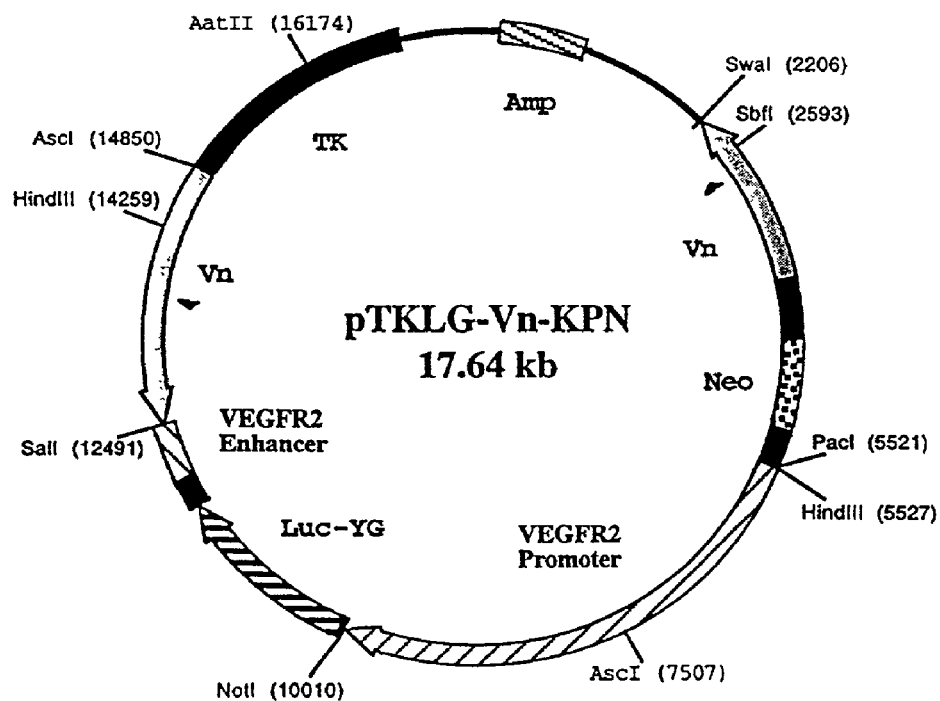
FIG. 14

VEGFR2-Luc KC  VEGFR2-Luc KJ  VEGFR2-Luc KG  VEGFR2-Luc KA

SEQUENCE LISTING

```
<160> NUMBER OF SEQ ID NOS: 45

<210> SEQ ID NO 1
<211> LENGTH: 31
<212> TYPE: DNA
```

```
<213> ORGANISM: Artificial Sequence
<220> FEATURE:
<223> OTHER INFORMATION: Description of Artificial Sequence: primer PGKF

<400> SEQUENCE: 1
atcgaattct accgggtagg ggaggcgctt t                                   31

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: primer PGKR

<400> SEQUENCE: 2
ggctgcaggt cgaaaggccc ggagatgagg                                     30

<210> SEQ ID NO 3
<211> LENGTH: 32
<212> TYPE: DNA
<213> ORGANISM: Artificial Sequence
<220> FEATURE:
<223> OTHER INFORMATION: Description of Artificial Sequence: primer NeoF

<400> SEQUENCE: 3
acctgcagcc aatatgggat cggccattga ac                                  32

<210> SEQ ID NO 4
<211> LENGTH: 37
<212> TYPE: DNA
<213> ORGANISM: Artificial Sequence
<220> FEATURE:
<223> OTHER INFORMATION: Description of Artificial Sequence: primer NeoR

<400> SEQUENCE: 4
ggatccgcgg ccgcccccag ctggttcttt ccgcctc                             37

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: primer TKF

<400> SEQUENCE: 5
ggatcctcta gagtcgagca gtgtggtttt                                     30

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: primer TKR

<400> SEQUENCE: 6
gagctcccgt agtcaggttt agttcgtccg                                     30

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: primer
      F5R51

<400> SEQUENCE: 7
```
gtacatttaa atcctgcagg                                             20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: primer
      F5R52

<400> SEQUENCE: 8
agctcctgca ggatttaaat                                             20

<210> SEQ ID NO 9
<211> LENGTH: 77
<212> TYPE: DNA
<213> ORGANISM: Artificial Sequence
<220> FEATURE:
<223> OTHER INFORMATION: Description of Artificial Sequence: primer
      F3R31

<400> SEQUENCE: 9
ggcccgggct taattaatgc atcatatggt accgtttaaa cgcggccgca agcttgtcga    60
cggcgcgccg gccggcc                                                 77

<210> SEQ ID NO 10
<211> LENGTH: 77
<212> TYPE: DNA
<213> ORGANISM: Artificial Sequence
<220> FEATURE:
<223> OTHER INFORMATION: Description of Artificial Sequence: primer
      F3R32

<400> SEQUENCE: 10
gatcggccgg ccggcgcgcc gtcgacaagc ttgcggccgc gtttaaacgg taccatatga    60
tgcattaatt aagcccg                                                 77

<210> SEQ ID NO 11
<211> LENGTH: 39
<212> TYPE: DNA
<213> ORGANISM: Artificial Sequence
<220> FEATURE:
<223> OTHER INFORMATION: Description of Artificial Sequence: primer VN1R

<400> SEQUENCE: 11
ctgtatttaa atctgcccac cctattcagg acagtagtc                         39

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence: primer VN1F

<400> SEQUENCE: 12
ccaatgcatc aacccagcca ggaggagtgc g                                 31

<210> SEQ ID NO 13
<211> LENGTH: 38
<212> TYPE: DNA
<213> ORGANISM: Artificial Sequence
<220> FEATURE:
<223> OTHER INFORMATION: Description of Artificial Sequence: primer VN2R

<400> SEQUENCE: 13
aacgcgtcga cttcggagat gtttcgggga taaccagg                              38

<210> SEQ ID NO 14
<211> LENGTH: 40
<212> TYPE: DNA
<213> ORGANISM: Artificial Sequence
<220> FEATURE:
<223> OTHER INFORMATION: Description of Artificial Sequence: primer VN2F

<400> SEQUENCE: 14
ttggcgcgcc ccatagagaa gagacaccaa aggcacgctc                            40

<210> SEQ ID NO 15
<211> LENGTH: 36
<212> TYPE: DNA
<213> ORGANISM: Artificial Sequence
<220> FEATURE:
<223> OTHER INFORMATION: Description of Artificial Sequence: primer
      FosB1F

<400> SEQUENCE: 15
ctgtatttaa atcccgtttc tcactgtgcc tgtgtc                                36

<210> SEQ ID NO 16
<211> LENGTH: 35
<212> TYPE: DNA
<213> ORGANISM: Artificial Sequence
<220> FEATURE:
<223> OTHER INFORMATION: Description of Artificial Sequence: primer
      FosB1R

<400> SEQUENCE: 16
gtctcctgca ggcttcctcc tccttgttcc ttgcg                                 35

<210> SEQ ID NO 17
<211> LENGTH: 35
<212> TYPE: DNA
<213> ORGANISM: Artificial Sequence
<220> FEATURE:
<223> OTHER INFORMATION: Description of Artificial Sequence: primer
      FosB2F

<400> SEQUENCE: 17
aacgcgtcga cggatgggat tgaccccag ccctc                                  35

<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence: primer
      FosB2R

<400> SEQUENCE: 18
ttggcgcgcc ccttgcctcc acctctcaaa tgc                                   33

<210> SEQ ID NO 19
<211> LENGTH: 31
<212> TYPE: DNA
<213> ORGANISM: Artificial Sequence
<220> FEATURE:
<223> OTHER INFORMATION: Description of Artificial Sequence: primer VF1

<400> SEQUENCE: 19
acctcactct cctgtctccc ctgattccca a                                     31

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: primer VR1A

<400> SEQUENCE: 20
gctctggcgg tcaccccccaa aagca                                    25

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence: primer VF2

<400> SEQUENCE: 21 cccttttccaa gacccgtgcc atttgagc                                 28

<210> SEQ ID NO 22
<211> LENGTH: 29
<212> TYPE: DNA
<213> ORGANISM: Artificial Sequence
<220> FEATURE:
<223> OTHER INFORMATION: Description of Artificial Sequence: primer VR2

<400> SEQUENCE: 22
actttgcccc tgtccctctc tctgttcgc                                 29

<210> SEQ ID NO 23
<211> LENGTH: 28
<212> TYPE: DNA
<213> ORGANISM: Artificial Sequence
<220> FEATURE:
<223> OTHER INFORMATION: Description of Artificial Sequence: primer KF1

<400> SEQUENCE: 23
gctgcgtcca gatttgctct cagatgcg                                  28

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence: primer KR1

<400> SEQUENCE: 24
ttctcaggca cagactcctt ctccgtccct                                30

<210> SEQ ID NO 25
<211> LENGTH: 32
<212> TYPE: DNA
<213> ORGANISM: Artificial Sequence
<220> FEATURE:
<223> OTHER INFORMATION: Description of Artificial Sequence: primer KF2

<400> SEQUENCE: 25
cagatggacg agaaaacagt agaggcgttg gc                             32

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: primer KR2

```
<400> SEQUENCE: 26
gaggactcag ggcagaaaga gagcg                                             25

<210> SEQ ID NO 27
<211> LENGTH: 29
<212> TYPE: DNA
<213> ORGANISM: Artificial Sequence
<220> FEATURE:
<223> OTHER INFORMATION: Description of Artificial Sequence: primer TF3

<400> SEQUENCE: 27
agcttagcct gcaagggtgg tcctcatcg                                         29

<210> SEQ ID NO 28
<211> LENGTH: 31
<212> TYPE: DNA
<213> ORGANISM: Artificial Sequence
<220> FEATURE:
<223> OTHER INFORMATION: Description of Artificial Sequence: primer TF2

<400> SEQUENCE: 28
caaatgcacc ccagagaaca gcttagcctg c                                      31

<210> SEQ ID NO 29
<211> LENGTH: 33
<212> TYPE: DNA
<213> ORGANISM: Artificial Sequence
<220> FEATURE:
<223> OTHER INFORMATION: Description of Artificial Sequence: primer TR1

<400> SEQUENCE: 29
gctttcaaca actcacaact ttgcgacttc ccg                                    33

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: primer VR2F

<400> SEQUENCE: 30
cgctagtgtg tagccggcgc tctc                                              24

<210> SEQ ID NO 31
<211> LENGTH: 38
<212> TYPE: DNA
<213> ORGANISM: Artificial Sequence
<220> FEATURE:
<223> OTHER INFORMATION: Description of Artificial Sequence: primer VR2R

<400> SEQUENCE: 31
ataagaatgc ggccgcctgc acctcgcgct gggcacag                               38

<210> SEQ ID NO 32
<211> LENGTH: 4487
<212> TYPE: DNA
<213> ORGANISM: Mus sp.

<400> SEQUENCE: 32
aagcttgcag ggaggtagga ggcagcctgt ggcgttgatt caatgcacct ggccttatcc       60
tcggatgaga tcggtcacca gtcaaaaact gtgagcttga aggtcttggg tgcttaacat      120
ctatttttac aaatcttatt tagcaactta gaactgtgaa atattggaaa gctacttaaa      180
ccttctaaac tccctcctcc acactatgag aatgttacat tttctattca gttattttg       240
```

-continued

```
agcagtaaac agatgaatca aggaatatgc ccatcacatc aagagtgctc ctaaatggac    300
ttgcttgtta ttcatttaca gtgtggcccc ttgactttca tcggcactcc tagcagaaaa    360
caaaatccgc cagatggagc tggagagatg gctcagctgt taagaatact tatccctaca    420
caggccctgg agccagttcc cagcacccac acggtggctc acaaccatct gtaactccag    480
ttctaggaga cccgactccc tcttctgtct gaaaacacca ggcacgcgtg cggtctacat    540
acaaacatga aagcaaaata cacacattac ataaataaat cttaaaaaat gattcggggt    600
gggggaagga aaaaaaagga tgttagaaaa tcgatgtaac tgtttttttcc ttttgcacag    660 atctaagtag ggaaggagaa cattctctta ccatcgagaa taattgtttt cattgccccc    720
aagtctgcta atagagcttg ctaccttcat ggctgtcgta aggatgaggc aaagatggac    780
ttcagctttc agactgtgtc tgctcaaatg ttggctactc ctgttttctg accccccttct   840 ctggtgcaat gtggacttt caattaatttc cctgcatctt ttacatattt gatttaaaaa    900
atattttatt ttatgtaatt gtatgtatat gcatgtcaat aagcatatgt gtgtgtgttt    960
ccatggaaac caaggcaaca gattctccag agctgtagaa atgggctgtg agacgcccac   1020
tgtgggtgct cggaaccaaa ctcgggtcct gtggaaagac agcgagcacc cataatgcag   1080
aggtatctct cagactctac tttaaaattt caatttatct ttttttttttt taaagttcca   1140 agtaactata ggaaagtaca tgggtatata gatccccagt accaagattc ttcctttgca   1200
ggtagcacaa cttggtctgc ttcacataaa gaatggaaag tcattaaaac actcatcaca   1260
ctgtaaagta gaattgaact ctgacagaac aagcgaagtg agtctgactt ccaggtaact   1320
gagccttctt ttcctcctaa agacacaagc catacacaga gtaaaataaa cttgggcatg   1380
gtgagaagga acaacgcag gagggctagc caagtctgag agtcgtgagt gtgctcggtt    1440
tataaacgga gcccaccttg ccagcgaggt agtcacatgc tctgctaaac agaaacttaa   1500
gaaaacactt acacgaagca acatggggga agtgccatgc aagcatgtga ctgactggtg   1560
gcaatgaccg aaaccacagc agccactaga aaggaaggg tagtgcgcca cactgtagtt    1620
gtgaaaatga acttattcat ttattttgaa aaacgtgtaa gaagcaaaga tgtcttcttt   1680
cccacctacc tttgcggcag gcgagcactt cctggaattt ataaagtgcg atctttctgg   1740
ggacttctca taacatttcc tactgctcat ctatgtctgt gtcaaataga gaatgctctt   1800
gaacaagtgt gtgtgtgtgt gtgtgtgcgc gcgcacgcgc actcactcct gctctgttga   1860
ggtccagttt tgatggtccc gccagaggta tatttgagta tcattctcta agagcttcag   1920
ctgggagaca ctgcctctta ctggcctgaa ggtcactagc tgattcatct ccgtttgggc   1980
tggcgcgcct tggggatcct cctatctctc cttcccagt gctgggataa caaggttggc    2040
accacatgag cctttaaaa tgtgagtttg gaagctcaaa cgcaggtttt catgcttgca    2100
ctgaaacttc acaagctgaa ccgtctccct tccttccct ctcttttttc cttttcttct    2160
tcctttttaa aacacatctt gtctttaaaa aaaaaaaag gcccaaaaca agtgtaaagt    2220
atttccctat gtgtgtggag ggagggagta taggaggctg atttcactga gatcctgtta   2280
aatttgggtg ccatagccaa tcaaagacgc atcgtttcct ctaagaattc taaatggggc   2340
gattaccacg ggcctgcagg ttctggtttg tattagagga gacactgtct tcttaagtaa   2400
aacatagaag gggaagtgtc cagaattgta ataaggcttc gagagaagc cttgtctggc    2460 caccgggatg gagaagacct accttcgcct atccaggatc catcgtccct ccctctaccc   2520
agatctgaca gccctccttg gctctttgc tgaggtttgt ttgagtttgt tttactctct   2580
```

```
gcaagagaag tttccttaaa cattctaccc tgttcacaag taaatacacc tcttagctaa    2640
gaggccacac acccagggga acaccgataa aaagaacaag ccagaacctt cagaacgctg    2700
tcgataggta caccaagcag ccttcatacg gagttttcat tcgtgaggag ctgaatatac    2760
aacaaagcta aatgtgagca gaccaggcat gcctctgcta aatgaggatg cccacaccaa    2820
acatgcccaa gatcttcaag tataatttta ttatatagat tcgctatgtg ttgacatgtt    2880
tttatagtga acctggattt tacaaaccct cctggtttgc cacctgcttc tggcaccata    2940
cttgaggctt aggcacgtga taaggagca tgcctgtttc ccccttatt ttttttaaag      3000 aaaagcacca tgttacatca ttaatcatgc atatcagtgt agtttagatc cgatgtagag    3060
acaataatct tatctctttg tctggctgaa agactgtcct ttaaactatc attctaaatg    3120
catttggttt ttgccaggag taaaacatgt cacaagatat ttgttgtcat ttcccaggcg    3180
tggaaggaaa ggaatggaaa gaaaacgagg ggtgaaggct gctgttcctc tctagtcgct    3240
acttgaagtc tacatagctg gggggggggg gggactgtt cacatgggac cggtttcctc     3300
tttgttccta cactggcgcc tctggcaaga aactctccct tctcttcccc ccaagcatat    3360
cttggctgaa aggtcagctc tgaaaagggg cctggccaaa gttactgtag ggaccgtgg     3420 tcatggaact gggtagacaa aagcactcta gcagccactg gagaaggacc ggggctctt    3480 ctctgtgcat ttgccctgga gccctgacca ccgccagctc cctgcatctc cttgctatgg    3540
gttttctgga ccgagccagg caggagttca aaccgaaat gtcttctagg gctaatcagg     3600
taacttcgga cgatttaaag ttgccagatg acgagaaaa cagtagaggc gttggcaacc    3660
tggataagcg cctatcttct aattaaaaca ttcagacggg gcgggggatg cggtggccaa    3720
agcaccataa aacaaaactt ccaagtactg accaactcac tgcaagtttg tgccccgagt    3780
acatctaggt tcagggtct tgtcttcatg ctcccaactg cgggcggatt tttggtccct     3840
tgggactttc agtgcagcgg cgaagagagt tctgcacttg caggctccta atgagggcgc    3900
agtgggcctc gtgtttctgg tgatgcttcc caggttgctg ggggcagcaa gtgtctcaga    3960
gcccattact ggctacattt tacttccacc agaaaccgag ctgcgtccag atttgctctc    4020
agatgcgact tgccgcccgg cacagttccg gggtagtggg ggagtgggcg tgggaaaccg    4080
ggaaacccaa acctggtatc cagtgggggg cgtggccgga cgcagggagt ccccacccct    4140
cccggtaatg accccgcccc cattcgctag tgtgtagccg gcgctctctt tctgccctga    4200
gtcctcagga ccccaagaga gtaagctgtg tttccttaga tcgcgcggac cgctacccgg    4260
caggactgaa agcccagact gtgtcccgca gccgggataa cctggctgac ccgattccgc    4320
ggacaccgct gcagccgcgg ctggagccag ggcgccggtg ccccgcgctc tccccggtct    4380
tgcgctgcgg gggcgcatac cgcctctgtg acttctttgc gggccaggga cggagaagga    4440
gtctgtgcct gagaactggg ctctgtgccc agcgcgaggt gcagatg                  4487
```

<210> SEQ ID NO 33
<211> LENGTH: 38
<212> TYPE: DNA
<213> ORGANISM: Artificial Sequence
<220> FEATURE:
<223> OTHER INFORMATION: Description of Artificial Sequence: primer VEF

<400> SEQUENCE: 33

```
acacgcctcg agaaatgtgc tgtctttaga agccactg                              38
```

<210> SEQ ID NO 34
<211> LENGTH: 40

```
<212> TYPE: DNA
<213> ORGANISM: Artificial Sequence
<220> FEATURE:
<223> OTHER INFORMATION: Description of Artificial Sequence: primer VER

<400> SEQUENCE: 34
acacgcgtcg acgatccaat aggaaagccc ttccataaac                              40

<210> SEQ ID NO 35
<211> LENGTH: 511
<212> TYPE: DNA
<213> ORGANISM: Mus sp.

<400> SEQUENCE: 35
aaatgtgctg tctttagaag ccactgcctc agcttctgca gctcagatac caaaggaagt        60
ctggtacaca gcatgataaa agacaatggg acggggtcac agtggctccc gtccctttca       120
ggggtatgga gacgagctgt agagagatgt ctccagggag ttttcattaa tcagcaattt       180
agtcagatct gtgcatccta tgctttacaa gaaatgtcag tgggcctgag atcatcagat       240
ggaggttcat cgggtttcaa tgtcccgtat ccttttgtaa gaccttgaag ttggcaacgc       300
aggaaaacag gaactccacc ctggtgccgt gaattgcaga gctgttgtgt tggtttgtga       360
ccatctgccc attcttcctg ttatgacaga gcttgtgaac tttaactggg actggggcaa       420
agtcaatccc acctttatac aatgaattgc tgaagaggcc ttttaaaact tggagtgtgc       480
attgtttatg gaagggcttt cctattggat c                                     511

<210> SEQ ID NO 36
<211> LENGTH: 34
<212> TYPE: DNA
<213> ORGANISM: Artificial Sequence
<220> FEATURE:
<223> OTHER INFORMATION: Description of Artificial Sequence: primer
      GL3B-Forward

<400> SEQUENCE: 36
gtacttaatt aagcttggta cccggggcgg ccgc                                   34

<210> SEQ ID NO 37
<211> LENGTH: 34
<212> TYPE: DNA
<213> ORGANISM: Artificial Sequence
<220> FEATURE:
<223> OTHER INFORMATION: Description of Artificial Sequence: primer
      GL3B-Reverse

<400> SEQUENCE: 37
agctgcggcc gccccgggta ccaagcttaa ttaa                                   34

<210> SEQ ID NO 38
<211> LENGTH: 26
<212> TYPE: DNA
<213> ORGANISM: Artificial Sequence
<220> FEATURE:
<223> OTHER INFORMATION: Description of Artificial Sequence: primer T2
      Forward

<400> SEQUENCE: 38
tatcaacact cgggaggctg agggag                                            26

<210> SEQ ID NO 39
<211> LENGTH: 41
<212> TYPE: DNA
<213> ORGANISM: Artificial Sequence
```

```
<220> FEATURE:
<223> OTHER INFORMATION: Description of Artificial Sequence: primer T2
      Reverse

<400> SEQUENCE: 39
ataagaatgc ggccgcactt ccccagatct ccccatccag c                           41

<210> SEQ ID NO 40
<211> LENGTH: 7093
<212> TYPE: DNA
<213> ORGANISM: Mus sp.
<220> FEATURE:
<221> NAME/KEY: base_polymorphism
<222> LOCATION: 3617
<223> OTHER INFORMATION: /note = "'n' represents an a or g or t or c
      polymorphism at this position

<400> SEQUENCE: 40
ggtaccaaag catagaacta cagatccgct ctctgcctgt accaccctct ggcatttaat       60
cacacaatgc ttggttttgt tcttcaactt ttcctgttat gatgcagtcc ctggcttgtg      120
taactatgag cttcaaaagc aaagaacgca tcatctattt ttgtgtctct tcttccaagg      180
acttagtgta tcacttactg gctaaatgct tgagacaaaa acagggatta atgaagaaga      240
aagagaaaga aaaggaaggg aaagtgccca caattactga cagggtttca gtaaagcagt      300
ctagagggtc aggtattttc catagccatg ccccagagtg ggtgttgcca ctttagctgc      360
cctggtctgg ctgaaggcca ggacttgatt gttgatggcc cttcctttgc tgctagtcac      420
tgttaagtac tgcagattta cagaaagctt catggaggtc tgtaagaagc cagaggtgat      480
aacaccaaga tttagagcca ctgaccagca gaatgcagaa tgtccaggct atgatccagg      540
ttgtagatcc tgatctgact actcaagact ggttgaaggc aaggttcact tggattcact      600
ctatttgcca gcagatgttt taaatccatc atatatatat atatatctcc attactttag      660
gacagtggtt ctcagccttc ctaatgctgt agccctttaa tagagttcct catattgtga      720
ttgtaaaaat tattttgttg ctacttcatg actaattttg ctactgtgaa agggtcattt      780
taccccaggc tgttgagacc cacatgttgg gaaccactac tttagaaggc attggggttg      840
gagaagaaca tgaagaatag agtaacagtg gtcagttttg gttcattata tcacagaaac      900 attcactttta aggtttcagc atgtttgttg tgtatatgtg attgtgtaaa gacttccacca     960 ggtctttctt taatcaccat acctaacatc ttcaccactc catatccatc agcttcacct     1020
tgtactctag catttgggca ttcatcctgt accagggcag gcatccattc ttttgcaact     1080
cacattgttt cctagttttg attattacca acaatgcttc tagaccatga attttggtct     1140
ttgacttttg cttggtaaac atcataaaac aatccagtgg tggtggtggt gccgctgctg     1200
ctggtggtgg tggtaaagca ggaagccata aagtgccttt attcaatctg tatttgatac     1260
aaattgttat ttcttcccat gtaaaagata tggcatctga agtgtagagg tctgaattca     1320
aacctcacat caccagatag tatattacag actcaacaaa taatacacgg ctttgcctga     1380
cttcaaagcc ctgttcttga cgtaagtata tgagtaacaa tggtagcacc ttagtttttta    1440 tcagttcact aaatatttat ataagaccta ctatgaaggg agatagaagg gtatgaggtg     1500
gggtcatggg aataggaaaa cggtggaagg gagaaggaga attaacaaaa gctaattatg     1560
tttgaaaatg ccacaatgaa acctaattta caaaagaacc actatatgac cttcacagtg     1620
tgtgctaagt cttggagatt tagtggtgaa gaagtcaggt gtgtttccaa tctcatggag     1680
gatgtaatca gttagagagc acaggagcac ataaaaagat aggcaaaaat gtatgattag     1740
```

-continued

```
taccatgtaa gatatgaagg ggaacacagg aaactagtgg ggagacctaa tttagtttga    1800
gtggtcttca aagacccttt agaagctgag aactaaagac agcaagcaag gtgagggcag    1860
catctccacc tttccagtgg aatgagcaac ttagggtata cagctgattc ccacattgtc    1920
aacaaggctc ttcagagact agagatgcac taatgatgac catacccagc ttttaaggaa    1980
ggtttctgag catgtccaag caccctacac taggcattgg aaatcaacat gtccagagat    2040
ggaagtgaca gtcagtaagc caaccctttt caaaacttcc aaagctatta ctcgtcaact    2100
ctccagacat atgggccccg agtgtgttgg gaagctctca ttattgttct ttgattggtt    2160
ctctacattc cgagatccaa ggagcagtta tctcaggtag aggatcgtgg aatgtctgcc    2220
catgattaac ttcaatttat acctgtaagt tataccacat cctaaacacg ctgatgtccc    2280
agagaacatt ttgaccagct gctaacaaaa cccaggagca tttagaaaaa aactgagtca    2340
cccaccgttc tggataatga tggagagaaa caaatgggat tattcttaca gagtatgaaa    2400
gttacataat tttcctggat aatggagaat taattaaaca tcagcatctt ttctggactg    2460
cagagggaag acagaggtga agccaatctt tccgggaaat ggaggaggaa agaatttgac    2520
tactatttgg gggttaacaa tacatcttac tagcatggca aaggaaactg ggctgctttt    2580
cagagtaagc caccccagta gatgctgcaa ggctgtgctt tcatcccagg agaaagtcaa    2640
cagggccagg catgccagaa catgcccata atgtaaccac ttaggctgag gcagaaagat    2700
caaaaatccc aggccagctt agtttgtgta acaagacctt tgctcaaaca aagatttaca    2760
aaacaaacaa gcaaacaaac aaatataaaa aaggagaaga aaataactgc caggggaggc    2820
tgtgagcaat gaagacttga tgagtgacca tctcgcacag tggacgcttg tgtctagaag    2880
gtaagggctt ggcaatgttt cccaggtttt ccattcctgg tttatatggc ttgaggccag    2940
tggacttcac aatgtctcag cttccaggtc tttatacaga gcatattagc cacatgtggt    3000
agcttgtgcc tgtaatgctg gcacttgaga gaccaagaca ggaggattgc cacaagtctc    3060
catccagcct aggtgctgtg tcactctgtc tcacccctga cccagtccca cccaacatca    3120
aacaggctat cactgtgaca ctggtactga gtcagaatca cccagattaa agattctggg    3180
agatcagtcc tggggatgcg ggaagtgaga ccagttattt aataattctt atactcatga    3240
gatgatggat ccagatgaga aattgtaaaa attttaggtt ttataattga agaaataggt    3300
ggtttcttca ggttacatct ctccactgtt ggtcatttca gctaaggtca ctccccattg    3360
attcctgtga ggctctcaca tcccaggtct ctgggacttt ctagaggttc ccgctgcttc    3420
ccagccctga aaatgcgtat ttctattcat tctcctggca ttctgggctt ctctcctgtc    3480
ccccgcccca cccaacacct gatcctgccc cctttctctc cccttctct ctctaaacca    3540 ggtccctccc tccctctgct tcccatgatt attttgttcc ctcctctaaa tgagtctgaa    3600
gcatcctcac ttggacnttc cttcttgtta aacttcatat ggtctgtgag ttgtatcatg    3660
ggtattctgt acttttttgg ctaatgtttc acttatcagt gagtgcaaac caggcatatc    3720
cttttgagtt tgggttacct cactcaggat gatattttct agttctatcc attcgcctgc    3780
aaaattcatg atgtcctaat ttttagtagc tgaatagtat tccattgtgt aaatgaacca    3840
tattttctgc atctgttctt cagctgaggg aaatctgggt tgtttccagc ttctaggtat    3900
tataaataag gttgctatga acatagtgga acacatatcc ttgaggtatg gtagagcatc    3960
ttttgggtat atatccagga gtggatagtt gggttttcag gtagaactat ttccaatttt    4020
ctaaggaacc accagattga ttttttagata gacagggccc ctagtggaga gatgggccca    4080
aacacctacc ttcaaaaatt tggtccagaa ttgttcctct ctaaaagaaa tgcagggaca    4140
```

-continued

```
aaaatgaaac agagactgac caacccaact taggatccat cctatgggca agcaccaaac    4200
ccagactcta ttattgatgc catgttgtgc ttgcagacag gagcttagca tggctgtcct    4260
ctgagacact ctatcagcag ctgactggga cagatgcaga tgccaaccct tgaactgagg    4320
tccaggaccc ctatggaaga attaggggaa ggtttgaagg agctgaaggg gatggcaacc    4380
ccataggaaa acaagtgtc aactaaccct cagagctccc agagactaag ccaccaacta    4440
aagagcatac atgggctggt tgtggtccc tggcagagga ctgccttgtc tggcctcagt    4500
aggagaggat gtgcctaatc ctctagagac ttgatgcccc aggaagggg acaaggaggg    4560 gacaaggtgg ggattggtgt ggggtagtgg gggttgggg tggggtggg gatgtgaatg    4620 ggtgagtgag ggaggaatg agtgagtggg tggtacagca tcctctcaga ggcaaagggg    4680
aaggggagtg gataacaaac tctgggagca gggacgggga aggagggcaa catttgtaat    4740
taaataaata aataatttta ataaaaaaaa tgaagaaaca ggataacttg ggaatggtta    4800
cagcagggct gggattagaa cccaaaaagt ttattctgag actcttttcc aataccaagc    4860 ttaaagttttt cttcagaatt ctatagaatg ccttttttggc agaagttctt tggactttaa    4920
taaagaacat attgaagaga tgaaagaag cttactaaga tctaatgaaa atcaagatgc    4980
taggcacagt gccagatact ttaacatagt aatatgactc tttagagttt tgagacaggg    5040
cctcatatag tttatgatga attcactgtt ttgtcaaaga tgaccttgaa ctcttaatcc    5100
attcccaaag tgttgttgtc atatgtttgc accactcctg gcttcatagt gttttttaaaa    5160 cacccatgga gagtcgggtg tgaagatcca cacgtctaac ctcagcatct ggtgaatcaa    5220
ggcaggaggg cgggtggttg caggctggct ataatatcta agtttcagtt agtaagggct    5280
gcataatgaa acactgtctt aaacacaaaa ccaaaaccca tgaaggagat actattgcca    5340
tttaaaagtc tctggaatgg aaatagctat cataatctta cctctgagcc agtgtctgcc    5400
ctcaggtgtg cctgaggact gaacagggct atgcactcct caggttggaa acattactag    5460
tcctcagtgt ctgctcttga cctgttaaca gctgagtcag ggtctgccct cagctgtgcc    5520
tgaggacaga gctgagctat ctacccctgc agattggaag cattacaggc actcaagatc    5580
agccctgaag tgataaaacc taaggcagaa atccaccaag actagcagtg cctccgtgtc    5640
tcttcctgtg gctggtggga aagagagggg cagtccttcc ttgatgcaag gtcgtgtgtc    5700
tagtggcacg cttccttcat tcccagtgag agcaagtgat cacctgggta aggaaggttc    5760
aggtgcctga gctcgctgga gaattcatca ctcatccatc actctgctcc tgtagacata    5820
atcacttctg ttgggtcttt atagagatga tttataactt tgttgtttat agtttttatg    5880
aatgtgtgta ttcatttagg tcacatggga ggtacacatt ttcaggtgtc tgtctttcca    5940
tcacacgggc tttgaattaa actcagtctt ggttttaccg gctgagccat ctcacctgcc    6000 tgattatttta aaaatctccg gagtaatcca ggagtgtggt ttatgattgt agtatcaaca    6060
ctcgggaggc tgagggagca tcgttatcat gagctccagg ctagttccag gcttgcctaa    6120
gctgtagagc aagtcactct cttaaaaagt gcctctccca tattttgta tataatttgc    6180 atctgaaatt ctgtttgcca ataactatga aattattcac attactaaaa tcttcctgtg    6240
ccaagttctc caacgaatta gatcacactc agatgaaatg ctaataaaaa ttaaagctgt    6300
agccagtagc atgcgtatat ttgggctcag ggccaacagg caggcgatct gggtgtaaga    6360
aaataggcta atggctgtgg aatctggtct ctagtggctc cgctgagagc tgacctcaac    6420
cacgctccct caaattgatt gccttccagg ttatgatttc tcatcacagg aaactttgtt    6480
```

| | |
|---|---|
| gcccaattca aaccctgtga gtgaaaacaa aaacaggaga gcaagtgctg ctccccgtgc | 6540 |
| cccaaagccc cttctgtcag ggatcccaaa tgcacccccag agaacagctt agcctgcaag | 6600 |
| ggctggtcct catcgcatac catacatagg tggagggctt gttattcaat tcctggccta | 6660 |
| tgagaggata ccctattgt tcctgaaaat gctgaccaga accttacttg taacaaagat | 6720 |
| ccctctgccc cacaatccag ttaaggcagg agcaggagcc ggagcaggag cagaagataa | 6780 |
| gccttggatg aagggcaaga tggatagggc tcgctctgcc ccaagccctg ctgataccaa | 6840 |
| gtgcctttaa gatacagcct ttcccatcct aatctgcaaa ggaaacagga aaaggaact | 6900 |
| taaccctccc tgtgctcaga cagaaatgag actgttaccg cctgcttctg tggtgtttct | 6960 |
| ccttgccgcc aacttgtaaa caagagcgag tggaccatgc gagcgggaag tcgcaaagtt | 7020 |
| gtgagttgtt gaaagcttcc cagggactca tgctcatctg tggacgctgg atggggagat | 7080 |
| ctggggaagt atg | 7093 |

<210> SEQ ID NO 41
<211> LENGTH: 1659
<212> TYPE: DNA
<213> ORGANISM: Mus sp.

<400> SEQUENCE: 41

| | |
|---|---|
| ctcgaggtcc agtatggctt ctcaaccttc ttggcaagaa ggctgcaggg acgaccagga | 60 |
| agtttgaaac agtcttagaa gaaatgctg gcttagagac aggtggcaat ggggatggg | 120 |
| gagcagtatt ctggtttgca tagaggcaga gtccttccaa gtgctgggaa acaaggcagg | 180 |
| agggcaggga tagagcaaat gatggctctg tatgtgtccc tgttcagttt gcatttaatc | 240 |
| tgagcaaaat ttggcttttg acatctgcaa ctcaaaagaa ggtaattagg caaatgactg | 300 |
| acacatagat atcttaatag tcaaggaatt tttttttttt tttttgaaga gttagcagtc | 360 |
| aggggatggt agaaactgca aaccaatcc gtattctttc ttgagatttt tagacagttg | 420 |
| atgctactag ccacaaaaag agttttaagt gggaggagag taagatgcag gcaccaaggt | 480 |
| gacaggctcc agtctgtag cattagctta cagatgagat tctttacaga gagccaggca | 540 |
| gctgcattgg ctaaagcaga tctgggaggg ggccaggaga tcagctggcg gcactcccag | 600 |
| cctccaggaa aggcaaccct tatttctgga attttaaact gataacccaa ttcccaccag | 660 |
| cctggccagg ctcttcctta gctcacatca caaacacaga aggattgttt tagatggagt | 720 |
| catgcttgat tctttctata cctacttcca agaccaattt tataaagtt tatttaccgc | 780 |
| ccgtgtgtgt gtgtgtgtgt gtgtgtgtgt gtgtgtgtgt gtgtgtgtgc atggtatata | 840 |
| tggatgtcag agtttggttc tctccttctg cagtgtggct cttagagatt gaactcagat | 900 |
| catgagcaag caccttgctg cctgctatgt ccctccagca gtctgaccat gttccttccc | 960 |
| ccaagattgt ggaagctgga ctgaagatca caatctgcca gatgggcaga atctttactc | 1020 |
| tttggcacat ttgttgctga tggggagtga atacccatgg ggacatggct gtcatggtgt | 1080 |
| ggaagtgata gaaatgaaaa catgtatgga tctgtcacag gagctggtga ggctgatggg | 1140 |
| tgtgtgggtg gccactgttt gctctctgct tgtcacagcc tcttgttcag ggcttgatca | 1200 |
| ggcaggtgtg tgtgtgtgtg tgtgtgtgtg tgtgtgtgtg tgtgtgtggt cacacccatc | 1260 |
| tcagcagatc tgtcagcttt cccgcttttg ttagaggggtg atatcatgct tcctgggggg | 1320 |
| agctctggaa gacaatgagc agccactttc ctctagatac aataggcgga gtcaggaagg | 1380 |
| tagtattgac attgctgggg cctaggagct actcactgct cggtgccgt cagatggtga | 1440 |
| accggcgtaa ccttggcaca caggcctggg ctgtacaagg cgtctggctg cagggccaaa | 1500 |

-continued

```
gaggactcca ccctagggac aggagtactt cagacatctg ggaatctggg atgggtttta      1560
aaattcagat cccaatataa aaaacaact cccaaacaaa cagcagcaat taaaaaaaaa       1620
aaaaaaaacc agcctcccaa gtaaaacaat aatggtacc                             1659

<210> SEQ ID NO 42
<211> LENGTH: 4998
<212> TYPE: DNA
<213> ORGANISM: Mus sp.

<400> SEQUENCE: 42
tccacccacc tgtttctcac gtccccggcc ttcctagtta acttcatggt taaagaagcc      60
tcacccgggg agggtgtggt gccacagaag gaagggtgct cccacaagcc ccagtgtct       120 ctgatttagg gagagcacct gagcccagtg agagtcttct ctgtccctca atcggttctg     180
aaattcccca cttgccctcc ttatccaggg acagggctg cccacccat tcaggacagt       240 agtcttaaac tcgtagccaa cagacttttt attgggctgg gagaaagaga tgaggctcct     300
gaagctcagc cgagtgggct ctgattccta cttctcagag gtcgggcagc ccagccaata     360
ctgagcaatg gagcgtgggt agggaggatt cacagagtcc actcgccggg ttctaaggtt     420
gactcggtag tatttgtctg aaagaaagaa tggaaaaagg gttatgtgag attctgcctg    480
atcctgtcca ctggtcccaa gaaggataaa ggctttttct cagaagggaa agtgaacatc    540
caccaagcag ataatgtcac catctacagg ctgtgttcag cacccaggga ccaagacctg    600
caggcaaggc ctagccaaaa ccagtctaag gagtagaaag gggctcccac ctccagagaa    660
gaaatagacg ctctgaatgg gctcgcaggt ggcaggtaca agccagtcca tatcataatc     720
atagttgttg taggttccta gcccactctc ctcgctggag aacaaagaga accagattga     780
acgtgatgaa cgacgggagt tcgagctctg gctgcgtctg tggccacgcc ctcggcgtga    840
acgatagcgc tttcggcttc tacgcttaga cttctgtttt ttggcttggg cagagtggga    900
taaggagcca gtgacgtaga tgcggccggc catagcagcg tccactttcc ctggcacacc    960
atgccagttc cggctgatga attggggttc tctggctcca tctgtaacag ggaagggtt     1020 aatgcacttg gcagattctg ctttgatttt ctccagcaag gttgtctgtc tatctattta     1080
tctatcttta tctatgtatc tatctatata tctatgtatc tatctatcta tcatctacct     1140
acctacttac ctatctatgt atctatctat ctatcatcta cctacctact tacctatcta     1200
cctatttatt tgtttgtttg tttctttga aacaggatct tagcacctac ctatggctgg     1260
tttgcaactc actatgaagc cataactggc ctcttaactc acaaagatcc acttgcctgt     1320
gtctctgagt gctgggatta aaagcatgtg ccactacacc cagctccagt aggaccttta     1380
gaacacattt gctatgcctt gcctaagaca cacaactcag tccccaggcc ccagcctccc     1440
tgtctagagc tttttcccat cctctctcca ctgtatccct tgaatctctg ccccatccga     1500 aaccctcag cgcgcagccc ctccttctgc tgtgttaggc aaagtccaag gtatgggatc     1560
caaatagagc caagcctcat cccccaaaag tcaacagaag caaagtctag ccagagcaaa    1620
cagctcttga tcgatggtgt cacagttcca ggcccctccc ctggaagccc ccactatcac    1680 agccagttt ccagagaaag aagccagcct tgctctccct ccataccaga ggatctgccc     1740
cagaagagga gttcgaaaat gttctcccag ctgtcccgct gaagcaaggc aaagtgctca    1800
aacacggctg acagagagct gccttcgcac tcctcctggc tgggttgctg ctgaaattcg    1860
tactcccagt actgcttccc tgaggagcag aacagctggc atcaggagag atctgaccaa    1920
```

-continued

```
ggcagagagg aatcatggaa tagaacaggg actccaccac ctgccccctt ctcctccacc      1980
ctgagtaccc ttgaagaagt agacccttc ccggccactg taacggtggg caggaagggc       2040
gaacgctgca tcaacattgt ctggtatgcc actgaagcct tcggagatgt ttcggggata      2100
accagggtcc aggaccccat cctcaaagcg ccagtactga ctaccctgaa agacagagat      2160
cagaagggtg aggacatacc gctggccaca gaagcagtcc tatatcctaa actggctgtc     2220
acctgctcct ggagtccctg actgcttgt cttcacagct ccccagcacg tccatggcac      2280
ccttaccttt gcctcagact taggtctggt accttgaaca gtaggtctt ccctgacag       2340 ttgatgcgag tgaaggcagc atcgatgggg ccctcaatgc cccagacatc ttggataagt    2400
ttggggtacc caggcctcac tgccgtctca tctagctcat agcagtactg ccctagaaca    2460
ggggaaactg tgtgagaagc agatgagcct aaggcagatc cgaccgccac cagacctgtc    2520
catagagtca cctcggaagg caaagaggga cccattcttg agatccgtga aggcgtcaaa    2580
gggctttcca ctgcacagtt cttcctctgg aaactcaggg gtcccttgat cagtggtgtc    2640
gggccttagg atctcctcct gttgctccac tttaggcgct ggggtgcttg gctgttcctc    2700
aggatctagg aaggctgtcg gctttagagt gccgtccgtc cgaggattta ggtcaccggg    2760
tggagaggtg ttctcgggtt gcacaccggt gttggtattg ttcttgggct cctccacgta    2820
gtcatagctc caataatcat cctctggcat agtgaacacg tcccccgcg ttactgcagg     2880 cagaacgggg agcagtgagt gtcaggctgt ggagggagcc ccaggccac ccaccagggc    2940 tctgaactca ccttggggct tgcactgctc catgtagtcg gcacagcagc tctgatagta   3000
agtgcaaagc tcgtcacact gacacttctt gctggccatg aaaccctgag tgcagcggcc   3060
cttgcatgac tctatgggag ggaatatcag gtttacagcc caatctaggg cacctgccca   3120
acctgcactt cccctaggtac ccaccaatcc cctcccacac cttggtcagc cagagaaacc  3180
catgccacca gggctagtat gaaaaagggc ctcaggggtg ccatggcagg cctctagccc   3240
agggccttgg caagctgggc gcggagcttc tggaatctcg ctgtcctgcc tgaaaaaaga   3300
agcagactga agaagagttc ctagttccct gggtttctgc cctttatttg ctcatcctct   3360
ggcccagccc cattgccctc ctccaaacac agctgcagca aagggtcaca ttcccagaac   3420
cccagcccca ggagagctgg gaaacagaaa accctcgcca agaccaaagt cagtagggtc   3480
acgggcagga gggataacac gcttagctta gctggggagg tggaaagaag catgtgttgt   3540
caccctctga gccagtcccg ttaatctccc tgagccttac tttttataaa gtgggaccat   3600
ggtgccttgc ctcatcaggt gttgagagat tccgtgagct agaacagaca aaacgtttcg   3660
tgcctggagt agcttccaac tcattcccat aagccgttat cgatttactg tttgatcagg   3720
ctaggtgctt gtcccatcct acccccgct tcgaatctgg atttttgggg caagaagggg    3780
ggttggggga gagctggcaa gcactttggg ggaggttttc ttttcttctc ataaagaac    3840 aaagcttcat ttctggcctc tccttgttct ctctaagctg ggtgttacag cataggaagt   3900
agtgggtcag agtctattct tctttcttta ttttttttag atttatttat tttatgtttt   3960
gtgtataagt gtctgctcac atgtgcatct gtgcaccaca tgcatgtctt gtgtctatgg   4020
aggtcagaag agggctttga atacctggga actggagttt tgaacagtta tgagctgccg   4080
tgtggatgct gagaatcaaa cccaggtcct ctgtaagaac aagtactctt aaaggctgag   4140 ccatcttttcc agtcccagag cccattcctg aggctttcac taatccattg atcctcgggg  4200
gaccaccctg gccacaccctt caatgacctc atttattta aaaaaaaaat ggactcattg    4260
ggcatacttt ctagactcac atactaagtg ggatttctct ataaagaagt gctcactggg   4320
```

```
gtagagtgcc aggttttggg ccaaattcca agcactggca cacttctgaa gccccctccgt    4380 tttctgttct gtaatcacag gcgagcgtgc ctttggtgtc tcttctctat ggaccgcagt    4440
agtctcagcg gcaaaatgaa acactaaatt ttactcccta cagacgcgtg aagcctaagt    4500
ggaaaccggc attaaagggc tttaagaatc tcaactgcga ttctttaacc atccggaggg    4560
gacgtggata catgtagcca gcttgcttcc acattttggg gagccgagcg agcggtagga    4620
aatggaagac agctctttac agccctttct acagcatctt gcacaccacc aagggagac    4680 tggggagagg aggcggagcc aggtgtgggc gtggctggag acctgggta ggcttgcgcc    4740 tgcgtcgggg gcggagcccg tgaaacctag aggcggggcg tcaaatcctt gactctgctg    4800
ctcagaggcg tggttgctgt tgagcatctt agctccgctg tgcttagatt ggagcagcgc    4860
tttgttccgg gcaccggcgt ctctaccctc ccgcgtctgg tccatgcttc tctctcccett    4920 catgcccttc ctaagtcgct gagtcccgga gctgccctcc tccttctgct tctacacttg    4980
tagcccagca cctttacc                                                   4998

<210> SEQ ID NO 43
<211> LENGTH: 11176
<212> TYPE: DNA
<213> ORGANISM: Mus sp.

<400> SEQUENCE: 43
gcagctgggc aaacgttggc gatgccggtg caaagtatat accggtggt tagcagaagc      60 tgagaacttt tagccgaaag ccggctccct aagccgaagc taggcaagta ggggaagaaa    120
aagaaaaaaa aaattccaga gaagcttcca gagcctcctc ctcttccctc ttccttcaaa    180
aggactgcaa gtccgcagtc accctccacc cagcaagagt tagggcctcg aaccccggtc    240
acgctgcctc cgcctcctgc cgaacgtaac gggggacccg tgcgtaaagc gtgacgcgct    300
ggaatcctcc gtctgacgcg gggcacgcac aggccgcagc cctccgccc gccccgcccc    360 tgacgtccgg gcacgttcta ttttggaacg ccgaggccac gttgctaagg gagggggcag    420
cgtggctttg tgattggctg tcgcgcgcag ctttagccaa tcagcgttcc cttcctattt    480
gtagagcgta gctcccttcc ttgcttttttg tggttcttcc cgtgctgggg gtctccaaga    540
ggagagctag gattcttgtc gcgatcggga ctcgttgtca ccccatggtc tgcgaggact    600
tgtgtggacc tggtctgttg tcataagcta gaggcttttg gctgagtgtt agcgcctcta    660
agggggaact gaaggcctca tccttctcag gcacacatat acgtgctcct gagctctaga    720
cactcagtcc ttccgaggtg ttcaaacact agatgagcta gcctacggag aggcagccag    780
gtggtctcta aaaggtctgc cttcccttag ttcccaggct ctgattggcc agggattcag    840
cccttccctc gccacgcccc ctagagtagt taagcctcta ggattccact tgcgggaagg    900 ggggggggggg gggcgtgatg gacgcttctt ggggacgcag atcctatgtc acccccatccc   960 ctgcaagaca gtctgagaga ttctcgctgt cacttttctc tgcctatcag ttcactgaaa   1020
cctgtcagtc tcactgggaa gagacagaca ctcggaaggg atgctctcaa ctcttaggcc   1080
ggtcccccaa caccgttgga actgggatct ccgcctgcgg gagccctcat gcagtggggg   1140 gtgtgttttgt gtgtgagtgg agaggaaggc ttggctaagg cctctccctc tccctccctc   1200
tgtggtgggg gttgggggt tttggctgta tgtgtgtgtg aatgtctgtg gctccatccc    1260
gggagtttgt caccaggttc tgtccagcct cctctcccac ccaccccccc acacctaaga   1320
gtcaccaacc cggggtgtga ttcaccaccc gctggaaccg tgcaacctttt ccccgaggaa   1380
```

```
gaaggaggag gtagaaggca gttgaacaga atctctcatt aaccactgcg tcacggtgta    1440
gtggaagggt gggtgttgtg ctttttgcc tgtgacacac acatccacac ccgctcaccc    1500
tgtgctcact cacagggtcg gtctctctta tctctcttgg gcgtgtgtgt gtcggtggct    1560
ttgtttgtgt gtctacgcct gtgtgtgtat gtctcacccc gtaggagtgc gccggtctcg    1620
gggaaatgcc cggctccttc gtgccaacgg tcaccgcaat cacaaccagc caggatcttc    1680
agtggctcgt gcaacccacc ctcatctctt ccatggccca gtcccagggg cagccactgg    1740
cctcccagcc tccagctgtt gacccttatg acatgccagg aaccagctac tcaaccccag    1800
gcctgagtgc ctacagcact ggcggggcaa gcggaagtgg tgggccttca accagcacaa    1860
ccaccagtgg acctgtgtct gcccgtccag ccagagccag gcctagaaga ccccgagaag    1920
agacagtaag tatgaggcct caggagttgg gatggaggag cctagctagg gatgtgggct    1980
cagtttgtac agtgccttgc tgccatgcat gaagatccct agcacagcat aagccaggag    2040
tggttatgca gacctgtaac cccagctctc agaaggtgga ggcaggagga gcaggagttc    2100
gaggccagcc tgtgctactt atggagtcca gcctgcactg caagagatca ttattttcaa    2160
aagttggcct tgggggggagg tgggtgaggg aagtaagaga aagtgacagt aattttgtca    2220
cttaatagtt ggaggttcct ctgaggcctc aagtctgaag gaactttacc attctggcca    2280
gtgaggagta ggggttatta tttgggggttc aggaggaagg aagttttctt agggctgata    2340
gaggtacccc cagatctcat ggtccttatc tctgactcag cttaccccag aagaagaaga    2400
aaagcgaagg gttcgcagag agcggaacaa gctggctgca gctaagtgca ggaaccgtcg    2460
gagggagctg acagatcgac ttcaggcggt aaggaggagt ctgggggtgt cttgaggccg    2520
tgctgggagc actctgcctt gttcttcccc cgtttctcac tgtgcctgtg tcctaaacga    2580
ggaaaccccc tcttagggaa caggggtcag tataggctga tggagtggct ccatatgcat    2640
gctcagaccc atgcccactt actttcgact gttccccact ttccctgaat atgtccccac    2700
atgtcaccct cctggctttc tctcagccta aggagacaag ctagaggagg taattctctc    2760 accttcttttt cttcactaaa taataatcca ttttgccttc ctgcctccat tttttttttcc    2820 tgagctgggg atctacctgt cgtagttcag ccctcctccc ccaacttgat agcctcaagt    2880
ttcagccctt ggctgagatg ccatcatcct gactggctct ggctggaaac tattttgtgc    2940
taagtcaatt ccttgtctgc tacttcagct atctacagty ctgccgaact tgagctggtg    3000
gcgcccacca agcccacttc tttctctctt ttttacctca gtgcaacccc ccacacacaa    3060
aacttcatgc ctgccccttg aaaccagggt gcgtctctga ctccccgtcg ggaggctgaa    3120
ggagatgggt aacagaacct cattaaaaac aacacataag cattacctac tgactcaaca    3180
aactgtagtg tttttctttt ttcctctcaa aaaattattt cgtttgttta tttattattt    3240
gcttatgttt gagtgagtgc tggtgcacca cagcacacat acgaggtcag agggaaattt    3300
tcatagtttg ttctctcctt ccgtgttgtg ggtgcttgct ggcaatctcc ttcactcagt    3360
gagctacaat gccccttct gcccttaag gcagagtact ccttagtaca gggggaccct    3420
ttcctcggcc tctcaaagtt gagattacaa atgttcacca tcacaccagg cttggagttc    3480
ttgcctatca gtgacgtcca ctcctgccta gcttcttccc aaccatcttt tagtctgatg    3540
gggaaaccga ggcacgagta gcatggtcta ccaggatttc ctcttagggg acggtcccct    3600
cagttgggag ggagctgtcc agcccctgg atcagcagca agaatgtatg agtgtgggt    3660 tgggcgggtg aagctactct gtgtggtcgc tgaccagcaa ttctcctttc tctgtctcct    3720
atgacctggc cctgctggga tccattagga aactgatcag cttgaagagg aaaaggcaga    3780
```

```
gctggagtcg gagatcgccg agctgcaaaa agagaaggaa cgcctggagt ttgtcctggt    3840
ggcccacaaa ccgggctgca agatcccta cgaagagggg ccggggccag gcccgctggc     3900
cgaggtgaga gatttgccag ggtcaacatc cgctaaggaa gacggcttcg gctggctgct    3960
gccgccccct ccaccaccgc ccctgccctt ccagagcagc cgagacgcac cccccaacct    4020
gacggcttct ctctttacac acagtgaagt tcaagtcctc ggcgacccct tccccgttgt    4080
tagcccttcg tacacttcct cgtttgtcct cacctgcccg gaggtctccg cgttcgccgg    4140
cgcccaacgc accagcggca gcgagcagcc gtccgacccg ctgaactcgc cctcccttct    4200
tgctctgtaa actctttaga caaacaaaac aaacaaaccc gcaaggaaca aggaggagga    4260
agatgaggag gagaggggag gaagcagtcc gggggtgtgt gtgtggaccc tttgactctt    4320
ctgtctgacc acctgccgcc tctgccatcg gacatgacgg aaggacctcc tttgtgtttt    4380
gtgctctgtc tctggttttc tgtgcccggg cgagaccgga gagctggtga ctttggggac    4440
agggggtggg gcgggatga acacccctcc tgcatatctt tgtcctgtta cttcaaccca    4500
acttctgggg atagatggct gactgggtgg gtagggtggg gtgcaacgcc cacctttggc    4560
gtcttacgtg aggctggagg ggaaagagtg ctgagtgtgg ggtgcagggt ggggttgaggt   4620 cgagctggca tgcacctcca gagagaccca acgaggaaat gacagcaccg tcctgtcctt    4680 cttttcccc acccacccat ccaccctcaa gggtgcaggg tgaccaagat agctctgttt     4740
tgctccctcg ggccttagct gattaactta acatttccaa gaggttacaa cctcctcctg    4800
gacgaattga gcccccgact gagggaagtc gatgccccct ttgggagtct gctaaccca     4860 cttcccgctg attccaaaat gtgaaccct atctgactgc tcagtctttc cctcctggga    4920
aaactggctc aggttggatt ttttttcctcg tctgctacag agccccctcc caactcaggc   4980
ccgctcccac ccctgtgcag tattatgcta tgtccctctc accctcaccc ccaccccagg    5040
cgcccttggc cgtcctcgtt gggccttact ggttttgggc agcaggggc gctgcgacgc     5100 ccatcttgct ggagcgcttt atactgtgaa tgagtggtcg gattgctggg cgcgccggat    5160
gggattgacc cccagccctc caaaactttt cctgggcctc ccttcttcc acttgcttcc     5220 tccctcccct tgacagggag ttagactcga aaggatgacc acgacgcatc ccggtggcct    5280
tcttgctcag gccccagact ttttctctttt aagtccttcg ccttccccag cctaggacgc    5340
caacttctcc ccaccctggg agccccgcat cctctcacag aggtcgaggc aattttcaga    5400
gaagttttca gggctgaggc tttggctccc ctatcctcga tatttgaatc cccaaaatagt   5460 ttttggacta gcatacttaa gaggggctg agttcccact atcccactcc atccaattcc     5520
ttcagtccca aagacgagtt ctgtcccttc cctccagctt tcacctcgtg agaatcccac    5580
gagtcagatt tctatttct aatattgggg agatgggccc taccgcccgt cccccgtgct     5640
gcatggaaca ttccataccc tgtcctgggc cctaggttcc aaacctaatc ccaaccccca    5700 ccccagcta tttatccctt tcctggttcc caaaaagcac ttatatctat tatgtataaa     5760
taaatatatt atatatgagt gtgcgtgtgt gtgcgtgtgc gtgcgtgcgt gcgtgcgtgc    5820
gagcttcctt gttttcaagt gtgctgtgga gttcaaaatc gcttctgggg atttgagtca    5880
gactttctgg ctgtccctt ttgtcacttt tttgttgttg tctcggctcc tctggctgtt     5940
ggagacagtc ccggcctctc cctttatcct ttctcaagtc tgtctcgctc agaccacttc    6000
caacatgtct ccactctcaa tgactctgat ctccggtctg tctgttaatt ctggatttgt    6060
cggggacatg caatttttact tctgtaagta agtgtgactg ggtggtagat tttttacaat   6120
```

```
ctatatcgtt gagaattctg ggtggaaatg tctgatcagg agaagggcct gccactgccg    6180
accacaattc attgactcca tagccctcac ccaggctgta tttgtgattt ttttcatttt    6240 gttttttgt attttgcacc tgaccccggg ggtgctgggg cagtctatca ctgggcagct     6300
cccctccccc ccttggttct gcactgtcgc aataaaaag cttttaaaaa actgtatcct    6360
tcaggtcaaa gtgtctgttt tccctggaca tctactacat ggcttccttt cagaaaaacg    6420
gagtttggat tgctagggaa gtcttgctgg cacttagtgg gacgcctaac gaatcagaac    6480
ctacaacggg actaaaagga agtggagact tgctaggttt tcccatgttc ccaggctggg    6540
ccacctactt gaaaaaataa ggggcggaaa agtgtaaggt accaaatttg gtgaagggtc    6600
tgggagaatt tcatgatcgg aaagaatttt attccacctg ggtgtgcaat gaactttcag    6660
caacagttaa gggcaagggt gtaaaagctg gcacaacttt gtaaatccta gcatttgaga    6720
ggtggaggca aggggatcaa ctggtggagt tcagtgtcat gtggatcgta gataccaagc    6780
gcaaagatct gctatgggga gagggcttgg tacaccaggg gagccagaag tttcgtggtg    6840
agggtagtgg agggcaagtg gagagtgaga gttagcctca gggagattct acaggcaatg    6900
atgcagagtt cagacgctcc ctttgaaagc actagagagc cgcagcaggt tttgagcaga    6960
gaaggttaga gttaggtggt ctcttctagc ccatcccagg ctgaggagga cgctgagggt    7020
ttcaagaagg atcgagaatg gaaagcagag gagaagaagg atccaagagg catggaggag    7080
gcagaacaca tttctcttct ttaatagcaa gcctggaaag gataacttgc tgcaggagga    7140
gatgctcacc agtcggtggg tctagggggt tcttggaaaa gagaaggcat ttgctcaagc    7200
ctcggttccc ccattctcgc tcttctgtca gcttgtcttc cattaagtgt gtgtctcaag    7260
gccaccctgc tcaggactcc ttgtgagacg accttctatg ctcgagttca ttaaaaacac    7320
aattgcctgg tgccgtgctc tctccactgg ctcagttacc tcaaaagacc agggctaaag    7380
gtgtgatcac aactctatcc ccattactgc tccaacgcag agacaggact gagccggagt    7440
gaacaaatga acaaaaatga ctaataatgc atgcgtgatt aaatacataa aagagcagat    7500
gactggatga gcaaatcgtt taaggagaga cagcaagatc ctagaatttt ggagactaat    7560
ttaaatccat ctttgagatg catttggtcg gaaattcctg ggaggaaaaa aagtgtaaat    7620
atgaagagag aataaatgag aatagggggtg gcttcagaga ggttaactgc gcgctggtcg    7680
cttttgtaca agaatgtgaa ttgcagggag caaaatggga tagatactcc cgcccgaaag    7740
gtggaattga accactctgt cgctaaacag ctacaggttt gaagcctgca ccccagacca    7800
ctgaggatca tccgggcgaa aggagctatt ttcagttagt tatataaagg cgagatacta    7860
ctacttttta cacttatggt cattatttgt ggtatacagt agataattaa tttcaatggt    7920
ttcgaacatt ttttttcact ttttcttgtg aacatgtgtt tcctcagtaa agtgttccgt    7980
gaatgactct actaactaaa agtaagtag cttcatttgc atagcgcctt gcattttggg     8040
aagcagcgcc taaagtgcct gtctccctaa ctaaaagcag aattttttgc aaagtgaaaa    8100
gtcagtttta tttttgtttg tttgtttgct tgtttgtttt taatggaaaa acttctcacg    8160
cggcccattc gtagcagaat tcgagatttt ctgcaagcga aagcaagac tttcgtaggg    8220 tctgacggca cgcggccgca gagcgacacc tgccgttgct ttatagaact gcaagtatgt    8280
agggaatcta ctgagtccct aggtgatgga gttgacaacc aactccccctt gagtttagac    8340 gctaaaaacc atccctttt atatttatgt gattagccca gggaaactaa ggctcagaca    8400
tggataatac cacagccgag ttcttgtagc ccaactccct aggggaaatg aaacctacag    8460
ttgtggtttt aatatgcttg gcccagggc agtggcccta ttggcaggag tggccttatt     8520
```

```
agcggaggtg taccttgtta gagaagtgtg tcacttggag gcgaggtttt gaggtacgta    8580
tgctcaagtc tggccagtgt gatcctggct gtctgcagaa cgtggtctcc ttctggctgc    8640
cttcggatca aggtgtagaa ctctcagctc cttctccagc accatgtctg cctgcttaat    8700
gctttgcttc tttccatgac gataatgaac tgtgcctctg aaactgtaag tcagcccccc    8760
agttacatgt tttctttat aagagttgca tatatatg tatgtatata tgtatgtata        8820
tatgtatgta tatatatata tatatataaa cagggtctca ctctttagct ctggctggcc    8880
tgaaattcac tatgtagccc aggattgcct gaactttgaa gcaatcttcc tgcctcagcc    8940
tcccaatggt attacaggca tgagtcacaa caagccattt aaatcttatg atgacttata    9000
agaagacaga aaatcagagt tcctttacct agttcacaga tccctacaat ctaacctcgt    9060
tcgctccata aacagcccta ccccaccctc ctggaactgc tttgaggaat gctgcaggct    9120
ctcacaggca cactcctcct tggttaatct cttcagcctg gttgccttcc cccccatgt     9180
ccatgtggcc caaagcctct catcctgttc tcaaatacca ctagctagta aggctccccg    9240
acctgacccg gtttaaatat tagaaaaggg tcactttctc cctgccacag acaaccaaac    9300
caccatatgc ttgtcactta ctacctgact atgaaggtta atagatgtct tcacaacctt    9360
tctctgagcc tcagtttccc cacctgcata atgcatctga dacacagaat tcccagagc    9420
tgtggttctc ctcattccta gtgctgggac cctttaatac atttcctcat gttgtggtga    9480
ccccaccacc accataaaat tatttccatt gatacttcat aactgtaatt ttttctattg    9540
ttatgaatag taatgtaagc atttgtgttt cccagtgatc ttagatgacc ctgtggaaga    9600
gtcattccac cccaaagggg tccccaccac aagttaagaa ttcctgccat agaggaatca    9660
cagggaccat ggattaacac ttgggtcgac ttttgggctg ccttctggga ggcgctagag    9720
ctaatgacag ctacatcaat ttctgaaatt ttgtgtgtgt gtgtgtgtgt gtgtgtgtgt    9780
gtgtgtgtgt gccctgagtc gggtgctgag ataggccagt ggctttagtg ttcctggacc    9840
cattactcac cagaactctc ccctcacctg attctttgat gtgaacacta tgtcttcata    9900
gtggcggtgg caatagcagc aacagtgaac taaattttaa aagtagaact cagctggaga    9960
tacaaatatt gcagttttga agttggggtg gattgtctaa taacttaata acataaccca   10020
gaagagaggc cccttggtct tgcaaacttt atatgcctca gtacagggga acgccagggc   10080
caagaagtgg gagtgggtgg gtaggggagc agggtgggggg gagggtatag gggactttcc   10140
ggatagcatt tgaaatgtaa atgaagaaaa tatctaataa aaatttgaaa aaaaatgtta   10200
ccccagttg gcctggatct cactacctca accagactgg catgtgactc tgctgagatc    10260
tgcctacttc tgcctcctgg gtgcagaaga caattttggg aagttagttc tcttcttcca   10320
tcttgtggat tccagggatt gaactcgggt catcaggctt ggctgcaagt gacttactta   10380
ggtgtctccc agaccctctc ggtttgatta gttagatgct gcacttcatg cctgactttc   10440
gcactatgta gatagagcaa tgtctataac atctcctaca atgatatgta tatcaagagc   10500
caagtgatga gatggctcag tgggtaagag cacagactgc tcttccaaag gtcccgagtt   10560
caaatcccag caatcacata gtggcttcca ttccctctta tggaatgtct gaagactgct   10620
acagtgtact tacatataat aaataaataa atcttaaaaa aaaaaaaccc agccgggcgt   10680
ggtggcgcac gcctttaatc ccagcacttg ggaggcagag gcaggcggat tcctgagttc   10740
gacgccagcc tggtctacag agtgagttcc acgacagcca gaactacaca gagaaaccct   10800
gtctcgaaaa aaaaaagaga gagagggaag tgagagcgca ataatcttaa catttctgtg   10860
```

```
gttgtctttg ctgtagtcta ttctgataag caatgctggc ttgctcccaa ggtaggaagt    10920
aacatttctt tataaaggt atttgctctg ctttatttt ctgttttatt tatggtgctg      10980
aggatggaac ccaggaccct tggcaagcaa ggctagctgt ttaccactga gccatactcc    11040
agccttgcac tgggggattc taggcaaggg ttctaccact gagccacact ccccaccccc    11100
atccctctct ggaagattct aggcagttcc atacctagcc tttgatcttt taagacggtc   11160
ttactagagc tcagtt                                                    11176
```

<210> SEQ ID NO 44
<211> LENGTH: 6000
<212> TYPE: DNA
<213> ORGANISM: Mouse
<220> FEATURE:
<221> NAME/KEY: base_polymorphism
<222> LOCATION: 3172
<223> OTHER INFORMATION: /note = "'n' represents an a or g or t or c polymorphism at this position

<400> SEQUENCE: 44

```
attctggggt tacaagcatg tggtcccttc ccatcccctt cccttctttc acctaggtgt     60
ggagtatatc tcttctccca gccctccctg actctagcca gatcatattg gcttgggaaa    120
tgaaccagat aagcacacgt acatcaactc ttacacctct ctacaaccct ggcaggaggc    180
aacaacactt tccatttcac agatgagaag actgaggctc acagctccgg aaatagtgaa    240
ccagatttgt gctccgtctg ccatgtttc ccattcctcg gtatgggttg ggtggggtg      300 tggggtgtag cagaagccaa ggctcttcac agtgagggat caccaaccag tgacttcaag    360
gaagatgagg ctagttggtt atgcgtatga ctaattctag taatcccact acttgaaaat    420
ttgaggcagg aggattatga attccaagcc agcctgggat acatagtaag accaaaagat    480
gaagataaaa cagaaacaag ctgaaactaa aatgactgag gaggggttag aagagggagt    540
tggagtttcc tgtcttctgg gctgaaggtg tgtctcgcct ccattaaccg gtgctaggcc    600
ccggatgtca ccatggcatt cctgctagat ttttttggtg ttaaacattg ctctcttcaa    660
gagtcataag gacacaggcc acccgaagac gtgacatttg gtatcaagga acagtctcag    720
ctgtcactgt ctctagtgac tcagagctag ggaatcttgc ctagaagtgg agggccagca    780
gcaggactgg tgaactggtg ctgaccaagg tcacactgcc tgtggccttc tcagctctcc    840
tggaggcagg gacagactag agaaagtgtt atcctgcttt gtgctctggt ctagccaact    900
ggccctgggc ttatcccagg ttgctgctta gggcaaacga tggccccagc actcagtata    960
tgactagacc tacctctact gtctggatgg ttttttttaa aacactctct ggggacgtat    1020
tacttccttc ctggtagggg actgccaaga aagcagcgtg gaacttaccc ctgacagaac    1080
agtattgtcc cctgggctct gtctaggatg ttccttaaaa caatccctca gctgggccta    1140
ccctctaagt ctttatcctc agacccagaa gaggacctgg gaggcagcct tacagaaatc    1200
tctagaaatc ccttgtctct ctccccagt tcaccccaat ggctaaattc ctgaaactcc     1260
tgcttctccc ccaaaaccca actgaacgtg tcaggtcctt caggatggcg tcacctgctc    1320
ctagcagtta tgtagcccat cactttagcc ttttgctcac ctgcagacgg gaagtctctt    1380
ccacactgtg ggaaaacagg gtcctgccca aatcagagct tgcccgagga atgtggcaac    1440
cgctagggag tctgtgcccc atgccacttc atgcaggaag catttgggc cagccaatat     1500 ggctgctttg ctggctaatg ctgaaagact ttccccccc acattgcctt tggtatacta    1560
ttaaaagata agaaaaatga cgagaaggaa gaggaagagg aggaagagga ggaagaagaa    1620
```

-continued

```
gatgaggagg aggaggagga ggaggaaaga tcgattttt tggcctttac tttgaaaggg    1680
ctgacatggc tgccccacgc ccctggtttg agaaaggttt caacgtgaag cctaggttct    1740
gcttatttta tgaatctcct gagtgttggg gattccagat gagcattccc atgcccaacc    1800
tgactttatt tcagttctga caatctcctc cctgtctctg aacaagattc tctgaagatg    1860
tcactgacta accaaccacc tagtggattg ctccctagag ccccatgatg ccaggaaaag    1920
attcatcctg gttggtctga cttgcgttag ccagcatgag atcgacaggg ggaacccca    1980 tttctttggg ggtacactgt ttaaataggt tgagagacac agggatctgt ttagaatatt    2040
tcatgtctgc caggcccact acactcccat gtctcctgtc ctgcagtgac ctggggggaga    2100 gacgctgaat agaatctatt ctgggaaatg agccccagg aagagcagga atagtgggat    2160
acttgtcact tcccctcttc tttctagatt ccctgaggtt tcattaagtg acacttacta    2220
ggtccatatc agtgtacgga tgacaccatt gtggaatgtg ttggaggcaa tgtgcagctt    2280
gtatggaatc cagaagtgac ccttcctctg acccagcttc agattgtgtc tctaaaatgc    2340
atgacggagg tagttggccc atccctaccc tgatccgggt tactccaaac ccttcaggcc    2400
aagtttcagt ctttgcatgg ctttagtgct ttggagaggg aaatgtgcag cgtcactgct    2460
ctggctccct gtacaggctc atctgggaac accttataca tatatataca catatactac    2520
atgtatatat acatatacta tacatataca tatcatggct atctcaggat aggaggagga    2580
gtctaaagcc gtgaagtcga aagagctga ttcccctcaa agtctcttca ttttgctcca    2640
aacctcagaa tccttactg agtccctctt ctgtaggccc gtggcctttc ccaagaccac    2700
agaactgtgg ttctcagcct tcctaatgct gagacccttt agtacagttc ctcatgttgt    2760
ggtgaccccc ccagccccc cccacaggca acataaaaat attttgttg ctacttcata    2820 actgtaattt tgttactatt atggatcata atgaactctc tgacatgcag gccatctgat    2880 atgcgaccc tgtgaaaggg ttgttggaca gtccctccaa agggttgagg gttgagaatc    2940
acagctggag gaggtggaga tgagaagggc agcgctttgg gagccttcag tgtctacagc    3000
ctctgttatg ccacgatgag agacagggggc cccctgacag ggagctacat ttggtgttct    3060
tgcggttaga gacagacacg tgagacattt ggtggctttc ctttctgact cctcttagtt    3120
gcttagagca gggatcagga tcaggtgagg aaacccacag gagggctctg gnccagcaaa    3180
catttactaa ctactacttt ccctgctaca agagagccat ccaggagggg actcgggact    3240
agtaatgatg ggcaggaagg gatagcgtga ggagccagct cccttcctca taagatcctc    3300
atactactgc tccattggaa attggggtgc ccaagaggtg ccagcacccc acccagcttc    3360
agtactgtgt gcagagggat gagatagtgg attacactgg ggggggggg caataggaag    3420 attgttgagt tctctttctc agaagtccag cagatctggg tgagggctgg gactggttgg    3480
tccctctctt cccacaggta tcggagcccc ctcttgttcc caggggagcc taggagcagc    3540
tgggccaaag cccaaccagg aattttttcca ggctggttcc tatatccaag ggtgggttag    3600
aggtgggggt tttggagagc tcttaaggaa gacactgagg acatggagaa ggggacttag    3660
tagaaagaga ggggacagag ccacacgggc taagtgtgca agcatagaga aatagccaag    3720
ggttttaggg agaatgggag gacagagtac acccctgaat tctgtttaga agatgaaccg    3780
taagcctagg ctagaactga gggagcctct actcccaccc ttccgagggt tggcggcagc    3840
gctgggcagc tggcctacct accttctga atgctagggt aggtttgaat caccatgccg    3900
gcctggcccg cttctgcccc cattggcacc ctggcttcag ttccctggca acatctctgt    3960
gtgtgtgtgt gtgtgtgaga gagagagatc aggaggaaca agggcctctg tctgcccagc    4020
```

-continued

```
agttgtctct ccttcagggc tctgccagac tacacagtgc atacgtgggt ttccacaggt      4080
cgtctcactc cccgccactg actaactcca gaactccacc cccgttctca gtgccacaaa      4140
tttggtgcca aattctctcc agagaagcct ctctggaaac ttcccagagg atcccattca      4200
ccccagggcc ctagctcctg atgactgcag atcagacaag ggctcagata agcatactcc      4260 ccccccccg taaccccctc cccacatata aacctacagt tatgcttccg aggtcaaaca       4320 cgcaacttt tgggtgtgtg tgtatgtcag aaacacgcaa ttatttggga gctcaaagtc       4380
tgccgcactc aagaatcatc tctcacccccc tttccaagac ccgtgccatt tgagcaagag    4440
ttggggtgtg cataatgtag tcactagggg gcgctcggcc atcacgggga gatcgtaact      4500
tgggcgagcc gagtctgcgt gagggaggac gcgtgtttca atgtgagtgc gtgcatgctg      4560
tgtgtgtgtg tgtagtgtgt gtgtgaggtg ggggagaaag ccagggtca ctctagttgt      4620 ccctatcctc atacgttcct gccagctctc cgccttccaa cccctacttt ctcctatatc      4680
ctgggaaagg gaattgtctt agaccctgtc cgcatataac ctcactctcc tgtctcccct     4740
gattcccaat actctgggat cccagtgtg ttcctgagcc cagtttgaag gggtgcacag      4800
ataattttga ggccgtggac cctggtaagg ggtttagctt tccatttcgc ggtagtggcc      4860
taggggctcc ccgaaaggcg gtgcctggct ccaccagacc gtcccggggg cgggtctggg      4920
cggggcttgg gggtggagct agatttcctc tttttcttcc accgctgtta ccggtgagaa     4980
gcgcagaggc ttggggcagc cgagctgcag cgaggccgcg gcactggggg cgagctgagc     5040
ggcggcagcg gagctctgtc gcgagacgca gcgacaaggc agactattca gcggactcac     5100
cagcccggga gtctgtgctc tgggatttga tattcaaacc tcttaatttt tttttcttaa     5160
actgtattgt tttacgcttt aatttatttt tgcttcctat tcccctctta aatcgtgcca    5220
acggtttgag gaggttggtt cttcactccc tcaaatcact tcggattgtg gaaatcagca     5280
gacgaaagag gtatcaagag ctccagagag aagtcaagga agagagagag agaccggtca    5340
gagagagcgc gctggcgagc gaacagagag agggacaggg gcaaagttga cttgaccttg     5400 cttttgggg tgaccgccag agcgcggcgt gacctccccc ttcgatcttg catcggacca     5460
gtcgcgctga cggacagaca gacagacacc gcccccagcc ccagcgccca cctcctcgcc    5520
ggcgggctgc cgacggtgga cgcggcggcg agccgaggaa ccgaagcccg cgcccggagg    5580
cggggtggag ggggtcgggg ctcgcgggat tgcacggaaa cttttcgtcc aacttctggg     5640
ctcttctcgc tccgtagtag ccgtggtctg cgccgcagga gacaaaccga tcggagctgg   5700
gagaagtgct agctcgggcc tggagaagcc ggggcccgag aagagagggg aggaagagaa     5760
ggaagaggag aggggccgc agtgggcgct cggctctcag gagccgagct catgacgggg   5820
tgaggcggcc gtgtgcgcag acagtgctcc agccgcgcgc gcgcccagg ccccggcccg    5880 ggcctcggtt ccagaaggga gaggagcccc caaggcgcg caagagagcg ggctgcctcg    5940
cagtccgagc cggagaggga gcgcgagccg cgccggcccc ggacggcctc cgaaaccatg    6000
```

<210> SEQ ID NO 45
<211> LENGTH: 37
<212> TYPE: DNA
<213> ORGANISM: Artificial Sequence
<220> FEATURE:
<223> OTHER INFORMATION: Description of Artificial Sequence: primer NOt

<400> SEQUENCE: 45
ataagaatgc ggccgcggtt tcggaggccg tccgggg         37

METHODS AND COMPOSITIONS FOR SCREENING FOR ANGIOGENESIS MODULATING COMPOUNDS

This application is a continuation-in-part of U.S. application Ser. No. 09/465,978, filed 16 Dec. 1999 now U.S. Pat. No. 6,867,348, from which priority is claimed under 35 USC §120, and is herein incorporated by reference in its entirety.

TECHNICAL FIELD

The present invention is in the field of molecular biology and medicine. More specifically, it relates to novel promoters, to expression cassettes, and vector constructs incorporating those promoters that are useful for generating transformed cells and transgenic animals. It further relates to methods of using those transformed cells and transgenic animals, particularly to methods of screening for compounds that modulate angiogenesis.

BACKGROUND

A requirement for cellular inflow of nutrients, outflow of waste products, and gas exchange in most tissues and organs is the establishment of a vascular supply. Several processes for blood vessel development and differentiation have been identified. One such process is termed "vasculogenesis" and takes place in the embryo. This process consists of the in situ differentiation of mesenchymal cells into hemoangioblasts, which are the precursors of both endothelial cells and blood cells. "Angiogenesis" is a second such process and involves the formation of new blood vessels from a preexisting endothelium. This process is required for (i) the development of embryonic vasculature, and (ii) a variety of postnatal processes, including, but not limited to, wound healing, tissue regeneration, and organ regeneration. Further, angiogenesis has been identified as a requirement for solid tumor growth and uncontrolled blood cell proliferation.

Vascular Endothelial Growth Factor (VEGF; also designated as vascular permeability factor (VPF) has been identified as a regulator of normal and pathological angiogenesis. VEGF is a secreted growth factor having the following properties: (i) it is an endothelial cell specific mitogen; (ii) it is angiogenic in vivo and induces vascular permeability; (iii) its expression (and expression of its receptors) has been correlated with vasculogenesis and angiogenesis during embryonic development; and (iv) it is expressed in tumor cells. The VEGF receptor appears to be expressed exclusively in adjacent small blood vessels. VEGF appears to play a crucial role in the vascularization of a wide range of tumors including, but not limited to, breast cancers, ovarian tumors, brain tumors, kidney and bladder carcinomas, adenocarcinomas and malignant gliomas. Tumors have been shown to produce ample amounts of VEGF, which stimulates the proliferation, and migration of endothelial cells (EC's). This is thought to induce tumor vascularization by a paracrine mechanism.

The angiogenic effect of VEGF appears to be mediated by its binding to high affinity cell surface VEGF receptors (VEGFR).

SUMMARY OF THE INVENTION

The present invention relates to transcription control elements derived from angiogenesis-related gene loci, in particular, transcription control elements derived from VEGFR-2, VEGF, and TIE2 gene loci. The present invention relates to methods of use of such transcription control elements, for example, in the construction of expression cassettes, vectors, recombinant cells and transgenic animals.

In one aspect, the present invention includes, but is not limited to, an isolated polynucleotide, and fragments thereof, having at least 80–85%, preferably 85–90%, more preferably 90–95%, and most preferably 98–100% sequence identity to sequence SEQ ID NO:32, SEQ ID NO:40, and/or SEQ ID NO:44. Exemplary fragments include, but are not limited to, polynucleotides having lengths of approximately 55–100, 100–250, 250–500, and 500–1,000. In particular, the present invention relates to recombinant nucleic acid molecules comprising transcription control elements derived from a mouse VEGFR-2, VEGF, and/or Tie-2 gene locus.

One embodiment of the present invention includes an isolated polynucleotide comprising, a polynucleotide having X contiguous nucleotides, wherein (i) the X contiguous nucleotides have at least about 95% identity to Y contiguous nucleotides derived from nucleotides approximately 1 through 3,564 of SEQ ID NO:32 (VEGFR-2; FIGS. 3A–3C), (ii) X equals Y, and (iii) X is greater than or equal to approximately 55. X is typically in the range of approximately 55 to 3,564 nucleotides in length including all integer values in that range. In another embodiment, the invention includes an isolated polynucleotide consisting of a polynucleotide having greater than 80% identity to the sequence presented as SEQ ID NO:32.

In another embodiment of the present invention, an isolated polynucleotide comprises, a polynucleotide having X contiguous nucleotides, wherein (i) the X contiguous nucleotides have at least about 95% identity to Y contiguous nucleotides derived from nucleotides approximately 1 through 3,762 of SEQ ID NO:44 (VEGF, FIGS. 2A–2C), (ii) X equals Y, and (iii) X is greater than or equal to approximately 50. X is typically in the range of approximately 50 to 3,762 nucleotides in length including all integer values in that range. The invention also includes an isolated polynucleotide consisting of a polynucleotide having greater than 80% identity to the sequence presented as SEQ ID NO:44.

In a further embodiment of the invention, an isolated polynucleotide comprises a polynucleotide having X contiguous nucleotides, wherein (A) (i) the X contiguous nucleotides have at least about 95% identity to Y contiguous nucleotides derived from nucleotides approximately 1 through 6,091 of SEQ ID NO:40 (TIE-2, FIGS. 6A–6D), (ii) X equals Y, and (iii) X is greater than or equal to approximately 55, or (B) (i) the X contiguous nucleotides have at least about 90% identity to Y contiguous nucleotides derived from nucleotides approximately 6,091 through 6,560 of SEQ ID NO:40, (ii) X equals Y, and (iii) X is greater than or equal to approximately 250. For polynucleotide (A) X is typically in the range of approximately 55 to 6,091 nucleotides in length including all integer values in that range, or for polynucleotide (B) X is typically in the range of approximately 250 through 469 nucleotides in length including all integer values in that range. The invention also includes an isolated polynucleotide consisting of a polynucleotide having greater than 80% identity to the sequence presented as SEQ ID NO:40.

In another embodiment the invention includes expression cassettes containing the isolated polynucleotide sequences of the present invention wherein the transcription control element(s) is operably linked with a reporter gene of interest, for example, a sequence encoding a light generating protein. Such expression cassettes may be provided in the form of a vector. Exemplary vectors include, but are not limited to procaryotic, eucaryotic, viral vectors, and shuttle vectors. Expression vectors comprise a variety of components described herein, including, but not limited to, origins of replication and selectable markers. Cells, e.g., epithelial cells or tumor cells, and transgenic animals may comprise the polynucleotides of the present invention. Further, cells comprising the polynucleotides of the present invention may be introduced into animals (e.g., wild-type, carrying a genomic modification, and/or transgenic). The transgenic animals of the present invention may, of course, comprise genomic modifications in addition to the polynucleotides of the present invention. In preferred embodiments of the present invention the transgenic animals are transgenic rodents, for example, mice, rats, or guinea pigs.

In another aspect, the present invention describes methods for monitoring expression mediated by a transcription control element, derived from an angiogenesis-related gene locus, in a living, transgenic, non-human animal, for example, a rodent. The methods comprises monitoring the expression of a reporter sequence in a living transgenic animal, where the animal comprises an expression cassette having a transcription control element derived from an angiogenesis-related gene. Such transcription control elements include, but are not limited to, a VEGFR-2-locus-derived sequence, a VEGF-locus-derived sequence, and/or a TIE2-locus-derived sequence. Some exemplary isolated polynucleotide sequences comprising transcription control elements are described above and herein. Expression of the reporter sequence may, for example, be observed to increase during monitoring typically indicating induction mediated by the selected transcription control elements. Alternately, expression of the reporter sequence may be observed to decrease during monitoring typically indicating a repression of expression mediated by the selected transcription control elements. Expression of the reporter sequence may be monitored under a variety of conditions, including, but not limited to, different stages of development of a transgenic embryo, fetus, neonate, or animal; the presence or absence of a analyte; changing environmental factors; and modified genetic backgrounds. Expression may be monitored before, during, and/or after treatment or change of conditions, as well as, such monitoring may be carried out in a single animal or multiple animals. For example, expression mediated by a transcription control element of interest may be monitored in an animal before, during, and after treatment with a selected analyte in order to observe the effect of the analyte on gene expression mediated by the selected transcription control element. Alternatively, control animals may be used for comparison where, for example, the effect of a selected analyte on expression mediated by a selected transcription control element is monitored in groups of treated and untreated animals. Monitoring may include administration of a substrate for the reporter to an animal or cell.

In preferred embodiments of the present invention the sequences encoding light generating protein are sequences encoding a luciferase.

The present invention also includes methods for monitoring expression mediated by transcription control elements, derived from an angiogenesis-related gene locus, in a cell. The methods comprises monitoring the expression of a reporter sequence in a cell, where the cell comprises an expression cassette having a transcription control element derived from an angiogenesis-related gene. Such transcription control elements include, but are not limited to, a VEGFR-2-locus-derived sequence, a VEGF-locus-derived sequence, and/or a TIE2-locus-derived sequence. Some exemplary isolated polynucleotide sequences comprising transcription control elements are described above and herein. Expression of the reporter sequence may be observed to increase during monitoring typically indicating induction mediated by the selected transcription control elements. Alternately, expression of the reporter sequence may be observed to decrease during monitoring typically indicating a repression of expression mediated by the selected transcription control elements. Expression of the reporter sequence may be monitored under a variety of conditions, including, but not limited to, cells derived from animals at different stages of development (for example from a transgenic embryo, fetus, neonate, or animal); cells derived from selected tissue types or organs; the presence or absence of a analyte; changing environmental factors; and modified genetic backgrounds. Expression may be monitored before, during, and/or after treatment or change of conditions. Such monitoring may be carried out in a high-throughput screening format. For example, expression mediated by a transcription control element of interest may be monitored employing a multi-well plate where the cells are treated with different concentrations of analyte and/or combinations of analytes. Monitoring can be carried out before, during, and after treatment with a selected analyte in order to observe the effect of the analyte on gene expression mediated by the selected transcription control element. Alternatively, control cells may be used for comparison where, for example, the effect of a selected analyte on expression mediated by a selected transcription control element is monitored in groups of treated and untreated cells. Monitoring may include administration of a substrate corresponding to the reporter that is employed. A variety of cell types may be employed in the practice of the present invention. Expression cassettes of the present invention may be introduced into a variety of cell-types homologous or heterologous with the source cell of the transcription control element. For example, transcription control elements derived from a mouse gene locus may be introduced into mouse cells, other rodent cells, human cells, avian cells, insect cells, procaryotic and/or other eucaryotic cell types. Cells may, for example, be primary cells, cultured cells, tumor cells, cell-lines, etc.

Particular analytes of interest for use in the methods of the present invention are analytes that are being screened for their effects on expression mediated by transcription control elements derived from angiogenesis-related gene loci.

These and other embodiments of the present invention will readily occur to those of ordinary skill in the art in view of the disclosure herein.

BRIEF DESCRIPTION OF THE DRAWINGS

FIG. 1 depicts PCR conditions for genomic screening for promoters useful in exemplary expression constructs of the present invention.

FIGS. 2A–C depict the nucleotide sequence of the 6 kb promoter region of the VEGF mouse gene (SEQ ID NO:44)

FIGS. 3A–C depict the nucleotide sequence of the 4.5 kb promoter region of the VEGFR-2 mouse gene (SEQ ID NO:32).

FIG. 4 depicts the nucleotide sequence of a VEGFR-2 enhancer region (SEQ ID NO:35).

Figure 6A:
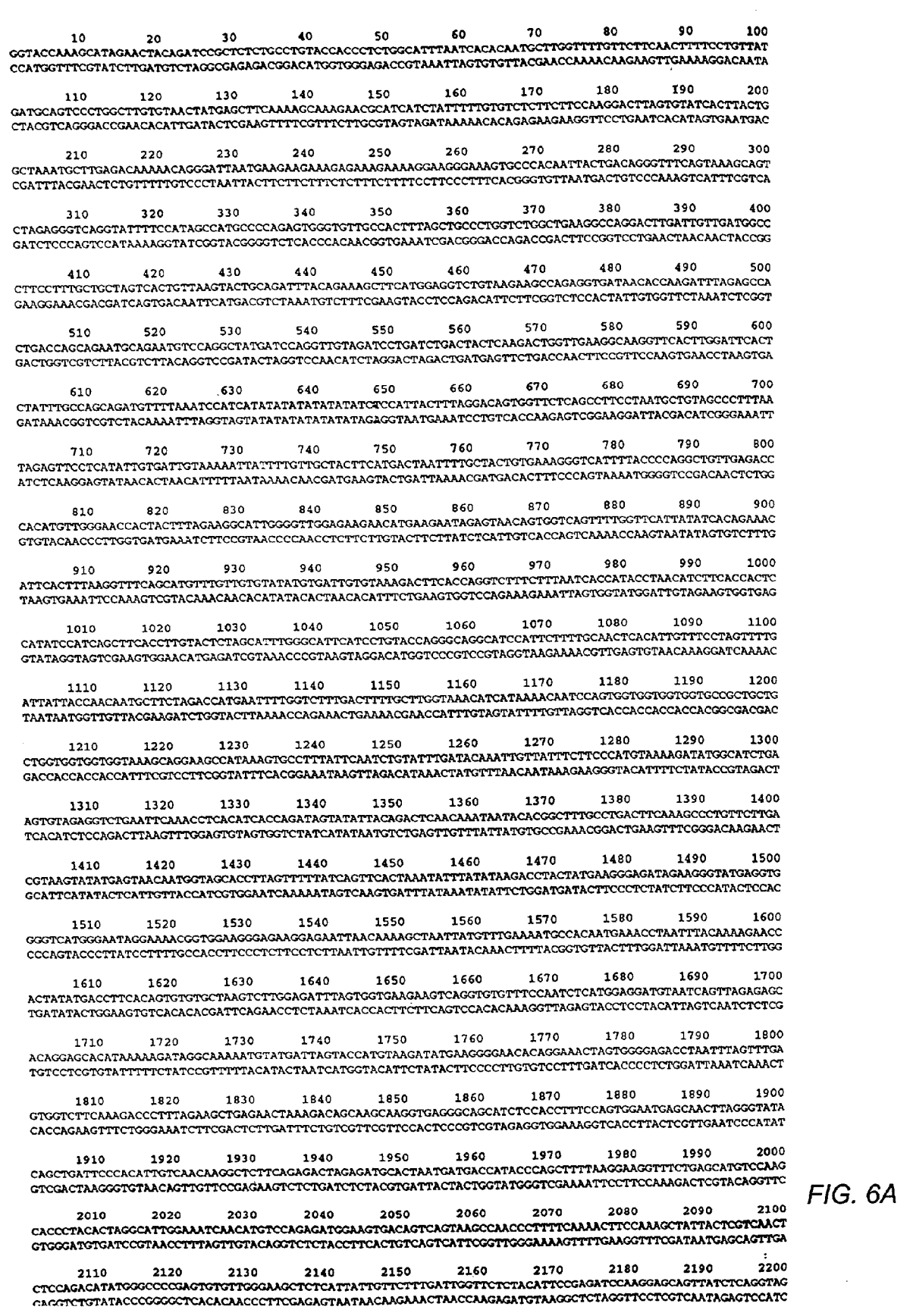
Figure 6B:
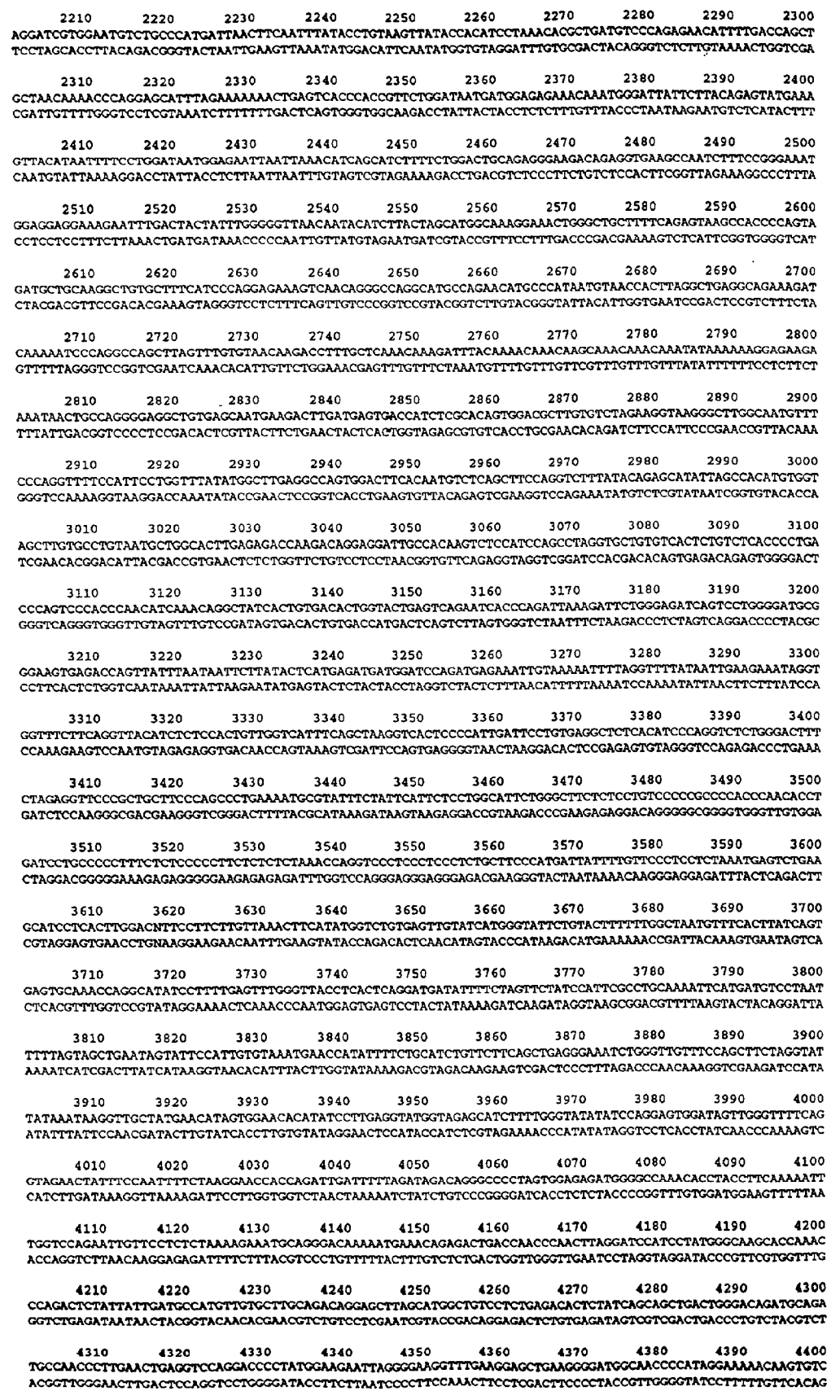

FIGS. 6A–D depicts the nucleotide sequence of the 7.1 kb promoter region of the Tie2 mouse gene (SEQ ID NO:40).

FIG. 7 depicts the nucleotide sequence of a 1.7 kb enhancer region of Tie2 (SEQ ID NO:41).

FIG. 14 is a schematic depicting the vector constructs pTKLG-Fos-KPN and pTKLG-Vn-KPN. pTKLG-Fos-KPN was constructed using pGL3B2-KPN (FIG. 5) and pTKLG-Fos (FIG. 12). See Example 4C(2) below. The vector construct pTKLG-Vn-KPN was constructed using pGL3B2-KPN (FIG. 5) and pTKLG-Vn (FIG. 11). See Example 4C(2) below.

FIG. 17B, transgenic KJ; FIG. 17C, transgenic KG; and FIG. 17D, transgenic KA). The figures show development dependent reduction of luciferase signal in VEGFR2-luc transgenic mice. See Example 7 below.

FIGS. 19C and 19D, ventral and dorsal views, respectively, after treatment).). See Example 9 below.

MODES FOR CARRYING OUT THE INVENTION

Figure 5:
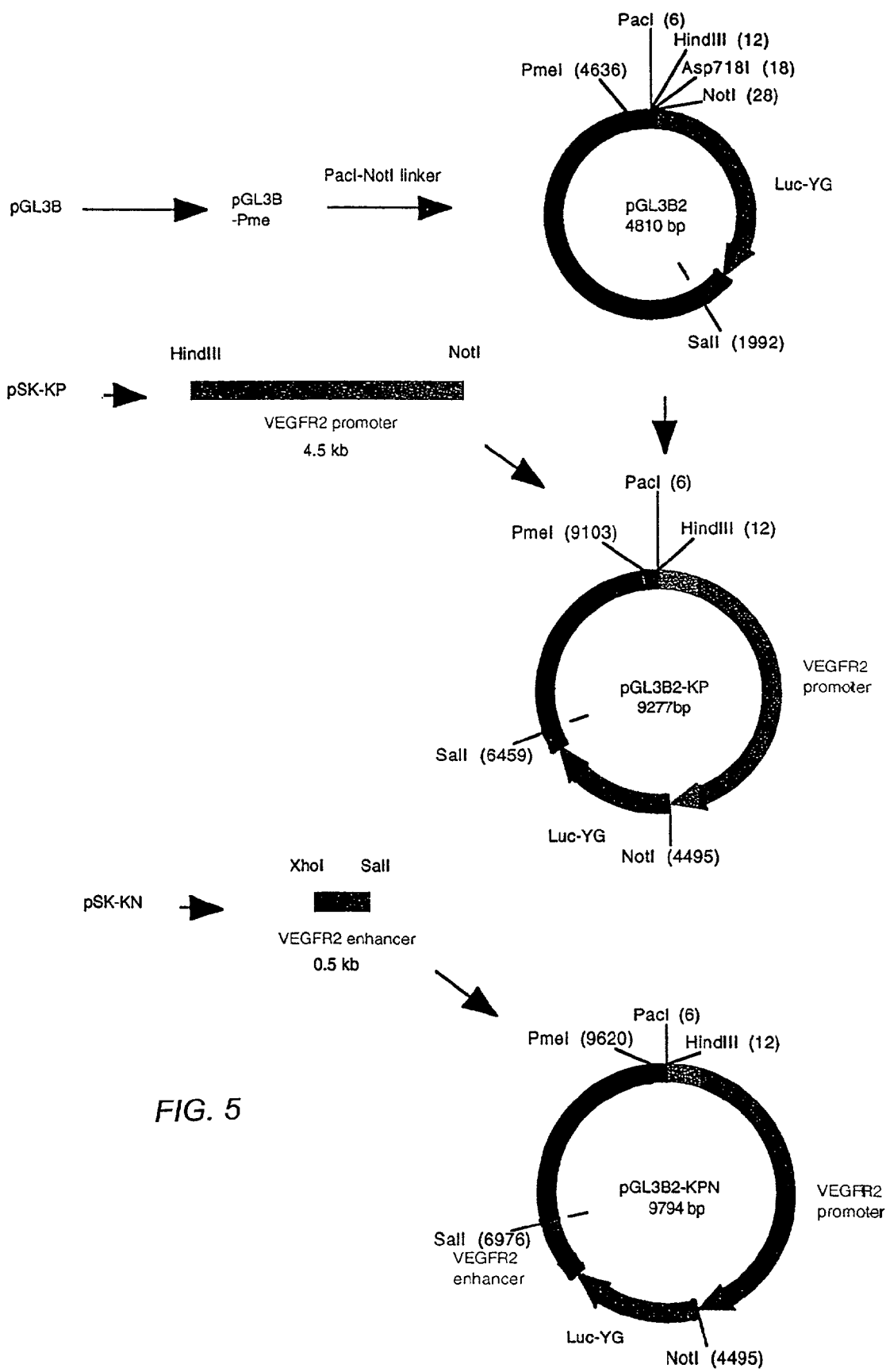
FIG. 5 is a schematic depicting engineering of the pGL3B2-KPN construct. PGL3B (Promega, Madison, Wis.) contains the yellow-green luciferase gene (Luc-YG). The construct contains a 4.5 kb fragment of the VEGFR-2 promoter and a 0.5 kb fragment of the VEGFR-2 enhancer.

Throughout this application, various publications, patents, and published patent applications are referred to by an identifying citation. The disclosures of these publications, patents, and published patent specifications referenced in this application are hereby incorporated by reference into the present disclosure to more fully describe the state of the art to which this invention pertains.

The practice of the present invention will employ, unless otherwise indicated, conventional techniques of molecular biology, microbiology, cell biology and recombinant DNA, which are within the skill of the art. See, e.g., Sambrook, Fritsch, and Maniatis, MOLECULAR CLONING: A LABORATORY MANUAL, 2nd edition (1989); CURRENT PROTOCOLS IN MOLECULAR BIOLOGY, (F. M. Ausubel et al. eds., 1987); the series METHODS IN ENZYMOLOGY (Academic Press, Inc.); PCR 2: A PRACTICAL APPROACH (M. J. McPherson, B. D. Hames and G. R. Taylor eds., 1995) and ANIMAL CELL CULTURE (R. I. Freshney. Ed., 1987).

All publications, patents and patent applications cited herein, whether supra or infra, are hereby incorporated by reference in their entirety.

As used in this specification and the appended claims, the singular forms "a," "an" and "the" include plural references unless the content clearly dictates otherwise. Thus, for example, reference to "an antigen" includes a mixture of two or more such agents.

1. Definitions

As used herein, certain terms will have specific meanings.

The terms "nucleic acid molecule" and "polynucleotide" are used interchangeably to and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term polynucleotide sequence is the alphabetical representation of a polynucleotide molecule. This alphabetical representation can be input into databases in a computer having a central processing unit and used for bioinformatics applications such as functional genomics and homology searching.

A "coding sequence" or a sequence which "encodes" a selected polypeptide, is a nucleic acid molecule which is transcribed (in the case of DNA) and translated (in the case of mRNA) into a polypeptide, for example, in vivo when placed under the control of appropriate regulatory sequences (or "control elements"). The boundaries of the coding sequence are typically determined by a start codon at the 5' (amino) terminus and a translation stop codon at the 3' (carboxy) terminus. A coding sequence can include, but is not limited to, cDNA from viral, procaryotic or eucaryotic mRNA, genomic DNA sequences from viral or procaryotic DNA, and even synthetic DNA sequences. A transcription termination sequence may be located 3' to the coding sequence. Other "control elements" may also be associated with a coding sequence. A DNA sequence encoding a polypeptide can be optimized for expression in a selected cell by using the codons preferred by the selected cell to represent the DNA copy of the desired polypeptide coding sequence. "Encoded by" refers to a nucleic acid sequence which codes for a polypeptide sequence, wherein the polypeptide sequence or a portion thereof contains an amino acid sequence of at least 3 to 5 amino acids, more preferably at least 8 to 10 amino acids, and even more preferably at least 15 to 20 amino acids from a polypeptide encoded by the nucleic acid sequence. Also encompassed are polypeptide sequences, which are immunologically identifiable with a polypeptide encoded by the sequence.

A "transcription factor" as used herein typically refers to a protein (or polypeptide) which affects the transcription, and accordingly the expression, of a specified gene. A transcription factor may refer to a single polypeptide transcription factor, one or more polypeptides acting sequentially or in concert, or a complex of polypeptides.

Typical "control elements" include, but are not limited to, transcription promoters, transcription enhancer elements, cis-acting transcription regulating elements (transcription regulators, e.g., a cis-acting element that affects the transcription of a gene, for example, a region of a promoter with which a transcription factor interacts to induce expression of a gene), transcription initiation signals (e.g., TATA box), basal promoters, transcription termination signals, as well as polyadenylation sequences (located 3' to the translation stop codon), sequences for optimization of initiation of translation (located 5' to the coding sequence), translation enhancing sequences, and translation termination sequences. Transcription promoters can include inducible promoters (where expression of a polynucleotide sequence operably linked to the promoter is induced by an analyte, cofactor, regulatory protein, etc.), repressible promoters (where expression of a polynucleotide sequence operably linked to the promoter is induced by an analyte, cofactor, regulatory protein, etc.), and constitutive promoters.

"Expression enhancing sequences," also referred to as "enhancer sequences" or "enhancers," typically refer to control elements that improve transcription or translation of a polynucleotide relative to the expression level in the absence of such control elements (for example, promoters, promoter enhancers, enhancer elements, and translational enhancers (e.g., Shine and Delagamo sequences)).

The term "modulation" as used herein refers to both inhibition, including partial inhibition, as well as stimulation. Thus, for example, a compound that modulates expression of a reporter sequence may either inhibit that expression, either partially or completely, or stimulate expression of the sequence.

"Purified polynucleotide" refers to a polynucleotide of interest or fragment thereof which is essentially free, e.g., contains less than about 50%, preferably less than about 70%, and more preferably less than about 90%, of the protein with which the polynucleotide is naturally associated. Techniques for purifying polynucleotides of interest are well known in the art and include, for example, disruption of the cell containing the polynucleotide with a chaotropic agent and separation of the polynucleotide(s) and proteins by ion-exchange chromatography, affinity chromatography and sedimentation according to density.

A "heterologous sequence" as used herein is typically refers to either (i) a nucleic acid sequence that is not normally found in the cell or organism of interest, or (ii) a nucleic acid sequence introduced at a genomic site wherein the nucleic acid sequence does not normally occur in nature at that site. For example, a DNA sequence encoding a polypeptide can be obtained from yeast and introduced into a bacterial cell. In this case the yeast DNA sequence is "heterologous" to the native DNA of the bacterial cell. Alternatively, a promoter sequence from a Tie2 gene can be introduced into the genomic location of a fosB gene. In this case the Tie2 promoter sequence is "heterologous" to the native fosB genomic sequence.

A "polypeptide" is used in it broadest sense to refer to a compound of two or more subunit amino acids, amino acid analogs, or other peptidomimetics. The subunits may be linked by peptide bonds or by other bonds, for example ester, ether, etc. As used herein, the term "amino acid" refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is typically called a polypeptide or a protein.

"Operably linked" refers to an arrangement of elements wherein the components so described are configured so as to perform their usual function. Thus, a given promoter that is operably linked to a coding sequence (e.g., a reporter expression cassette) is capable of effecting the expression of the coding sequence when the proper enzymes are present. The promoter or other control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence.

"Recombinant" as used herein to describe a nucleic acid molecule means a polynucleotide of genomic, cDNA, semi-synthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "recombinant" as used with respect to a protein or polypeptide means a polypeptide produced by expression of a recombinant polynucleotide. "Recombinant host cells," "host cells," "cells," "cell lines," "cell cultures," and other such terms denoting procaryotic microorganisms or eucaryotic cell lines cultured as unicellular entities, are used interchangeably, and refer to cells which can be, or have been, used as recipients for recombinant vectors or other transfer DNA, and include the progeny of the original cell which has been transfected. It is understood that the progeny of a single parental cell may not necessarily be completely identical in morphology or in genomic or total DNA complement to the original parent, due to accidental or deliberate mutation. Progeny of the parental cell which are sufficiently similar to the parent to be characterized by the relevant property, such as the presence of a nucleotide sequence encoding a desired peptide, are included in the progeny intended by this definition, and are covered by the above terms.

An "isolated polynucleotide" molecule is a nucleic acid molecule separate and discrete from the whole organism with which the molecule is found in nature; or a nucleic acid molecule devoid, in whole or part, of sequences normally associated with it in nature; or a sequence, as it exists in nature, but having heterologous sequences (as defined below) in association therewith.

Techniques for determining nucleic acid and amino acid "sequence identity" also are known in the art. Typically, such techniques include determining the nucleotide sequence of the mRNA for a gene and/or determining the amino acid sequence encoded thereby, and comparing these sequences to a second nucleotide or amino acid sequence. In general, "identity" refers to an exact nucleotide-to-nucleotide or amino acid-to-amino acid correspondence of two polynucleotides or polypeptide sequences, respectively. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, *Advances in Applied Mathematics* 2:482–489 (1981). This algorithm can be applied to amino acid sequences by using the scoring matrix developed by Dayhoff, *Atlas of Protein Sequences and Structure*, M. O. Dayhoff ed., 5 suppl. 3:353–358, National Biomedical Research Foundation, Washington, D.C., USA, and normalized by Gribskov, *Nucl. Acids Res.* 14(6):6745–6763 (1986). An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the following internet address: http://www.ncbi.nlm.gov/cgi-bin/BLAST. When claiming sequences relative to sequences of the present invention, the range of desired degrees of sequence identity is approximately 80% to 100% and integer values therebetween. Typically the percent identities between the disclosed sequences and the claimed sequences are at least 80–85%, preferably 85–90%, more preferably 90–95%, and most preferably 98–100% sequence identity to the reference sequence (i.e., the sequences of the present invention).

Alternatively, the degree of sequence similarity between polynucleotides can be determined by hybridization of polynucleotides under conditions that form stable duplexes between homologous regions, followed by digestion with single-stranded-specific nuclease(s), and size determination of the digested fragments. Two DNA, or two polypeptide sequences are "substantially homologous" to each other when the sequences exhibit at least about 80–85%, preferably 85–90%, more preferably 90–95%, and most preferably 98–100% sequence identity to the reference sequence over a defined length of the molecules, as determined using the methods above. As used herein, substantially homologous also refers to sequences showing complete identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning,* supra; *Nucleic Acid Hybridization,* supra.

Two nucleic acid fragments are considered to "selectively hybridize" as described herein. The degree of sequence identity between two nucleic acid molecules affects the efficiency and strength of hybridization events between such molecules. A partially identical nucleic acid sequence will at least partially inhibit a completely identical sequence from hybridizing to a target molecule. Inhibition of hybridization of the completely identical sequence can be assessed using hybridization assays that are well known in the art (e.g., Southern blot, Northern blot, solution hybridization, or the like, see Sambrook, et al., *Molecular Cloning: A Laboratory Manual,* Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a target nucleic acid sequence, and then by selection of appropriate conditions the probe and the target sequence "selectively hybridize," or bind, to each other to form a hybrid molecule. A nucleic acid molecule that is capable of hybridizing selectively to a target sequence under "moderately stringent" typically hybridizes under conditions that allow detection of a target nucleic acid sequence of at least about 10–14 nucleotides in length having at least approximately 70% sequence identity with the sequence of the selected nucleic acid probe. Stringent hybridization conditions typically allow detection of target nucleic acid sequences of at least about 10–14 nucleotides in length having a sequence identity of greater than about 90–95% with the sequence of the selected nucleic acid probe. Hybridization conditions useful for probe/target hybridization where the probe and target have a specific degree of sequence identity, can be determined as is known in the art (see, for example, *Nucleic Acid Hybridization: A Practical Approach*, editors B. D. Hames and S. J. Higgins, (1985) Oxford; Washington, D.C.; IRL Press).

With respect to stringency conditions for hybridization, it is well known in the art that numerous equivalent conditions can be employed to establish a particular stringency by varying, for example, the following factors: the length and nature of probe and target sequences, base composition of the various sequences, concentrations of salts and other hybridization solution components, the presence or absence of blocking agents in the hybridization solutions (e.g., formamide, dextran sulfate, and polyethylene glycol), hybridization reaction temperature and time parameters, as well as, varying wash conditions. The selection of a particular set of hybridization conditions is selected following standard methods in the art (see, for example, Sambrook, et al., *Molecular Cloning: A Laboratory Manual*, Second Edition, (1989) Cold Spring Harbor, N.Y.).

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

"Nucleic acid expression vector" or "expression cassette" refers to an assembly that is capable of directing the expression of a sequence or gene of interest. The nucleic acid expression vector includes a promoter that is operably linked to the sequences or gene(s) of interest. Other control elements may be present as well. Expression cassettes described herein may be contained within a plasmid construct. In addition to the components of the expression cassette, the plasmid construct may also include a bacterial origin of replication, one or more selectable markers, a signal which allows the plasmid construct to exist as single-stranded DNA (e.g., a M13 origin of replication), a multiple cloning site, and a "mammalian" origin of replication (e.g., a SV40 or adenovirus origin of replication).

An "expression cassette" comprises any nucleic acid construct capable of directing the expression of a gene/coding sequence of interest. Such cassettes can be constructed into a "vector," "vector construct," "expression vector," or "gene transfer vector," in order to transfer the expression cassette into target cells. Thus, the term includes cloning and expression vehicles, as well as viral vectors.

A variety of "reporter genes" also referred to as "reporter sequences" and "marker sequences," i.e., genes or sequences the expression of which indicates the expression of polynucleotide sequences of interest to which the reporter gene or sequence is operably linked. Preferred are those reporter sequences that produce a protein product that is easily measured, preferably in a routine assay. Suitable reporter genes include, but are not limited to chloramphenicol acetyl transferase (CAT), light generating proteins (e.g., luciferase), and beta-galactosidase. Convenient assays include, but are not limited to calorimetric, fluorimetric and enzymatic assays. In one aspect, reporter genes may be employed that are expressed within the cell and whose extracellular products are directly measured in the intracellular medium, or in an extract of the intracellular medium of a cultured cell line. This provides advantages over using a reporter gene whose product is secreted, since the rate and efficiency of the secretion introduces additional variables that may complicate interpretation of the assay. In a preferred embodiment, the reporter gene is a light generating protein. When using the light generating reporter proteins described herein, expression can be evaluated accurately and non-invasively as described above (see, for example, Contag, P. R., et al., (1998) Nature Med. 4:245–7; Contag, C. H., et al., (1997) Photochem Photobiol. 66:523–31; Contag, C. H., et al., (1995) Mol Microbiol. 18:593–603).

"Luciferase," unless stated otherwise, includes procaryotic and eucaryotic luciferases, as well as variants possessing varied or altered optical properties, such as luciferases that produce different colors of light (e.g., Kajiyama, N., and Nakano, E., *Protein Engineering* 4(6):691–693 (1991)).

"Light-generating" is defined as capable of generating light through a chemical reaction or through the absorption of radiation.

A "light generating protein" or "light-emitting protein" is a protein capable of generating light in the visible spectrum (between approximately 350 nm and 800 nm). Examples include bioluminescent proteins such as luciferases, e.g., bacterial and firefly luciferases, as well as fluorescent proteins such as green fluorescent protein (GFP).

"Light" is defined herein, unless stated otherwise, as electromagnetic radiation having a wavelength of between about 300 nm and about 1100 nm.

"Animal" as used herein typically refers to a non-human mammal, including, without limitation, farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered.

A "transgenic animal" refers to a genetically engineered animal or offspring of genetically engineered animals. A transgenic animal usually contains material from at least one unrelated organism, such as from a virus, plant, or other animal. The "non-human animals" of the invention include vertebrates such as rodents, non-human primates, sheep, dogs, cows, amphibians, birds, fish, insects, reptiles, etc. The term "chimeric animal" is used to refer to animals in which the heterologous gene is found, or in which the heterologous gene is expressed in some but not all cells of the animal.

"Analyte" as used herein refers to any compound or substance whose effects (e.g., induction or repression of a specific promoter) can be evaluated using the test animals and methods of the present invention. Such analytes include, but are not limited to, chemical compounds, pharmaceutical compounds, polypeptides, peptides, polynucleotides, and polynucleotide analogs. Many organizations (e.g., the National Institutes of Health, pharmaceutical and chemical corporations) have large libraries of chemical or biological compounds from natural or synthetic processes, or fermentation broths or extracts. Such compounds/analytes can be employed in the practice of the present invention.

As used herein, the term "positive selection marker" refers to a gene encoding a product that enables only the cells that carry the gene to survive and/or grow under certain conditions. For example, plant and animal cells that express the introduced neomycin resistance (Neo$^r$) gene are resistant to the compound G418. Cells that do not carry the Neo$^r$ gene marker are killed by G418. Other positive selection markers will be known to those of skill in the art. Typically, positive selection markers encode products that can be readily assayed. Thus, positive selection markers can be used to determine whether a particular DNA construct has been introduced into a cell, organ or tissue.

"Negative selection marker" refers to gene encoding a product that can be used to selectively kill and/or inhibit growth of cells under certain conditions. Non-limiting examples of negative selection inserts include a herpes simplex virus (HSV)-thymidine kinase (TK) gene. Cells containing an active HSV-TK gene are incapable of growing in the presence of gangcylovir or similar agents. Thus, depending on the substrate, some gene products can act as either positive or negative selection markers.

The term "homologous recombination" refers to the exchange of DNA fragments between two DNA molecules or chromatids at the site of essentially identical nucleotide sequences. It is understood that substantially homologous sequences can accommodate insertions, deletions, and substitutions in the nucleotide sequence. Thus, linear sequences of nucleotides can be essentially identical even if some of the nucleotide residues do not precisely correspond or align (see, above).

A "knock-out" mutation refers to partial or complete loss of expression of at least a portion the target gene. Examples of knock-out mutations include, but are not limited to, gene-replacement by heterologous sequences, gene disruption by heterologous sequences, and deletion of essential elements of the gene (e.g., promoter region, portions of a coding sequence). A "knock-out" mutation is typically identified by the phenotype generated by the mutation.

A "gene" as used in the context of the present invention is a sequence of nucleotides in a genetic nucleic acid (chromosome, plasmid, etc.) with which a genetic function is associated. A gene is a hereditary unit, for example of an organism, comprising a polynucleotide sequence (e.g., a DNA sequence for mammals) that occupies a specific physical location (a "locus", "gene locus" or "genetic locus") within the genome of an organism. A gene can encode an expressed product, such as a polypeptide or a polynucleotide (e.g., tRNA). Alternatively, a gene may define a genomic location for a particular event/function, such as the binding of proteins and/or nucleic acids (e.g., phage attachment sites), wherein the gene does not encode an expressed product. Typically, a gene includes coding sequences, such as, polypeptide encoding sequences, and non-coding sequences, such as, transcription control elements (e.g., promoter sequences), poly-adenylation sequences, transcriptional regulatory sequences (e.g., enhancer sequences). Many eucaryotic genes have "exons" (coding sequences) interrupted by "introns" (non-coding sequences). In certain cases, a gene may share sequences with another gene(s) (e.g., overlapping genes).

The "native sequence" or "wild-type sequence" of a gene is the polynucleotide sequence that comprises the genetic locus corresponding to the gene, e.g., all regulatory and open-reading frame coding sequences required for expression of a completely functional gene product as they are present in the wild-type genome of an organism. The native sequence of a gene can include, for example, transcriptional promoter sequences, translation enhancing sequences, introns, exons, and poly-A processing signal sites. It is noted that in the general population, wild-type genes may include multiple prevalent versions that contain alterations in sequence relative to each other and yet do not cause a discernible pathological effect. These variations are designated "polymorphisms" or "allelic variations."

By "replacement sequence" is meant a polynucleotide sequence that is substituted for at least a portion of the native or wild-type sequence of a gene.

"Linear vector" or "linearized vector," as used herein, is a vector having two ends. For example, circular vectors, such as plasmids, can be linearized by digestion with a restriction endonuclease that cuts at a single site in the plasmid. Preferably, the expression vectors described herein are linearized such that the ends are not within the sequences of interest.

2.0.0 Detailed Description of the Invention

Before describing the present invention in detail, it is to be understood that this invention is not limited to particular formulations or method parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

2.1.0 General Overview

In one aspect, the present invention relates to novel transcription control elements derived from mouse angiogenesis-related genes, expression cassettes which include those control elements, vector constructs, cells and transgenic animals containing the expression cassettes, and methods of using the cells and transgenic animals containing the expression cassettes, for example, as modeling, screening and/or test systems. Methods of using the control elements, expression cassettes, cells, and transgenic animals of the present invention include, but are not limited to, studies involving angiogenesis, as well as tumor growth and other disease conditions, and methods for screening angiogenesis-modulating. Exemplary transcription control elements useful in the practice of the present invention include those derived from mouse VEGF locus, mouse VEGFR-2 locus and mouse TIE2 locus.

In one embodiment, the present invention relates to (1) novel transcription control elements (e.g., promoters) derived from the mouse VEGF gene locus, the mouse VEGFR-2 receptor gene locus, and the mouse TIE2 gene locus, (2) expression cassettes comprising such transcription control elements operatively linked to genes encoding a gene product, such as, a reporter, a protein, polypeptide, hormone, ribozyme, or antisense RNA, (3) recombinant cells comprising such expression cassettes, (4) methods of screening for therapeutic drugs using such cells (e.g., screening for compounds that modulate angiogenesis mediated by the novel transcription control elements of the present invention), (5) transgenic animals comprising the aforementioned novel transcription control elements, expression cassettes and vector constructs, (6) methods of monitoring angiogenesis using such animals, and (7) methods of screening for therapeutic drugs using such animals (e.g., screening for compounds that modulated angiogenesis mediated by the novel transcription control elements of the present invention).

A variety of transcription control elements are useful in the practice of the present invention, for example, transcription control elements derived from genes or gene locii associated with tumorigenesis or angiogenesis. Thus, an exemplary transcription control element can be one that is associated with proteins induced during tumorigenesis, for instance in the presence of tumor generating compounds or of tumors themselves. In this way, expression of the reporter sequence is induced in the transgenic animals of the present invention when, for example, tumors are present, and progression of the tumor can be evaluated by non-invasive imaging methods using the whole animal. Another exemplary transcription control element (e.g., promoter) is one that is derived from a gene or locus associated with angiogenesis. Because the transcription control element is linked to a reporter such as luciferase, non-invasive monitoring of the progression of angiogenesis is possible. Various forms of the different embodiments of the invention, described herein, may be combined.

Non-invasive imaging and/or detecting of light-emitting conjugates in mammalian subjects was described in U.S. Pat. No. 5,650,135, by Contag, et al., issued 22 Jul. 1997, and herein incorporated by reference. This imaging technology can be used in the practice of the present invention in view of the teachings of the present specification. In the imaging method, the conjugates contain a biocompatible entity and a light-generating moiety. Biocompatible entities include, but are not limited to, small molecules such as cyclic organic molecules; macromolecules such as proteins; microorganisms such as viruses, bacteria, yeast and fungi; eucaryotic cells; all types of pathogens and pathogenic substances; and particles such as beads and liposomes. In another aspect, biocompatible entities may be all or some of the cells that constitute the mammalian subject being imaged, for example, cells carrying the expression cassettes of the present invention expressing a reporter sequence.

Light-emitting capability is conferred on the biocompatible entities by the conjugation of a light-generating moiety. Such moieties include fluorescent molecules, fluorescent proteins, enzymatic reactions which give off photons, and luminescent substances, such as bioluminescent proteins. In the context of the present invention, light emitting capability is typically conferred on target cells by having at least one copy of a light-generating protein, e.g., a luciferase, present. In preferred embodiments, luciferase is operably linked to appropriate control elements that can facilitate expression of a polypeptide having luciferase activity. Substrates of luciferase can be endogenous to the cell or applied to the cell or system (e.g., injection into a transgenic mouse, having cells carrying a luciferase construct, of a suitable substrate for the luciferase, for example, luciferin). The conjugation may involve a chemical coupling step, genetic engineering of a fusion protein, or the transformation of a cell, microorganism or animal to express a light-generating protein.

2.2.0 Promoters

The expression cassettes, vectors, cells and transgenic animals described herein contain a sequence encoding a detectable gene product, e.g., a luciferase gene, operably linked to a transcription control element, e.g., a promoter. The promoter may be from the same species as the transgenic animal (e.g., mouse promoter used in construct to make transgenic mouse) or from a different species (e.g., human promoter used in construct to make transgenic mouse). The promoter can be derived from any gene of interest. In one embodiment of the present invention, the promoter is derived from a gene whose expression is induced during angiogenesis, for example pathogenic angiogenesis like tumor development. Thus, when a tumor begins to develop in a transgenic animal carrying a vector construct of the present invention, the promoter is induced and the animal expresses luciferase, which can then be monitored in vivo.

Exemplary transcription control elements (e.g., promoters) for use in the present invention include, but are not limited to, promoters derived from the angiogenesis-related genes and gene families described below. Those genes and gene families include, but are not limited to the following mouse genes: vascular endothelial growth factor (VEGF); VEGFR-2, also known as Flk 1; and Tie2, also known as Tek.

VEGF is a specific mitogen for EC in vitro and a potent angiogenic factor in vivo. In a tumorigenesis study, it was shown that VEGF was critical for the initial subcutaneous growth of T-47D breast carcinoma cells transplanted into nude mice, whereas other angiogenic factors, such as, bFGF can compensate for the loss of VEGF after the tumors have reached a certain size (Yoshiji, H., et al.,1997 Cancer Research 57: 3924–28). VEGF is a major mediator of aberrant EC proliferation and vascular permeability in a variety of human pathologic situation, such as, tumor angiogenesis, diabetic retinopathy and rheumatoid arthritis (Benjamin LE, et al.,1997 PNAS 94: 8761–66; Soker, S., et al.,1998 Cell 92: 735–745). VEGF is synthesized by tumor cells in vivo and accumulates in nearby blood vessels. Because leaky tumor vessels initiate a cascade of events, which include plasma extravasation and which lead ultimately to angiogenesis and tumor stroma formation, VEGF plays a pivotal role in promoting tumor growth (Dvorak, H. F., et al., 1991 J Exp Med 174:1275–8). VEGF expression was upregulated by hypoxia (Shweiki, D., et al., 1992 Nature 359:843–5). VEGF is also upregulated by overexpression of v-Src oncogene (Mukhopadhyay. D., et al.,1995 Cancer Res. 15: 6161–5), c-SRC (Mukhopadhyay, D., et al., 1995 Nature 375: 577–81), and mutant ras oncogene (Plate, K. H., et al., 1992 Nature 359: 845–8). The tumor suppressor p53 downregulates VEGF expression (Mukhopadhyay. D., et al.,1995 Cancer Res. 15: 6161–5).

A number of cytokines and growth factors, including PGF and TPA (Grugel, S., et al., 1995 J. Biological Chem. 270: 25915–9), EGF, TGF-b, IL-1, IL-6 induce VEGF mRNA expression in certain type of cells (Ferrara, N., et al., 1997 Endocr. Rev. 18: 4–25). Kaposi's sarcoma-associated herpes virus (KSHV) encoded a G-protein-coupled receptor, a homologue of IL-8 receptor, can activate JNK/SAPK and p38MAPK and increase VEGF production, thus causing cell transformation and tumorigenicity (Bais, C., et al., Nature 1998 391:86–9). VEGF overexpression in skin of transgenic mice induces angiogenesis, vascular hyperpermeability and accelerated tumor development (Larcher, F., et al., Oncogene (1998) 17:303–11).

Further angiogenesis-related genes include but are not limited to the following.

VEGF-B (cDNA sequences available on databases) is a mitogen for EC and may be involved in angiogenesis in muscle and heart (Olofsson, B., et al., 1996 Proc Natl Acad Sci USA 93:2576–81). Shown in vitro, binding of VEGF-B to its receptor VEGFR-1 leads to increased expression and activity of urokinase type plasminogen activator and plasminogen activator inhibitor, suggesting a role for VEGF-B in the regulation of extracellular matrix degradation, cell adhesion, and migration (Olofsson, B., et al., 1998 Proc Natl Acad Sci USA 95:11709–14).

VEGF-C (see, e.g., U.S. Pat. No. 5,916,763 and Shima et al., supra) may regulate angiogenesis of lymphatic vasculature, as suggested by the pattern of VEGF-C expression in mouse embryos (Kukk, E., et al., 1996 Development 122:

3829–37). Although VEGF-C is also a ligand for VEGFR-2, the functional significance of this potential interaction is unknown. Overexpression of VEGF-C in the skin of transgenic mice resulted in lymphatic, but not vascular, endothelial proliferation and vessel enlargement, suggesting the major function of VEGF-C is through VEGFR-3 rather than VEGFR-2 (Jeltsch M, et al., 1997 Science 276:1423–5). Shown by the CAM assay, VEGF and VEGF-C are specific angiogenic and lymphangiogenic growth factors, respectively (Oh, S. J., et al., (1997) *Devel. Biol.* 188: 96–109). VEGF-C overexpression in the skin of transgenic mice resulted in lymphatic, but not vascular, endothelial proliferation and vessel enlargement (Jeltsch M, et al., 1997 Science 276:1423–5).

VEGF-D (cDNA sequences available on databases) is a mitogen for EC. Given that VEGF-D can also activate VEGFR-3. it is possible that VEGF-D could be involved in the regulation of growth and/or differentiation of lymphatic endothelium (Achen, M. G., et al., 1998 Proc Natl Acad Sci USA 95: 548–53). VEGF-D is induced by transcription factor c-Fos in mouse (Orlandini, M., 1996 PNAS 93: 11675–80).

VEGFR-1 signaling pathway may regulate normal endothelial cell-cell or cell matrix interactions during vascular development, as suggested by the knockout study (Fong, G. H., et al., 1995 Nature 376: 65–69). Although VEGFR-1 has a higher affinity to VEGF than VEGFR-2, it does not transduce the mitogenic signals of VEGF in ECs (Soker, S., et al.,1998 Cell 92: 735–745). VEGFR-2 (see, e.g., Rönicke et al., Patterson et al., Kappel et al. (1999), supra) appears to be the major transducer of VEGF signals in EC that result in chemotaxis, mitogenicity and gross morphological changes in target cells (Soker, S., et al.,1998 Cell 92: 735–745). The cloning and sequencing of the 4.5 kb VEGFR-2 promoter region is described herein (see Example 2 below).

VEGFR-3 has an essential role in the development of the embryonic cardiovascular system before the emergence of lymphatic vessels, as shown by the knockout study (Dumont, D. J., et al., 1998 Science 282: 946–949). Neuropillin-1 (see, e.g., Soker et al. (1998) *Cell* 92:735–745) is a receptor for VEGF165. It can enhance the binding of VEGF165 to VEGFR-2 and VEGF165 mediated chemotaxis (Soker, S., et al.,1998 Cell 92: 735–745). Neuropillin1 overexpression in transgenic mice resulted in embryonic lethality. The embryos possessed excess capillaries and blood vessels. Dilated vessels and hemorrhage were also observed (Kitsukawa, T., et al., 1995 Development 121: 4309–18).

Thus, in one aspect the present invention relates to the isolation and characterization of the mouse VEFG and VEGFR-2 promoters. This section describes some information related to the VEFG and VEGFR gene families. Alternative names for some of these genes are as follows: VEGF (vascular endothelial growth factor)is also named VPF (vascular permeability factor); VEGFR-1 is also named FLT1; VEGFR-2 is also named KDR/FLK1; and VEGFR-3 is also named FLT4.

VEGF is a homodimeric 45 kDa (monomer 23 kDa) protein. VEGF has five isoforms of which VEGF165 and VEGF121 are the most abundant. Both are ligands for VEGFR-2 as well as VEGFR-1 (Soker, S., et al., JBC 271:5761–67, 1996). VEGF165 is the only VEGF isoform that binds to Neuropillin-1 (Soker, S., et al., Cell 92:735–745, 1998). VEGF is extremely unstable—its half life in circulation is only 3 minutes (Ferrara, N., et al., Nature 380:439–442, 1996; Ferrara, N., et al., Endocr Rev 18:4–25, 1997).

VEGF-B is 43% (aa) identical to VEGF and exists as a homodimer. It can also form heterodimers with VEGF (Olofsson, B., et al., Proc Natl Acad Sci USA 93:2576–81, 1996). VEGF-B is a ligand for VEGFR-1 (Olofsson, B., et al., Proc Natl Acad Sci USA 95:11709–14, 1998).

VEGF-C is 30% (aa) identical to VEGF. The mature VEGF-C is 23 kDa, the precursor protein is 35.8 kDa. VEGF-C is a ligand for VEGFR-3 as well as VEGFR-2. It induces autophosphorylation of both receptors (Joukov, V., et al., EMBO J 15:290–298, 1996).

VEGF-D is 31% (aa) identical to VEGF165 and 48% (aa) identical to VEGF-B. The mature VEGF-D is approximately 22 kDa. VEGF-D is a ligand for VEGFR-3 as well as VEGFR-2. It induces autophosphorylation of both receptors (Achen, M. G., et al., 1998 Proc Natl Acad Sci USA 95:548–53, 1998).

PIGF is 46% identical (aa) to VEGF (Maglione, D., et al., Proc Natl Acad Sci 88:9267–71, 1991) and can form heterodimers with VEGF ((Disalvo, J., et al., JBC 270:7717–23, 1995).

VEGFR-1 is an approximately 180 kDa tyrosine kinase receptor for VEGF-B (Olofsson, B., et al., Proc Natl Acad Sci USA 95:11709–14, 1998) and VEGF (de Vries, C., et al., Science 255:989–91, 1992) and PIGF (Park, J. E., et al., J Biol Chem 269:25646–54, 1994).

VEGFR-2 is an approximately 200 kDa tyrosine kinase receptor for VEGF (Termini, B I, et al., Oncogene September 6(9):1677–83, 1991), VEGF-C (Joukov, V., et al., EMBO J 15:290–298, 1996), and VEGF-D (Achen, M. G., et al., 1998 Proc Natl Acad Sci USA 95:548–53, 1998).

VEGFR-3 is a tyrosine kinase receptor (Pajusola, K., et al., Cancer Res 32:5738–43, 1992) on lymphatic EC for VEGF-C (Dumont, D. J., et al., Science 282:946–949, 1998) and VEGF-D (Achen, M. G., et al., 1998 Proc Natl Acad Sci USA 95:548–53, 1998). VEGFR-3 has a processed mature form of about 125 kDa, and an unprocessed form of about 195 kDa (Achen, M. G., et al., 1998 Proc Natl Acad Sci USA 95:548–53, 1998).

Neuropillin-1 is an approximately 130 kDa receptor tyrosine kinase. It binds VEGF165, but not VEGF121 (Soker, S., et al., Cell 92:735–745, 1998).

Expression of many of these genes has been evaluated in adults. A summary of information relating to expression follows here.

VEGF has an approximately 3.7 kb transcript. It is expressed in multiple human tissues, including heart, skeletal muscle and prostate. In mouse, VEGF is mainly expressed in heart, lung and kidney. The remaining human or mouse tissues, including brain and testis, do not express detectable or significant level of VEGF (Olofsson, B., et al., Proc Natl Acad Sci USA 93:2576–81, 1996). In another study, it was shown that VEGF is highly expressed in epithelial cells of lung alveoli, renal glomeruli and adrenal cortex and in cardiac myocytes (Berse, B., MCB 3:211–20, 1992).

VEGF-B has an approximately 1.4 kb transcript. It is expressed in a majority of human and mouse tissues. In human, VEGF-B is most prominently expressed in heart, skeletal muscle, pancreas, brain and prostate. In mouse, VEGF-B is mostly expressed heart, skeletal muscle, brain and kidney. Liver does not appear to express a significant level of VEGF-B in either humans or mice. VEGF-B and VEGF are coexpressed in many human tissues, such as heart, skeletal muscle, pancreas and prostate. In general, VEGF-B is more abundantly expressed than VEGF. VEGF-B can act as an endothelial cell growth factor (Olofsson, B., et al., Proc Natl Acad Sci USA 93:2576–81, 1996).

VEGF-C has an approximately 2.4 kb transcript that is expressed in multiple human tissues, most prominently in heart, skeletal muscle, placenta, ovary, small intestine, pancreas and prostate. Several tissues, including brain and liver, do not appear to express detectable levels of VEGF-C (Joukov, V., et al., EMBO J 15:290–298, 1996).

VEGF-D has an approximately 2.3 kb transcript that is expressed in multiple human tissues, most prominently in heart, skeletal muscle, lung, colon and small intestine. Several tissues, including brain, liver, placenta, do not appear to express detectable levels of VEGF-D (Achen, M. G., et al., 1998 Proc Natl Acad Sci USA 95:548–53, 1998).

VEGFR-1 appears to be endothelial cell specific (Peters, K. G., et al., Proc Natl Acad Sci 90:8915–19, 1993). VEGFR-1 cDNA is approximately 7.7 kb and encodes a protein of 1338 aa. It was expressed in a variety of normal tissues of adult rat (Shibuya, M., et al., Oncogene 5:519–24, 1990). In a glioma model of tumor angiogenesis, both VEGFR-1 and VEGFR-2 are specifically expressed in EC's that have penetrated into the tumor, but are absent from ECs in the normal brain tissues. VEGF expression was detectable in glioma cells along necrotic edge (Plate, K. H., et al., Cancer Research 53:5822–27, 1993).

VEGFR-2 is expressed as an approximately 7 kb transcript (Terman, B. I., et al., Oncogene September 6 (9): 1677–83, 1991) that appears to be endothelial cell specific. VEGFR-2 is expressed ubiquitously in many tissues, including heart, placenta, lung and kidney. The expression levels of VEGFR-2 are relatively low in these tissues compared with neuropillin expression. Brain does not appear to express detectable levels of VEGFR-2 (Soker, S., et al., Cell 92:735–745, 1998). In situ hybridization analysis revealed a specific association of VEGFR-2 with endothelial cells at all stages of mouse development. It is abundant in proliferating endothelial cells of vascular sprouts and branching vessels of embryonic and early postnatal brain, but were drastically reduced in adult brain, where proliferation has ceased (Millauer, B., Cell 72:835–46, 1993).

VEGFR-3 is expressed as approximately 5.8 kb and 4.5 kb mRNAs. Most fetal tissues expressed VEGFR-3, with spleen, brain intermediate zone, and lung showing the highest levels. It does not appear to be expressed in the endothelial cells of blood vessels (Pajusola, K., et al., Cancer Res 32:5738–43, 1992). During embryonic development, VEGFR-3 is expressed in blood vessels but become largely restricted to the lymphatic endothelium postnatally (Kaipainen, A., et al., Proc Natl Acad Sci USA 92: 3566–3570, 1995).

Neuropillin-1 is expressed in both endothelial cells and many types of tumor cells as an approximately 7 kb transcript. Most tissues express high level of Neuropillin-1, especially in heart and placenta. Skeletal muscle, pancreas, lung and kidney also express high level of Neuropillin-1. Brain does not appear to express detectable levels of Neuropillin-1 (Soker, S., et al., Cell 92:735–745, 1998).

Some functions of these genes have been evaluated and are as follows.

VEGF is a specific mitogen for EC in vitro and a potent angiogenic factor in vivo. In vitro, VEGF binds and induces autophosphorylation of VEGFR-2 and VEGFR-1, but the mitogenic response is mediated only through VEGFR-2 (Waltenberger, J., JBC 269:26988–95, 1994). VEGF functions as a survival factor for newly formed vessels during developmental neovascularization, possibly through mediating interaction of endothelial cells with underlying matrix, but is not required for maintenance of mature vessels (Benjamin, L. E., et al., Proc Natl Acad Sci 94:8761–66, 1997). In embryogenesis, VEGF and VEGFR-2 interaction induces the birth and proliferation of endothelial cells (Hanahan, D., Science 277:48–50, 1997). Binding of VEGF to VEGFR-1 elicits endothelial cell-cell interactions and capillary tube formation, a process that follows closely proliferation and migration of endothelial cells (Hanahan, D., Science 277:48–50, 1997). In a tumorigenesis study, it was shown that VEGF is critical for the initial growth of T-47D breast carcinoma cells transplanted into nude mice, whereas other angiogenic factors such as bFGF can compensate for the loss of VEGF after the tumors have reached a certain size (Yoshiji, H., et al., Cancer Research 57:3924–28, 1997). VEGF is a major mediator of aberrant endothelial cells (EC) proliferation and vascular permeability in a variety of human pathologic situation, such as tumor angiogenesis, diabetic retinopathy and rheumatoid arthritis (Benjamin, L. E., et al., Proc Natl Acad Sci 94:8761–66, 1997, Soker, S., et al., Cell 92:735–745, 1998). VEGF induces expression of plasminogen activator (PA), PA inhibitor 1 (PAI-1), MMP, and interstitial collagenase in ECs. These findings are consistent with the proangiogenic activities of VEGF. VEGF promotes expression of VCAM-1 and ICAM-1 in EC, thus may facilitate the adhesion of activated NK cells to EC. VEGF may promote monocyte chemotaxis (Pepper, M. S., et al., BBRC 181:902–906, 1991; Ferrara, N., et al., Endocr Rev 18:4–25, 1997). Tumors are believed to be the principal source of VEGF. A correlation has been observed between VEGF expression and vessel density in human breast tumors, renal cell carcinoma and colon cancer (Fong, T. A. T., et al., Cancer Res 59:99–106, 1999). VEGF and PGF expressions were significantly upregulated in 96% and 91% of hypervascular renal carcinoma tissues compared with adjacent normal kidney tissues (Takahashi, A., et al., Cancer Res 54:4233–7, 1994).

VEGF-B is a mitogen for EC and may be involved in angiogenesis in muscle and heart (Olofsson, B., et al., Proc Natl Acad Sci USA 93:2576–81, 1996). In vitro, binding of VEGF-B to its receptor VEGFR-1 leads to increased expression and activity of urokinase-type plasminogen activator and plasminogen activator inhibitor, suggesting a role for VEGF-B in the regulation of extracellular matrix degradation, cell adhesion, and migration (Olofsson, B., et al., Proc Natl Acad Sci USA 95:11709–14, 1998).

VEGF-C may regulate angiogenesis of lymphatic vasculature, as suggested by the pattern of VEGF-C expression in mouse embryos (Kukk, E., et al., Development 122:3829–37, 1996). Although VEGF-C is also a ligand for VEGFR-2, the functional significance of this potential interaction is unknown. Overexpression of VEGF-C in the skin of transgenic mice resulted in lymphatic, but not vascular, endothelial proliferation and vessel enlargement, suggesting the major function of VEGF-C is through VEGFR-3 rather than VEGFR-2 (Jeltsch, M., et al., Science 276:1423–5, 1997). Using the CAM assay, VEGF and VEGF-C were shown to be specific angiogenic and lymphangiogenic growth factors, respectively (Oh, S. J., et al., Del Biol 188:96–109, 1997).

VEGF-D is a mitogen for EC. VEGF-D can also activate VEGFR-3. It is possible that VEGF-D could be involved in the regulation of growth and/or differentiation of lymphatic endothelium (Achen, M. G., et al., 1998 Proc Natl Acad Sci USA 95:548–53, 1998).

PlGF can potentiate the action of low concentrations of VEGF in vitro and in vivo (Park, J. E., et al., J Biol Chem 269:25646–54, 1994).

VEGFR-1 signaling pathway may regulate normal endothelial cell-cell or cell-matrix interactions during vascular development, as suggested by a knockout study (Fong, G. H., et al., Nature 376:65–69, 1995). Although VEGFR-1 has a higher affinity to VEGF than VEGFR-2, it does not transduce the mitogenic signals of VEGF in ECs (Soker, S., et al., Cell 92:735–745, 1998).

VEGFR-2 appears to be the major transducer of VEGF signals in EC that result in chemotaxis, mitogenicity and gross morphological changes in target cells (Soker, S., et al., Cell 92:735–745, 1998).

VEGFR-3 has an essential role in the development of the embryonic cardiovascular system before the emergence of lymphatic vessels, as shown by a knockout study (Dumont, D. J., et al., Science 282:946–949, 1998).

Neuropillin-1 is a receptor for VEGF165. It can enhance the binding of VEGF165 to VEGFR-2 and VEGF165 mediated chemotaxis (Soker, S., et al., Cell 92:735–745, 1998).

Gene regulation of some of these genes has been investigated and is discussed herein below.

In situ hybridization demonstrated VEGF mRNA was present in transplanted tumor cells but not in tumor blood vessels, indicating that immunohistochemical labeling of tumor vessels with VEGF antibodies reflects uptake of VEGF, not endogenous synthesis. VEGF protein staining was evident in adjacent preexisting venules and small veins as early as 5 hours after tumor transplant and plateaued at maximally intense levels in newly induced tumor vessels by approximately 5 days. In contrast, vessels more than approximately 0.5 mm distant from tumors were not hyperpermeable and did not exhibit immunohistochemical staining for VEGF. Vessel staining disappeared within 24–48 h of tumor rejection. These studies indicate that VEGF is synthesized by tumor cells in vivo and accumulates in nearby blood vessels. Because leaky tumor vessels initiate a cascade of events, which include plasma extravasation and which lead ultimately to angiogenesis and tumor stroma formation, VEGF plays a pivotal role in promoting tumor growth (Dvorak, H. F., et al., J Exp Med 174:1275–8, 1991). In addition, it was shown that VEGF production by stromal cells could be stimulated by transplanted tumor cells (Fukumura, D., et al., Cell, 94:715–25, 1998). Fibroblasts cultured in vitro are highly activating for VEGF promoter function compared with fibroblasts in freshly isolated tumors, indicating the culture condition did not mimic the status of normal (unactivated) tissue in vivo (Fukumura, D., et al., Cell, 94:715–25, 1998). For example, C6 tumor spheroids (C6 is a cell line derived from a rat glial tumor—C6 cells aggregate and form small spheroids in culture) implanted into nude mice became neovascularized accompanied by a gradual reduction of VEGF expression (Shweiki, D., et al., Proc Natl Acad Sci 92:768–772, 1995). The VEGF promoter region bears many of the characteristics of a house-keeping gene (Tischer, E., JBC 266:11947–11954, 1991), hence it is likely that almost any cell type could serve as a source for VEGF upon hypoxic or ischemic demand (Fukumura, D., et al., Cell, 94:715–25, 1998).

VEGF expression was upregulated by hypoxia (Shweiki, D., et al., Nature 359:843–5, 1992), due to both increased transcriptional activation and stability of its mRNA (Ikeda, E., et al., JBC 270:19761–5, 1995). In a number of in vitro studies, it was shown that hypoxia upregulates VEGF expression through the activation of PI3K/Akt pathway (Mazure, N. M., et al., Blood 90:3322–31, 1997) and HIF-1 (an enhancer induced by hypoxia and bind to VEGF promoter region) (Forsythe, J. A., MCB 16:4604–13, 1996; Mazure, N. M., et al., Blood 90:3322–31, 1997). VEGF is also upregulated by overexpression of v-Src oncogene Mukhopadhyay, D., Cancer Res. 15:6161–5, 1995), c-SRC (Mukhopadhyay, D., et al., Nature 375:577–81, 1995), and mutant ras oncogene (Plate, K. H., Nature 359:845–8, 1992). The tumor suppressor p53 downregulates VEGF expression (Mukhopadhyay, D., Cancer Res. 15:6161–5, 1995). A number of cytokines and growth factors, including PGF, TPA (Grugel, S., et al., JBC 270:25915–9,1995), EGF, TGF-b, IL-1, and IL-6 induce VEGF mRNA expression in certain type of cells (Ferrara, N., et al., Endocr Rev 18:4–25, 1997). Kaposi's sarcoma-associated herpes virus (KSHV), which encodes a G-protein-coupled receptor—a homologue of IL-8 receptor, can activate JNK/SAPK and p38MAPK and increase VEGF production, thus causing cell transformation and tumorigenicity (Bais, C., Nature 391:86–9, 1998).

The growth of androgen-dependent Shionogi carcinoma in immunodeficient mice was regressed after the mice were castrated, accompanied by decrease in VEGF expression. Two weeks after castration, a second wave of angiogenesis and tumor growth begins with a concomitant increase in VEGF expression (Jain, R. K., Proc Natl Acad Sci USA 95:10820–5, 1998).

VEGF-D is induced by transcription factor c-fos in mouse (Orlandini, M. Proc Natl Acad Sci 93:11675–80, 1996).

Overexpression of some of these genes has been evaluated using different systems.

VEGF overexpression in skin of transgenic mice induces angiogenesis, vascular hyperpermeability and accelerated tumor development (Larcher, F., et al., Oncogene 17:303–11, 1998). Retina tissue-specific VEGF overexpression in transgenic mice causes intraretinal and subretinal neovascularization (Okamoto, N., et al., Am J Pathol 151:281–91, 1997). VEGF overexpression mediated by the Tet system promotes tumorigenesis of C6 glioma cells when transplanted into nude mice. The tumors become hypervascularized with abnormally large vessels, arising from excessive fusions. The tumors were less necrotic. After VEGF expression was shut off, regression of the tumors occurred due to detachment of endothelial cells from the walls of preformed vessels and their subsequent apoptosis. Vascular collapse further leads to hemorrhages and extensive tumor necrosis (Benjamin, L. E., et al., Proc Natl Acad Sci 94:8761–66, 1997). In human-VEGF-promoter-GFP transgenic mice, implantation of solid tumor induces specific GFP expression in stromal cells. Transgenic mice were mated with T-antigen mice (able to form spontaneous mammary tumors) to generate double transgenic mice, in which spontaneous mammary tumors were formed. Strong stromal, but not tumor, expression of GFP was observed (Fukumura, D., et al., Cell, 94:715–25, 1998). A CCD camera was used to monitor GFP expression. GFP half life was shown to be between about 1.2–1.5 days (Fukumura, D., et al., Cell, 94:715–25, 1998). The transgene was integrated into the IgG locus of the chromosome through DNA recombination (Fukumura, D., et al., Cell, 94:715–25, 1998). FVB derived VEGF-GFP transgenic mice were mated with wild-type C3H mice to create hybrid mice that can be served as hosts for C3H derived tumor lines (Fukumura, D., et al., Cell, 94:715–25, 1998).

VEGF-C overexpression in the skin of transgenic mice resulted in lymphatic, but not vascular, endothelial proliferation and vessel enlargement (Jeltsch, M., et al., Science 276:1423–5, 1997).

Neuropillin-1 overexpression in transgenic mice resulted in embryonic lethality. The embryos possessed excess capillaries and blood vessels. Dilated vessels and hemorrhage were also observed (Kitsukawa, T., et al., Development 121:4309–18, 1995).

The functions of some of these genes have been evaluated in knock-out mice constructs, animal studies, and in vitro studies.

A VEGF knockout was an embryonic lethal. F1 is also embryonic lethal and angiogenesis was impaired. VEGF secretion from +/− ES cells was reduced to 50% (Carmellet, P., et al., Nature 380:435–439, 1996; Ferrara, N., et al., Nature 380:439–442, 1996).

VEGFR-1 was evaluated in a lacZ knock-in wherein a fragment of the exon that contains the ATG start codon was replaced by LacZ. Knockout mice were embryonic lethal. Blood vessels were formed, but the organization of the blood vessel was perturbed (Fong, G. H., et al., Nature 376:65–69, 1995).

VEGFR-2 was an embryonic lethal caused by defective endothelial cell development (Shalaby, F., et al., Nature 376:62–65, 1995).

VEGFR-3(LacZ Knock-in) was an embryonic lethal caused by defective blood vessel development (Dumont, D. J., et al., Science 282:946–949, 1998).

Neuropilin-1 was an embryonic lethal (Dumont, D. J., et al., Science 282:946–949, 1998).

In vitro studies showed that a mutant VEGF (a heterodimer of two mutant VEGF) (Siemeister, G., et al., Proc Natl Acad Sci 95:4625–9, 1998), as well as a GST-Exon7 (VEGF) fusion protein (Soker, S., et al., JBC 272:31582–88, 1997), was able to inhibit endothelial cell proliferation by acting as an VEGF antagonist and interfering VEGF binding to VEGFR-2 and VEGFR-1 (Siemeister, G., et al., Proc Natl Acad Sci 95:4625–9, 1998). More importantly, A VEGF neutralizing chimeric protein, containing the extracellular domain of VEGF receptor (either VEGFR-1 or VEGFR-2) fused with IgG, substantially reduced the development of retinal neovascularization when injected into mice with ischemic retinal disease (Aiello, L. P., et al., Proc Natl Acad Sci 92:10457–61, 1995).

Treatment of tumors with monoclonal antibodies directed against VEGF resulted in dramatic reduction in tumor mass due to the suppression of tumor angiogenesis (Kim, K. J., et al., Nature 362:841–44, 1993). Injection of antibodies against VEGF reduced tumor vascular permeability and vessel diameter in immunodeficient mice transplanted with human glioblastoma, colon adenocarcinoma, and melanoma (Yuan, F., et al., Proc Natl Acad Sci 93:14765–70, 1996). Retrovirus-mediated overexpression of a dominant negative form of VEGFR-2 in nude mice suppresses the growth of transplanted rat C6 glioma tumor cells (Millauer, B., et al., Nature 367:576–9, 1994) mammary, ovarian tumors and lung carcinoma (Millauer, B., et al., Cancer Res 56:1615–20, 1996).

Further promoters of interest derived from angiogenesis-related genes include, but are not limited to, the following.

Ang2 is expressed only at predominant vascular remodeling sites, such as ovary, placenta, uterus (Maisonpierre, P. C., et al., 1997 Science 277: 55–60). In glioblastoma angiogenesis, Ang2 is found to be expressed in endothelial cells of small blood vessel and capillaries while Ang1 is expressed in glioblastoma tumor cells (Stratmann, A., 1998 Am J Pathol 153: 1459–66). Ang2 is up-regulated in bovine microvascular endothelial by VEGF, bFGF, cytokines, hypoxia (Mandriota, S. J., 1998 Circ Res 83: 832–9). Ang2 transgenic overexpression disrupts angiogenesis, and is embryonic lethal (Maisonpierre, P. C., et al., 1997 Science 277: 55–60). Ang1 is widely expressed, less abundant in heart and liver (Maisonpierre, P. C., et al., 1997 Science 277: 55–60). Ang1 is expressed in mesenchymal cells and may up-regulate the expression of Tie2 in the endothelial cells (Suri, C., et al., 1996 Cell 87: 1171–1180). Ang1 overexpression in the skin of transgenic mice produces larger, more numerous, and more highly branched vessels (Suri, C., et al., Science 1998 282:468–71).

Tie2 (see, e.g., Fadel et al.; Schlaeger et al. (1995), and Schlager et al. (1997), supra) is endothelial cell specific, up-regulated during wound healing, follicle maturation (Puri, M. C., et al., 1995 EMBO J 14: 5884–91) and pathologic angiogenesis (Kaipainen, A., 1994 Cancer Research 54: 6571–77), such as, glioblastoma (Stratmann, A., 1998 Am J Pathol 153: 1459–66). Tie2 is also expressed in non-proliferating adult endothelium and endothelial cell lines (Dumont, D. J., et al. (1994) *Genes & Develop.* 8:1897–1909). A Tie2 activating mutation causes vascular dysmorphogenesis (Vikkula M, et al., 1996 Cell 87: 1181–1190). Tie2 mutant overexpression in transgenic mice is embryonic lethal (Dumont, D. J., et al., supra). The cloning and sequencing of the 7.1 kb promoter region of Tie2 is described herein (see Example 3 below).

Other promoters derived from angiogenesis-related genes that are useful in the practice of the present invention include, by way of example, promoters derived from the sequences encoding the following polypeptide products: PTEN (dual specificity phosphatase); BAI (brain-specific angiogenesis inhibitor); KAI1 (KANGAI 1); catenin beta-1 (cadherin-associated protein, beta); COX2 (PTGS2 cyclooxygenase 2, a.k.a. prostaglandin-endoperoxide synthase 2); MMP2 (72 kDa Type IV-A collagenase); MMP9 (92 kDa type IV-B collagenase); TIMP2 (tissue inhibitor of metalloproteinase 2); and TIMP3 (tissue inhibitor of metalloproteinase 3).

PTEN is a tumor suppressor gene and encodes a protein of 403 amino acids. (Li et al. (1997) *Science* 275:1943–1946; DiCristofano et al. (1998) *Nature Genet.* 19:348–355). Overexpression of PTEN has been shown to inhibit cell migration and it is postulated that this protein may function as a tumor suppressor by negatively regulating cell interactions with the extracellular matrix or by negatively regulating the PI3K/PKB/Akt signaling pathway. (Tamura et al. (1998) *Science* 280:1614–1617; Stambolic et al. (1998) *Cell* 95:29–29). Mutations in PTEN have been detected in cancer cell lines and in the germline of patients having Cowden disease, Lhernitte-Duclos disease and Bannayan-Zonana syndrome (diseases and syndromes which are characterized by hyperplastic/dysplastic changes in the prostate, skin and colon and which are associated with an increased risk of certain cancers, for example, breast cancer, prostate cancer and colon cancer). (Marsh et al. (1998) *Hum Molec Genet.* 7:507–515; Marsh et al. (1998) *J Med Genet* 35:881–885; Nelen et al. (1997) *Hum Molec Genet* 6:1383–1387).

BAI1 protein is predicted to be 1,584 amino acids in length and includes an extracellular domain, an intracellular domain and a 7-span transmembrane region similar to that of the secretin receptor (Nishimori et al. (1997) *Oncogene* 15:245–2150). The extracellular region of BAI1 has a single Arg-Gly-Asp (RGD) motif recognized by integrins and also has five sequences corresponding to the thrombospondin type I (accession number 188060) repeats that can inhibit angiogenesis includes by basic fibroblast growth factor (bFGF, accession number 134920). Shiratsuchi et al. (1997) *Cytogenet. Cell Genet.* 79:103–108, cloned 2 other brain-specific angiogenesis inhibiting genes, designated BAI2 (accession number 602683) and BAI 3 (accession number 602684). Thus, it is postulated that members of this gene family may play a role in suppression of glioblastoma.

KAI1 encodes a 267 amino acid protein that is a member of the leukocyte surface glycoprotein family. The protein has 4 hydrophobic transmembrane domains and 1 large extracellular hydrophilic domain with three potential N-glycosylation sites. (Dong et al. (1995) *Science* 268:884–886). Molecular analysis of KAI1 is described, for example, in Dong et al. (1997) *Genomics* 41:25–32. KAI1 is a tumor metastasis suppressor gene that is capable of inhibiting the metastatic process in experimental animals. Expression of KAI1 is downregulated during tumor progression of prostate, breast, lung, bladder and pancreatic cancers in humans, apparently at the transcriptional or postranscriptional level. Mashimo et al. (1998) *PNAS USA* 95:11307–11311, found that the tumor suppressor gene p53 can directly inactivate the KAI1 gene by interacting with the region 5' to the coding sequence, suggesting a direct relationship between p53 and KAI1.

Catenin beta-1 is an adherens junction (AJ) protein, which are critical for establishing and maintaining epithelial cell layers, for instance during embryogenesis, wound healing and tumor cell metastasis. Molecular analysis, including description of sequence homology to plakoglobin (accession number 173325), homology to the drosophila gene "armadillo" and interactions with Lef1/Tcf DNA binding proteins, is described, for example, in Nollet et al. (1996) *Genomics* 32:413–424; McCrea et al. (1991) *Science* 254:1359–1361 and Korinek et al. (1997) *Science* 275:1784–1787. In addition, studies by Korinek et al., supra and Morin et al.(1997) *Science* 275:1787–1790, have indicated that APC (accession number 175100) negatively regulates catenin beta and that regulation of this protein is critical to the tumor suppressive effect of APC. Abnormally high levels of beta-catenin have been detected in certain human melanoma cell lines. (Rubinfeld et al. (1997) *Science* 275:1790–1792. Koch et al. (1999) *Cancer Res.* 59:269–273 report that childhood hepatoblastomas frequently carry a mutated degradation-targeting box of the beta-catenin gene. Transgenic mice that express catenin beta under the control of an epidermal promoter undergo de novo hair morphogenesis and eventually these animals develop two types of tumors—epithelioid cysts and trichofolliculomas. Gat et al. (1998) *Cell* 95:605–614.

COX2 encodes a cyclooxygenase and is a key regulator of prostaglandin synthesis. (Hla et al. (1992) *PNAS USA* 89:7384–7388; Jones et al. (1993) *J. Biol. Chem.* 268:9049–9054). In particular, COX2 is generally considered to be a mediator of inflammation and overexpression of COX2 in rat epithelial cells results in elevated levels of E-cadherin and Bcl2. (Tsujii & DuBois (1995) *Cell* 83:493–501). In co-cultures of endothelial cells and colon carcinoma cells, cells that overexpress COX2 produce prostaglandins, proangiogenic factors and stimulate both endothelial migration and tube formation. (Tsujii et al. (1998) *Cell* 93:705–716). Experiments conducted using APC knock-out mice have demonstrated that animals homozygous for a disrupted COX2 locus develop significantly more adenomatous polyps. (Oshima et al. (1996) *Cell* 87:803–809). COX-2 "knock out" mice develop severe nephropathy, are susceptible to peritonitis, exhibit reduced arachidonic acid-induced inflammation and exhibit reduced indomethacin-induced gastric ulceration. (Morham et al. (1995) *Cell* 83:473–482; Langenbach et al. (1995) *Cell* 83:483–492). Female mice that are deficient in cyclooxygenase 2 exhibit multiple reproductive failures. (Lim et al. (1997) *Cell* 91:197–208.

MMP2 is a metalloproteinase that specifically cleaves type IV collagen. A C-terminal fragment of MMP2, termed PEX, prevents normal biding to alpha-V/beta-3 and disrupts angiogenesis and tumor growth. (Brooks et al. (1998) *Cell* 92:391–400).

MMP9 is a collagenase secreted from normal skin fibroblasts. MMP9 null mice exhibit an abnormal pattern of skeletal growth plate vascularization and ossification. (Vu et al. (1998) *Cell* 93:411–422).

TIMP2 is a collagenase and appears to play a major role in modulating the activity of interstitial collagenase and a number of connective tissue metalloendoproteases. (Stetler-Stevenson et al. (1989) *J. Biol. Chem.* 264:17372–17378). Unlike TIMP1 and TIMP3, TIMP2 is not upregulated by TPA or TGF-beta. (Hammani et al. (1996) *J. Biol. Chem.* 271:25498–25505).

TIMP3 (Wilde et al. (1994) *DNA Cell Biol.* 13:711–718) is localized in the extracellular matrix in both its glycosylated and unglycosylated forms. Studies of mutant TIMP3 proteins have demonstrated that C-terminal trunctions do not bind to the extracellular matrix. (Langton et al. (1998) *J. Biol. Chem.* 273:16778–16781).

As one of skill in the art will appreciate in view of the teachings of the present specification, transcription control element sequences can be derived and isolated from, e.g., genomic sequences, using method known in the art in view of the teachings herein. For example, the transcription control element sequences of VEGF, VEGFR-2 and Tie2 were isolated and sequenced as described in Examples 1, 2 and 3 below. Another exemplary method of isolating promoter sequences employs a GenomeWalker® kit, commercially available from Clontech (Palo Alto, Calif.), and described on page 27 of the 1997–1998 Clontech catalog.

2.2.1 Mouse VEGF, VEGF-R2 and TIE2 Transcription Control Element Sequences

The subject nucleic acids of the present invention (e.g., as described in Examples 1, 2 and 3) find a wide variety of applications including use as hybridization probes, PCR primers, expression cassettes useful for compound screening, detecting the presence of VEGF, VEGFR-2 and/or Tie2 genes or varients thereof, detecting the presence of gene transcripts, detecting or amplifying nucleic acids encoding additional VEGF, VEGFR-2, and/or Tie2 promoter sequences or homologues thereof (as well as, structural analogs), and in a variety of screening assays.

The present invention provides efficient methods of identifying pharmacological agents or lead compounds for agents active at the level of VEGF, VEGFR-2, and Tie2 gene transcription. A wide variety of assays for transcriptional can be used based on the teaching of the present specification, including, but not limited to, cell-based transcription assays, screening in vivo in transgenic animals, and promoter-protein binding assays. For example, the disclosed luciferase reporter constructs are used to transfect cells for cell-based transcription assays. For example, primary endothelial cells are plated onto microtiter plates and used to screen libraries of candidate agents for compounds which modulate the transcriptional regulation of the VEGFR-2 and Tie2 gene promoters, as monitored by luciferase expression (See Example 5 and Example 6.).

As noted above, the present invention relates to a recombinant nucleic acid molecule comprising transcription control elements derived from a mouse VEGF gene locus. This invention provides an isolated polynucleotide comprising, a polynucleotide having X contiguous nucleotides, wherein (i) the X contiguous nucleotides have at least about 95% identity to Y contiguous nucleotides derived from nucleotides 1 through 3,762 of SEQ ID NO:44, (ii) X equals Y, and (iii) X is greater than or equal to 50. X is in the range of 50 to 3,762 nucleotides in length including all integer values in that range. The present invention may also include a nucleic acid sequence substantially complementary to said polynucleotide sequences, or fragments thereof, as well as, a nucleic acid sequence that specifically hybridizes to said polynucleotide sequences or fragments thereof. In one embodiment, the isolated polynucleotide consists of a polynucleotide having greater than 80% identity to the sequence presented as SEQ ID NO:44.

The present invention further relates to a recombinant nucleic acid molecule comprising transcription control elements derived from a mouse VEGFR-2 gene locus. This invention provides a polynucleotide having X contiguous nucleotides, wherein (i) the X contiguous nucleotides have at least about 95% identity to Y contiguous nucleotides derived from nucleotides 1 through 3,564 of SEQ ID NO:32, (ii) X equals Y, and (iii) X is greater than or equal to 55. X is in the range of 55 to 3,564 nucleotides in length including all integer values in that range. The present invention may also include a nucleic acid sequence substantially complementary to said polynucleotide sequences, or fragments thereof, as well as, a nucleic acid sequence that specifically hybridizes to said polynucleotide sequences or fragments thereof. In one embodiment, the isolated polynucleotide consists of a polynucleotide having greater than 80% identity to the sequence presented as SEQ ID NO:32.

Finally, the present invention relates to a recombinant nucleic acid molecule comprising transcription control elements derived from a mouse Tie2 gene locus. This invention provides a polynucleotide having X contiguous nucleotides, wherein in a first embodiment, (A), (i) the X contiguous nucleotides have at least about 95% identity to Y contiguous nucleotides derived from nucleotides 1 through 6,091 of SEQ ID NO:40, (ii) X equals Y, and (iii) X is greater than or equal to 55, and/or in a second embodiment, (B), (i) the X contiguous nucleotides have at least about 90% identity to Y contiguous nucleotides derived from nucleotides 6,091 through 6,560 of SEQ ID NO:40, (ii) X equals Y, and (iii) X is greater than or equal to 250. For polynucleotide (A), X is in the range of 55 to 6,091 nucleotides in length including all integer values in that range. For polynucleotide (B), X is in the range of 250 through 469 nucleotides in length including all integer values in that range. The present invention may also include a nucleic acid sequence substantially complementary to said polynucleotide sequences, or fragments thereof, as well as, a nucleic acid sequence that specifically hybridizes to said polynucleotide sequences or fragments thereof. In one embodiment, the isolated polynucleotide consists of a polynucleotide having greater than 80% identity to the sequence presented as SEQ ID NO:40.

The invention includes further transcription control element sequences (e.g., promoter sequences) identified based on the teachings of the present specification (including, but not limited to, sequence information and isolation methods, e.g., Examples 1, 2, and 3).

The nucleic acid molecules of this invention are useful for producing transfected cells and transgenic animals that are themselves useful in a variety of applications, and for screening for compounds that modulate tumorigenic and angiogenic processes (see Examples 5 through 14 below).

Those skilled in the art can practice the invention by following the guidance of the specification supplemented with standard procedures of molecular biology for the isolation and characterization of the VEGF, VEGFR-2 and Tie2 transcription control elements, their transfection into host cells, and vascular endothelial cell-specific expression of heterologous DNA operably linked to said VEGF, VEGFR-2 and Tie2 promoters. For example, DNA is commonly transferred or introduced into recipient mammal cells by calcium phosphate-mediated gene transfer, electroporation, lipofection, viral infection, and the like. General methods and vectors for gene transfer and expression may be found, for example, in M. Kriegler, Gene Transfer and Expression: A Laboratory Manual, Stockton Press (1990). Direct gene transfer to cells in vivo can be achieved, for example, by the use of modified viral vectors, including, but not limited to, retroviruses, adenoviruses, adeno-associated viruses and herpes viruses, liposomes, and direct injection of DNA into certain cell types. In this manner, recombinant expression vectors and recombinant cells containing the novel VEGF, VEGFR-2 and Tie2 transcription control elements of the present invention operably linked to a desired heterologous gene can be delivered to specific target cells in vivo. See, e.g., Wilson, Nature, 365: 691–692 (1993); Plautz et al, Annals NY Acad. Sci., 716: 144–153 (1994); Farhood et al, Annals NY Acad. Sci., 716: 23–34 (1994) and Hyde et al Nature, 362: 250–255 (1993). Furthermore, cells may be transformed ex vivo and introduced directly at localized sites by injection, e.g., intra-articular, intracutaneous, intramuscular and the like.

Cloning and characterization of the VEGF-, VEGFR-2- and Tie2-locus-derived transcription control elements are described in Examples 1 through 3, below.

2.3.0 Expression Cassettes and Vectors

The expression cassettes described herein may typically include the following components: (1) a polynucleotide encoding a reporter gene, such as a sequence encoding a light generating protein, (2) a transcription control element operably linked to the reporter gene sequence, wherein the control element is heterologous to the coding sequences of the light generating protein (e.g., the novel VEGF, VEGF-R2 and Tie2 promoters of the present invention). Transcription control elements derived from the sequences provided herein may be associated with, for example, a basal transcription promoter to confer regulation on such a basal transcription promoter. Exemplary expression constructs are described in Examples 1 through 4.

The present invention also includes providing such expression cassettes in vectors, comprising, for example, a suitable vector backbone and optionally a sequence encoding a selection marker e.g., a positive or negative selection marker. Suitable vector backbones generally include an F1 origin of replication; a colE1 plasmid-derived origin of replication; polyadenylation sequence(s); sequences encoding antibiotic resistance (e.g., ampicillin resistance) and other regulatory or control elements. Non-limiting examples of appropriate backbones include: pBluescriptSK (Stratagene, La Jolla, Calif.); pBluescriptKS (Stratagene, La Jolla, Calif.) and other commercially available vectors.

A variety of reporter genes may be used in the practice of the present invention. Preferred are those that produce a protein product which is easily measured in a routine assay. Suitable reporter genes include, but are not limited to chloramphenicol acetyl transferase (CAT), light generating proteins (e.g., luciferase), and beta-galactosidase. Convenient assays include, but are not limited to calorimetric, fluorimetric and enzymatic assays. In one aspect, reporter genes may be employed that are expressed within the cell and whose extracellular products are directly measured in the intracellular medium, or in an extract of the intracellular medium of a cultured cell line. This provides advantages over using a reporter gene whose product is secreted, since the rate and efficiency of the secretion introduces additional variables that may complicate interpretation of the assay. In a preferred embodiment, the reporter gene is a light generating protein. When using the light generating reporter proteins described herein, expression can be evaluated accurately and non-invasively as described above (see, for example, Contag, P. R., et al., (1998) Nature Med. 4:245–7; Contag, C. H., et al., (1997) Photochem Photobiol. 66:523–31; Contag, C. H., et al., (1995) Mol Microbiol. 18:593–603).

In one aspect of the invention, the light generating protein is luciferase. Luciferase coding sequences useful in the practice of the present invention include sequences obtained from lux genes (procaryotic genes encoding a luciferase activity) and luc genes (eucaryotic genes encoding a luciferase activity). A variety of luciferase encoding genes have been identified including, but not limited to, the following: B. A. Sherf and K. V. Wood, U.S. Pat. No. 5,670,356, issued 23 Sep. 1997; Kazami, J., et al., U.S. Pat. No. 5,604,123, issued 18 Feb. 1997; S. Zenno, et al, U.S. Pat. No. 5,618,722; K. V. Wood, U.S. Pat. No. 5,650,289, issued 22 Jul. 1997; K. V. Wood, U.S. Pat. No. 5,641,641, issued 24 Jun. 1997; N. Kajiyama and E. Nakano, U.S. Pat. No. 5,229,285, issued 20 Jul. 1993; M. J. Cormier and W. W. Lorenz, U.S. Pat. No. 5,292,658, issued 8 Mar. 1994; M. J. Cormier and W. W. Lorenz, U.S. Pat. No. 5,418,155, issued 23 May 1995; de Wet, J. R., et al, *Molec. Cell. Biol.* 7:725–737, 1987; Tatsumi, H. N., et al, *Biochim. Biophys. Acta* 1131:161–165, 1992; and Wood, K. V., et al, *Science* 244:700–702, 1989; all herein incorporated by reference. Eucaryotic luciferase catalyzes a reaction using luciferin as a luminescent substrate to produce light, whereas procaryotic luciferase catalyzes a reaction using an aldehyde as a luminescent substrate to produce light.

Wild-type firefly luciferases typically have emission maxima at about 550 nm. Numerous variants with distinct emission maxima have also been studied. For example, Kajiyama and Nakano (*Protein Eng.* 4(6):691–693, 1991; U.S. Pat. No. 5,330,906, issued 19 Jul. 1994, herein incorporated by reference) teach five variant firefly luciferases generated by single amino acid changes to the *Luciola cruciata* luciferase coding sequence. The variants have emission peaks of 558 nm, 595 nm, 607 nm, 609 nm and 612 nm. A yellow-green luciferase with an emission peak of about 540 nm is commercially available from Promega, Madison, Wis. under the name pGL3. A red luciferase with an emission peak of about 610 nm is described, for example, in Contag et al. (1998) *Nat. Med.* 4:245–247 and Kajiyama et al. (1991) *Port. Eng.* 4:691–693.

Positive selection markers include any gene which a product that can be readily assayed. Examples include, but are not limited to, an HPRT gene (Littlefield, J. W., Science 145:709–710 (1964), herein incorporated by reference), a xanthine-guanine phosphoribosyltransferase (GPT) gene, or an adenosine phosphoribosyltransferase (APRT) gene (Sambrook et al., supra), a thymidine kinase gene (i.e. "TK") and especially the TK gene of the herpes simplex virus (Giphart-Gassler, M. et al., Mutat. Res. 214:223–232 (1989) herein incorporated by reference), a nptII gene (Thomas, K. R. et al., Cell 51:503–512 (1987); Mansour, S. L. et al., Nature 336:348–352 (1988), both references herein incorporated by reference), or other genes which confer resistance to amino acid or nucleoside analogues, or antibiotics, etc., for example, gene sequences which encode enzymes such as dihydrofolate reductase (DHFR) enzyme, adenosine deaminase (ADA), asparagine synthetase (AS), hygromycin B phosphotransferase, or a CAD enzyme (carbamyl phosphate synthetase, aspartate transcarbamylase, and dihydroorotase). Addition of the appropriate substrate of the positive selection marker can be used to determine if the product of the positive selection marker is expressed, for example cells which do not express the positive selection marker nptII, are killed when exposed to the substrate G418 (Gibco BRL Life Technology, Gaithersburg, Md.).

The vector typically contains insertion sites for inserting polynucleotide sequences of interest, e.g., the novel VEGF, VEGFR-2 and Tie2 promoters of the present invention. These insertion sites are preferably included such that there are two sites, one site on either side of the sequences encoding the positive selection marker, luciferase and the promoter. Insertion sites are, for example, restriction endonuclease recognition sites, and can, for example, represent unique restriction sites. In this way, the vector can be digested with the appropriate enzymes and the sequences of interest ligated into the vector.

Optionally, the vector construct can contain a polynucleotide encoding a negative selection marker. Suitable negative selection markers include, but are not limited to, HSV-tk (see, e.g., Majzoub et al. (1996) *New Engl. J. Med.* 334: 904–907 and U.S. Pat. No. 5,464,764), as well as genes encoding various toxins including the diphtheria toxin, the tetanus toxin, the cholera toxin and the pertussis toxin. A further negative selection marker gene is the hypoxanthine-guanine phosphoribosyl transferase (HPRT) gene for negative selection in 6-thioguanine.

Exemplary promoters for use in the practice of the present invention are described above.

Vector Construction: The vectors described herein can be constructed utilizing methodologies known in the art of molecular biology (see, for example, Ausubel or Maniatis) in view of the teachings of the specification. As described above, the vector constructs containing the expression cassettes are assembled by inserting, into a suitable vector backbone, (1) polynucleotides encoding a reporter protein, such as a light-generating protein, e.g., a luciferase gene, operably linked to a transcription control element(s) of interest; (2) a sequence encoding a positive selection marker; and, optionally (3) a sequence encoding a negative selection marker. In addition, the vector construct contains insertion sites such that additional sequences of interest can be readily inserted to flank the sequence encoding positive selection marker and luciferase-encoding sequence.

A preferred method of obtaining polynucleotides, suitable regulatory sequences (e.g., promoters) is PCR. General procedures for PCR as taught in MacPherson et al., PCR: A PRACTICAL APPROACH, (IRL Press at Oxford University Press, (1991)). PCR conditions for each application reaction may be empirically determined. A number of parameters influence the success of a reaction. Among these parameters are annealing temperature and time, extension time, Mg2+ and ATP concentration, pH, and the relative concentration of primers, templates and deoxyribonucleotides. Exemplary primers are described below in the Examples. After amplification, the resulting fragments can be detected by agarose gel electrophoresis followed by visualization with ethidium bromide staining and ultraviolet illumination.

In one embodiment, PCR can be used to amplify fragments from genomic libraries. Many genomic libraries are commercially available. Alternatively, libraries can be produced by any method known in the art. Preferably, the organism(s) from which the DNA is has no discernible disease or phenotypic effects. This isolated DNA may be obtained from any cell source or body fluid (e.g., ES cells, liver, kidney, blood cells, buccal cells, cerviovaginal cells, epithelial cells from urine, fetal cells, or any cells present in tissue obtained by biopsy, urine, blood, cerebrospinal fluid (CSF), and tissue exudates at the site of infection or inflammation). DNA is extracted from the cells or body fluid using known methods of cell lysis and DNA purification. The purified DNA is then introduced into a suitable expression system, for example a lambda phage.

Another method for obtaining polynucleotides, for example, short, random nucleotide sequences, is by enzymatic digestion. As described below in the Examples, short DNA sequences generated by digestion of DNA from vectors carrying genes encoding luciferase (yellow green or red).

Polynucleotides are inserted into vector backbones using methods known in the art. For example, insert and vector DNA can be contacted, under suitable conditions, with a restriction enzyme to create complementary or blunt ends on each molecule that can pair with each other and be joined with a ligase. Alternatively, synthetic nucleic acid linkers can be ligated to the termini of a polynucleotide. These synthetic linkers can contain nucleic acid sequences that correspond to a particular restriction site in the vector DNA. Other means are known and, in view of the teachings herein, can be used.

The vector backbone may comprise components functional in more than one selected organism in order to provide a shuttle vector, for example, a bacterial origin of replication and a eucaryotic promoter.

The final constructs can be used immediately (e.g., for introduction into ES cells), or stored frozen (e.g., at −20° C.) until use. Preferably, the constructs are linearized prior to use, for example by digestion with suitable restriction endonucleases.

2.4.0 Transgenic Animals

The expression cassettes of the present invention may be introduced into the genome of an animal in order to produce transgenic animals for purposes of practicing the methods of the present invention. In a preferred embodiment of the present invention, the transgenic animal is a transgenic rodent, for example, a mouse, rat, or guinea pig. A variety of transformation techniques are well known in the art. Those methods include the following.

(i) Direct microinjection into nuclei: Expression cassettes can be microinjected directly into animal cell nuclei using micropipettes to mechanically transfer the recombinant DNA. This method has the advantage of not exposing the DNA to cellular compartments other than the nucleus and of yielding stable recombinants at high frequency. See, Capecchi, M., Cell 22:479–488 (1980).

For example, the expression cassettes of the present invention may be microinjected into the early male pronucleus of a zygote as early as possible after the formation of the male pronucleus membrane, and prior to its being processed by the zygote female pronucleus. Thus, microinjection according to this method should be undertaken when the male and female pronuclei are well separated and both are located close to the cell membrane. See U.S. Pat. No. 4,873,191 to Wagner, et al. (issued Oct. 10, 1989).

(ii) Electroporation: The DNA containing the expression cassettes of the present invention can also be introduced into the animal cells by electroporation. In this technique, animal cells are electroporated in the presence of DNA containing the expression cassette. Electrical impulses of high field strength reversibly permeabilize biomembranes allowing the introduction of the DNA. The pores created during electroporation permit the uptake of macromolecules such as DNA. Procedures are described in, e.g., Potter, H., et al., Proc. Nat'l. Acad. Sci. U.S.A. 81:7161–7165 (1984); and Sambrook, ch. 16.

(iii) Calcium phosphate precipitation: The expression cassettes may also be transferred into cells by other methods of direct uptake, for example, using calcium phosphate. See, e.g., Graham, F., and A. Van der Eb, Virology 52:456–467 (1973); and Sambrook, ch.16.

(iv) Liposomes: Encapsulation of DNA within artificial membrane vesicles (liposomes) followed by fusion of the liposomes with the target cell membrane can also be used to introduce DNA into animal cells. See Mannino, R. and S. Gould-Fogerite, BioTechniques, 6:682 (1988).

(v) Viral capsids: Viruses and empty viral capsids can also be used to incorporate DNA and transfer the DNA to animal cells. For example, DNA can be incorporated into empty polyoma viral capsids and then delivered to polyoma-susceptible cells. See, e.g., Slilaty, S. and H. Aposhian, Science 220:725 (1983).

(vi) Transfection using polybrene or DEAE-dextran: These techniques are described in Sambrook, ch.16.

(vii) Protoplast fusion: Protoplast fusion typically involves the fusion of bacterial protoplasts carrying high numbers of a plasmid of interest with cultured animal cells, usually mediated by treatment with polyethylene glycol. Rassoulzadegan, M., et al., Nature, 295:257 (1982).

(viii) Ballistic penetration: Another method of introduction of nucleic acid segments is high velocity ballistic penetration by small particles with the nucleic acid either within the matrix of small beads or particles, or on the surface, Klein, et al., Nature, 327, 70–73, 1987.

Any technique that can be used to introduce DNA into the animal cells of choice can be employed. Electroporation has the advantage of ease and has been found to be broadly applicable, but a substantial fraction of the targeted cells may be killed during electroporation. Therefore, for sensitive cells or cells which are only obtainable in small numbers, microinjection directly into nuclei may be preferable. Also, where a high efficiency of DNA incorporation is especially important, such as transformation without the use of a selectable marker (as discussed above), direct microinjection into nuclei is an advantageous method because typically 5–25% of targeted cells will have stably incorporated the microinjected DNA. Retroviral vectors are also highly efficient but in some cases they are subject to other shortcomings, as described by Ellis, J., and A. Bernstein, Molec. Cell. Biol. 9:1621–1627 (1989). Where lower efficiency techniques are used, such as electroporation, calcium phosphate precipitation or liposome fusion, it is preferable to have a selectable marker in the expression cassette so that stable transformants can be readily selected, as discussed above.

In some situations, introduction of the heterologous DNA will itself result in a selectable phenotype, in which case the targeted cells can be screened directly for homologous recombination. For example, disrupting the gene hart results in resistance to 6-thioguanine. In many cases, however, the transformation will not result in such an easily selectable phenotype and, if a low efficiency transformation technique such as calcium phosphate precipitation is being used, it is preferable to include in the expression cassette a selectable marker such that the stable integration of the expression cassette in the genome will lead to a selectable phenotype. For example, if the introduced DNA contains a neo gene, then selection for integrants can be achieved by selecting cells able to grow on G418.

Transgenic animals prepared as above are useful for practicing the methods of the present invention. Operably linking a promoter of interest to a reporter sequence enables persons of skill in the art to monitor a wide variety of biological processes involving expression of the gene from which the promoter is derived. The transgenic animals of the present invention that comprise the expression cassettes of the present invention provide a means for skilled artisans to observe those processes as they occur in vivo, as well as to elucidate the mechanisms underlying those processes.

With respect to transgenic animals carrying expression cassettes that employ a light-generating protein as a reporter sequence, the monitoring of expression of luciferase reporter expression cassettes using non-invasive whole animal imaging has been described (Contag, C. et al, U.S. Pat. No. 5,650,135, Jul. 22, 1997, herein incorporated by reference; Contag, P., et al, *Nature Medicine* 4(2):245–247, 1998; Contag, C., et al, *OSA TOPS on Biomedical Optical Spectroscopy and Diagnostics* 3:220–224, 1996; Contag, C. H., et al, *Photochemistry and Photobiology* 66(4):523–531, 1997; Contag, C. H., et al, *Molecular Microbiology* 18(4): 593–603, 1995). Such imaging typically uses at least one photo detector device element, for example, a charge-coupled device (CCD) camera.

Thus, in one exemplary embodiment, female transgenic mice carrying expression cassettes comprising the VEGFR2 promoter operably linked to a luciferase-encoding reporter sequence may be used to monitor VEGFR2-mediated angiogenesis in the female reproductive organs over the course of estrus. See Example 7 below. In a further exemplary embodiment, neonatal VEGFR-2 transgenic mice may be used to monitor angiogenesis over the course of the first eight weeks of development. See Example 8 below. The transgenic animals of the present invention that comprise the expression cassettes of the present invention also provide a means for screening analytes that may be capable of modulating such processes and thereby identifying compounds with potential pharmaceutical applications.

Methods of administration of the analyte include, but are not limited to, injection (subcutaneously, epidermally, intradermally), intramucosal (such as nasal, rectal and vaginal), intraperitoneal, intravenous, oral or intramuscular. Other modes of administration include oral and pulmonary administration, suppositories, and transdermal applications. Dosage treatment may be a single dose schedule or a multiple dose schedule. For example, the analyte of interest can be administered over a range of concentration to determine a dose/response curve. The analyte may be administered to a series of test animals or to a single test animal (given that response to the analyte can be cleared from the transgenic animal).

Thus, in one exemplary embodiment, female transgenic mice carrying expression cassettes comprising the VEGFR-2 promoter operably linked to a luciferase-encoding reporter sequence may be used to monitor the effects of known endocrine disrupter compounds on VEGFR-2 angiogenesis in the female reproductive organs over the course of estrus. See Example 9 below. In another exemplary embodiment, the effects of growth factors on VEGFR-2 promoter-mediated angiogenesis may be observed using transgenic mice carrying expression cassettes comprising the VEGFR-2 promoter operably linked to a luciferase-encoding reporter gene. See Example 10 below.

In another exemplary embodiment, transgenic mice of the present invention are implanted with tumor cells, treated with compounds known to affect angiogenesis, and monitored to determine the effects of those compounds on tumor-induced angiogenesis and thereby screen for compounds which may possess angiogenesis-modulating activity. For example, VEGF and VEGFR-2 transgenic mice were first implanted with cells from several compatible tumor cell lines, then treated with a variety of putative antitumorigenic anti-angiogenic agent, and finally subjected to in vivo bioluminescent imaging to monitor the effects of those compounds on tumor growth. The results obtained were then compared with those obtained from untreated control animals. See Example 13 and Example 14 below. The results of those experiments demonstrate that the transgenic mice of the present invention may be used to screen compounds which may be effective pharmaceutical agents.

2.5.0 Monitoring Promoter Activity

Activity of the transcription control element sequences comprising the expression cassettes and vectors of the present invention may be monitored by detecting and/or quantifying the protein products encoded by the reporter sequences operably linked to those promoters. The particular method used to monitor promoter activity depends on the reporter sequence employed, and may include, for example, enzymatic assay methods, as well as, in the case of reporter sequences which encode light-generating proteins, in vitro or in vivo bioluminescent imaging.

For example, promoter activity in transgenic animals carrying the expression cassettes of the present invention may be monitored using in vivo bioluminescence imaging (see Contag et al., (see, for example, Contag, P. R., et al., (1998) Nature Med. 4:245–7; Contag, C. H., et al., (1997) Photochem Photobiol. 66:523–31; Contag, C. H., et al., (1995) Mol Microbiol. 18:593–603).

Monitoring promoter activity in turn enables one to monitor the biological processes with which that promoter is associated. It may further be employed in methods of screening analytes which modulate those processes at the promoter level (see discussion in the following section).

Thus, in one aspect of the invention, the transgenic animals carrying expression cassettes comprising promoter sequences derived from angiogenesis-related gene locii such as those described above may be used to monitor angiogenesis as it occurs during a variety of biological processes.

In one embodiment, pregnant female mice carrying VEGF, VEGFR-2 or Tie2 transgenic embryos were monitored via the in vivo bioluminescence imaging method cited above in order to model VEGF, VEGFR-2 and/or Tie2 expression in those embryos during the course of prenatal development. The pups are then monitored for 1 to 8 weeks after birth in order to study VEGF, VEGFR-2 and/or Tie2 expression during post-natal development. See Example 7 below. The results of this experiment demonstrate that the expression cassettes and transgenic animals of the present invention may be used to monitor VEGFR-2 promoter-mediated expression of bioluminescence in vivo over the course of development.

In another embodiment, VEGF, VEGFR-2 and/or Tie2 expression during the reproductive cycles of female transgenic mice is monitored via in vivo bioluminescent imaging. See, e.g., Example 8, below. The results of this experiment demonstrate that it is possible to monitor changes in VEGFR-2 promoter-mediated bioluminescence expression that occur during estrus in female mice carrying the VEGFR-2 promoter-Luc transgene cassette.

In yet another embodiment of this aspect of the invention, the effect of estrogen antagonist ICI 182 780 on estrus cycling was studied by in vivo imaging of a VEGFR2 promoter transgenic mouse that was dosed with this compound daily for 16 days. See, e.g. Example 9 below. The results of this experiment demonstrate that transgenic animals carrying the expression cassettes of the present invention may be used to investigate the effects of endocrine disrupting compounds, including but not limited the effects of estrogen antagonists such as ICI 182 789, on VEGFR-2 promoter-mediated gene expression during the estrus cycle.

The effect of growth factors on VEGFR2 expression was studied in still another embodiment of this aspect of the invention by in vivo imaging of a VEGFR2 promoter transgenic mouse that was implanted with a growth factor-containing matrigel. See, e.g. Example 10 below. The results of this experiment demonstrate that transgenic animals carrying the expression constructs of the present invention may be used to investigate the effects of growth factors on VEGFR-2 promoter-mediated gene expression during the process of angiogenesis.

In a further embodiment, VEGF expression in tumor cells was monitored by in vivo imaging of C57BL/6J-Tyr$^{c-2J/+}$ mice that were implanted with LL/2, B16F1 and T241 tumor cells stably transfected with VEGF-Luc (pTKLG-Vn-VP). See, e.g. Example 11, below. The results of this experiment demonstrate that stable tumor cells generated with an expression vector comprising the VEGF promoter operably linked to a luciferase-encoding reporter sequence may be used to investigate VEGF gene expression during tumor development.

2.6.0 Screening Analytes

The methods of monitoring promoter activity discussed above may be employed for the purpose of screening analytes which modulate a variety of biological processes, the effects of which are mediated at the promoter level. Screening may be accomplished by means of in vitro assays employing transiently or stably transfected cells, and may also be conducted using the transgenic animals of the present invention discussed above, either by themselves or in conjunction with other wild-type or transformed cells or tissues that have been introduced into those animals. The particular assay method used to measure the effects of various candidate compounds on promoter activity will be determined by the particular reporter sequence present in the expression cassette carried by the cells or animals employed. As discussed above, promoter activity in transgenic animals carrying constructs employing reporter sequences encoding light-generating proteins may be measured by means of ex vivo assay methods or by means of the in vivo bioluminescent imaging technique reference previously.

Thus, one aspect of this invention is the use of the expression cassettes and vectors for use in screening for pharmacologically active agents (or compounds) that modulate VEGF, VEGFR-2 and/or Tie2 promoter activity, either by affecting signal transduction pathways that necessarily precede transcription or by directly affecting transcription of the VEGF, VEGFR-2 and/or Tie2.

For screening purposes, appropriate host cells, preferably tumor cells for monitoring VEGF promoter-mediated expression and vascular endothelial cells for monitoring VEGFR2 promoter-mediated and Tie2 promoter-mediated expression, are transformed with an expression vectors comprising a reporter gene (e.g., luciferase) operably linked to either the VEGF, VEGFR-2 or Tie2 gene promoters of this invention. The transformed cells are next exposed to various test substances and then analyzed for expression of the reporter gene. The expression exhibited by these cells can be compared to expression from cells that were not exposed to the test substance. A compound that modulates the promoter activity of the VEGF, VEGFR-2 and/or Tie2 promoter will result in modulated reporter gene expression relative to the control. See, e.g. Example 12, below.

Thus, one aspect of the invention is to screen for test compounds that regulate (i.e., stimulate or inhibit) gene expression levels mediated by the VEGF-, VEGFR-2- and/or Tie2-locus derived transcription control elements (e.g., promoters). Screening may be accomplished by, for example, (i) contacting host cells in which the VEGF, VEGFR-2 or Tie2 promoter disclosed herein is operably linked to a reporter gene with a test medium containing the test compound under conditions which allow for expression of the reporter gene; (ii) measuring the expression of the reporter gene in the presence of the test medium; (iii) contacting the host cells with a control medium which does not contain the test compound but is otherwise essentially identical to the test medium in (i), under conditions essentially identical to those used in (i); (iv) measuring the expression of reporter gene in the presence of the control medium; and (v) relating the difference in expression between (ii) and (iv) to the ability of the test compound to affect the activity of the promoter.

Alternatively, the transformed cells may be induced with a transcriptional inducer, such as IL-1 or TNF-alpha, forskolin, dibutyryl-cAMP, or a phorbol-type tumor promoter, e.g., PMA. Transcriptional activity is measured in the presence or absence of a pharmacologic agent of known activity (e.g., a standard compound) or putative activity (e.g., a test compound). A change in the level of expression of the reporter gene in the presence of the test compound is compared to that effected by the standard compound. In this way, the ability of a test compound to affect VEGF, VEGFR-2 and/or Tie2 transcription and the relative potencies of the test and standard compounds can be determined.

Thus in a further aspect, the present invention provides methods of measuring the ability of a test compound to modulate VEGF, VEGFR-2 and/or Tie2 transcription by: (i) contacting a host cell in which the VEGF, VEGFR-2 or the Tie2 promoter, disclosed herein, is operably linked to a reporter gene with an inducer of the VEGF, VEGFR-2 or the Tie2 promoter activity under conditions which allow for expression of the reporter gene; (ii) measuring the expression of the reporter gene in the absence of the test compound; (iii) exposing the host cells to the test compound either prior to, simultaneously with, or after contacting, the host cells with the inducer; (iv) measuring the expression of the reporter gene in the presence of the test compound; and (iv) relating the difference in expression between (ii) and (iv) to the ability of the test compound to modulate VEGF, VEGFR-2 or Tie2-mediated transcription.

Because different inducers are known to affect different modes of signal transduction, it is possible to identify, with greater specificity, compounds that affect a particular signal transduction pathway. Further, VEGF and VEGFR2 have been shown to be upregulated in tumor cells and proliferating endothelial cells, respectively; this upregulation appears to be necessary for tumor angiogenesis. Therefore, such assays provide a means of identifying compounds that will inhibit and/or reverse tumor growth by downregulating VEGF and VEGFR2 expression and thus preventing or reducing tumor angiogenesis.

Compounds that are especially promising as anti-tumorigenic agents are angiogenesis inhibitors. About 20 of this class of compounds are currently being tested in human trials. Most are in the early phase I or II clinical (human) studies, three are in phase II testing, and one has already yielded results as of the end of 1999. See Table 1 below.

Without being bound by any particular mechanistic explanation, the following alternatives for possible mechanisms of action of anti-angiogenic drugs are provided herein. Four general strategies are employed to investigate the action of anti-angiogenesis drugs: 1) blocking the factors that stimulate blood vessel formation; 2) making use of natural inhibitors of angiogenesis, i.e. angiostatin and endostatin; 3) blocking the action of molecules that allow newly forming blood vessels to invade surrounding tissue; and 4) incapacitating newly dividing endothelial cells.

Several distinct advantages conferred by anti-angiogenic drug therapies as compared to traditional chemotherapy approaches include the following: (1) anti-angiogenic drugs are not likely to cause bone marrow suppression, gastrointestinal symptoms, or hair loss; and (2) drug resistance may not develop as frequently happens for chemotherapeutic agents, owing to the fact that normal endothelial cells are not genetically unstable, as are most cancer cells.

Anti-angiogenic therapy may also prove useful when administered in combination with therapies directly aimed at tumor cells.

A list of anti-angiogenic agents currently in clinical trials as anti-tumorigenic agents appears below.

TABLE 1

Angiogenesis Inhibitors in Clinical Trials

| Drug | Sponsor | Trial | Mechanism |
|---|---|---|---|
| Drugs that modulate matrix interaction or degradation | | | |
| Marimastat | British Biotech; Annapolis, MD | Phase III against pancreas, non-small cell lung cancers, breast cancers | Synthetic MMP inhibitor |
| Bay 12-9566 | Bayer; West Haven, CT | Phase III against lung and pancreatic cancers | Synthetic inhibitor of tumor growth |
| AG3340 | Agouron; LaJolla, CA | 2 trials: Phase III against non small cell lung and against prostate cancers | Synthetic MMP inhibitor |
| CGS 27023A | Novartis; East Hanover, NJ | Phase I/II | Synthetic MMP inhibitor |
| COL-3 | Collagenex; Newtown, PA/NCI | Phase I | Synthetic MMP inhibitor. Tetracycline derivative |
| Neovastat | Aeterna; Sainte-Foy, Québec | Phase III against non-small cell lung cancer (will open later in 1999) | Naturally-occurring MMP inhibitor |
| Direct inhibition of endothelial cell function or response | | | |
| TNP-470 | TAP Pharmaceuticals, Deerfield, IL | Phase II against advanced cance Adults with solid tumors; Phase I against pediatric solid tumors, tumors, lymphomas, and acute leukemias | Synthetic analogue of fungallin protein; inhibits endothelial cell growth |
| Thalidomide | Celgene; Warren, NJ | Phase II against Kaposi's sarcoma, Glioblastoma, prostate, lung, and breast cancers | |
| Squalamine | Magainin Pharmaceuticals, Inc.; Plymouth Meeting, PA | Phase I | Extract from dogfish Shark liver; inhibits sodium-hydrogen exchanger, NHE3 |
| Combretastatin | Oxigene; Boston, MA | Phase I; Phase II to begin late 1999 | Induction of apoptosis in Proliferating endothelial cells |
| Inhibition of angiogenic factor activity | | | |
| Anti-VEGF Antibody | Genentech; S. San Francisco, CA | Phase II/III against lung, breast, Prostate, colorectal, and renal cancers | Monoclonal antibody to vascular endothelial growth factor (VEGF) |
| SU5416 | Sugen, Inc.; Redwood City, CA | Phase I and Phase I/II against Kaposi's sarcoma and solid tumors | Blocks VEGF receptor signaling |
| SU6668 | Sugen, Inc: Redwood City, CA | Phase I study will open in early 1999 (London) | Blocks VEGF, FGF, and EGF receptor signaling |
| PTK787/ZK | Novartis; East Hanover, NJ | Phase I against advanced cancer (Germany and UK); Phase I against glioblastoma And Kaposi's sarcoma; and Phase I/II against Von Hippel Lindau disease (US) | Blocks VEGF receptor signaling |
| Interferon-alfa | (commercially available) | Phase II/III | Inhibition of bFGF and VEGF production |
| Inhibition of endothelial-specific integrin survival signaling | | | |
| Vitaxin | Ixsys, Inc.; La Jolla, CA | Phase II enrollment will begin in early 1999 | Antibody to integrin present on endothelial cell surface |
| EMD121974 | Merck KCgaA; Darmstadt, Germany | Phase II/III against Kaposi's sarcoma, and brain tumors (to open later in 1999) | Small molecule blocker of Integrin present on endothelial cell surface |

TABLE 1-continued

Angiogenesis Inhibitors in Clinical Trials

| Drug | Sponsor | Trial | Mechanism |
|---|---|---|---|
| Non-specific mechanism of action | | | |
| CAI | NCI; Bethesda, MD | Phase II/III against ovarian non-small cell lung, and renal cell cancers | Inhibitor of calcium influx |
| Interleukin-12 | Genetics Institute; Cambridge, MA | Phase I/II against Kaposi's sarcoma and solid tumors | Upregulation of Interferon gamma and IP-10 |
| IM862 | Cytran; Kirkland, WA | Phase III against AIDS-related Kaposi's sarcoma | Unknown mechanism |

In another aspect of this invention, transgenic animals expressing a heterologous gene encoding a detectable product placed under the regulatory control of the VEGF-, VEGFR-2- or the Tie2-locus derived transcription control elements, as disclosed herein, may be used to determine the effect of a test compound. In particular, those animals may be used to determine the effects of a test compound on levels of gene expression mediated by a VEGF, VEGFR-2 or the Tie2 promoter in vivo. The test compound is, for example, administered to the animal and the degree of expression of the heterologous gene observed is compared to the degree of expression in the absence of administration of the test compound using, for example, whole animal luciferase-based assays as disclosed herein. Methods of generating transgenic animals are described above.

Thus, in one aspect of the invention, putative anti-tumorigenic anti-angiogenesis compounds are administered to VEGF and VEGFR-2 transgenic mice in which either growth factor-containing matrigel or tumor cells (including but not limited to B16F1 melanoma cells, LL/2 Lewis Lung carcinoma cells and T241 fibrosarcoma cells) have been introduced. Test compounds are then administered, and the expression of VEGF and VEGFR-2, as determined by in vivo bioluminescence imaging, is determined and compared with that observed for untreated controls. See Examples 13 and 14 below. Such an approach allows the visualization, via bioluminescence monitoring, of angiogenesis process which occurs in response to either growth factors or to the tumor growth; it further allows the effect of putative anti-tumorigenic anti-angiogenesis compounds on VEGF and VEGFR-2 expression during these processes to be studied.

This invention also provides transgenic animals useful as models for studying other physiological and pathological processes that involve VEGF, VEGFR-2 and/or Tie2 gene expression.

Various forms of the different embodiments of the invention, described herein, may be combined.

The following examples are put forth so as to provide those of ordinary skill in the art with a complete disclosure and description of how to make and use the devices, methods, and formulae of the present invention, and are not intended to limit the scope of what the inventor regards as the invention. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXPERIMENTAL EXAMPLES

Example 1

Construction of the VEGF-Luc Expression Cassette

A. Cloning of a Novel VEGF-Locus Derived Promoter Sequence

A novel VEGF promoter sequence was isolated by PCR screening of a mouse genomic library using primers based on a known partial VEGF promoter region sequence.

First, a 2240 bp mouse VEGF genomic DNA sequence containing a partial VEGF promoter region was obtained from GenBank (Accession Number: U41383). PCR primers were designed to amplify a 0.69 kb fragment (nucleotide number 958 to 1660) (VF1-VR1A; Table 2) and a 0.98 kb fragment (nucleotide number 641 to 1624) (VF2-VR2; Table 2) using that sequence.

The ability of each primer pair to amplify the predicted product was then confirmed using mouse129SvJ genomic DNA (Genome Systems) as a template. The conditions employed for PCR amplification are shown in FIG. 1.

TABLE 2

PCR Amplification Primers for VEGF, VEGFR-2 and Tie2 Promoter and Enhancer Sequences

| NAME | SEQ ID NO: | SEQUENCE |
|---|---|---|
| VF1 | 19 | ACCTCACTCTCCTGTCTCCCCTGATTCCCAA |
| VR1A | 20 | GTCTGGCGGTCACCCCCAAAAGCA |
| VF2 | 21 | CCCTTTCCAAGACCCGTGCCATTTGAGC |
| VR2 | 22 | ACTTTGCCCCTGTCCCTCTCTCTGTTCGC |
| KF1 | 23 | GCTGCGTCCAGATTTGCTCTCAGATGCG |

TABLE 2-continued

PCR Amplification Primers for VEGF, VEGFR-2 and Tie2 Promoter and Enhancer Sequences

| NAME | SEQ ID NO: | SEQUENCE |
|---|---|---|
| KR1 | 24 | TTCTCAGGCACAGACTCCTTCTCCGTCCCT |
| KF2 | 25 | CAGATGGACGAGAAAACAGTAGAGGCGTTGGC |
| KR2 | 26 | GAGGACTCAGGGCAGAAAGAGAGCG |
| TF3 | 27 | AGCTTAGCCTGCAAGGGTGGTCCTCATCG |
| TF2 | 28 | CAAATGCACCCCAGAGAACAGCTTAGCCTGC |
| TR1 | 29 | GCTTTCAACAACTCACAACTTTGCGACTTCCCG |
| VR2F | 30 | CGCTAGTGTGTAGCCGGCGCTCTC |
| VR2R | 31 | ATAAGAATGCGGCCGCCTGCACCTCGCGCTGGGCACAG |
| VEF | 33 | ACACGCCTCGAGAAATGTGCTGTCTTTAGAAGCCACTG |
| VER | 34 | ACACGCGTCGACGATCCAATAGGAAAGCCCTTCCATAAAC |
| VR-Not | 45 | ATAAGAATGCGGCCGCGGTTTCGGAGGCCGTCCGGGG |
| T2F | 38 | TATCAACACTCGGGAGGCTGAGGGAG |
| T2R | 39 | ATAAGAATGCGGCCGCACTTCCCCAGATCTCCCCATCCAGC |

Finally, the primers designed and tested above were used to PCR screen a mouse 129/SvJ genomic DNA BAC (bacterial artificial chromosome) library (Genome Systems, Inc., St. Louis, Mo.) in order to isolate a novel VEGF promoter sequence. The library, on average, contained inserts of 120 kb with sizes ranging between 50 kb to 240 kb. A large genomic DNA fragment that contained VEGF promoter region was obtained.

Southern blot analysis was performed to map the location of the VEGF promoter region. A unique HindIII restriction site was mapped approximately 7.8 kb upstream of the ATG translational start codon of the VEGF gene. Over 6 kb of the 7.8 kb fragment containing the VEGF promoter region were sequenced. The sequence determined is presented in FIG. 2A–C (SEQ ID NO:44).

The present invention includes, but is not limited to, an isolated polynucleotide, and fragments thereof, having at least about 80–85%, preferably 85–90%, more preferably 90–95%, and most preferably 98–100% sequence identity to the sequence presented as SEQ ID NO:44. Exemplary fragments include, but are not limited to, polynucleotides having lengths of approximately 55–100, 100–250, 250–500, and 500–1,000. In particular, the present invention relates to a recombinant nucleic acid molecule comprising transcription control elements derived from a mouse VEGF gene locus. This invention provides an isolated polynucleotide comprising, a polynucleotide having X contiguous nucleotides, wherein (i) the X contiguous nucleotides have typically at least about 95% identity to Y contiguous nucleotides derived from nucleotides 1 through 3,762 of SEQ ID NO:44, (ii) X equals Y, and (iii) X is greater than or equal to 50. X is in the range of approximately 50 to approximately 3,762 nucleotides in length including all integer values in that range. Typically the polynucleotide sequence comprises one or more transcription control element(s). The present invention may also include a nucleic acid sequence substantially complementary to said polynucleotide sequences, or fragments thereof, as well as, a nucleic acid sequence that specifically hybridizes to said polynucleotide sequences or fragments thereof. In one embodiment, the isolated polynucleotide consists of a polynucleotide having greater than 80% identity to the sequence presented as SEQ ID NO:44.

B. Construction of the VEGF Expression Cassette

A 7.9 kb HindIII-SrfI VEGF promoter fragment was cloned into vector pSK (Stratagene, La Jolla, Calif.) that was linearized with HindIII and SmaI. The resulting construct was designated pSK-V32. A 0.3 kb 3' end fragment was amplified by PCR (Forward primer VF1 (SEQ ID NO:19); reverse primer VR-Not (SEQ ID NO:45)) and digested with NheI and NotI. This fragment was used to replace the 0.2 kb NheI-NotI fragment of pSK-V32 and the resulting construct was designated pSK-VP, which contains a 7.8 kb VEGF promoter sequences beginning at a HindIII site 5' to the ATG translational start codon, and ending at the ATG codon. The VEGF promoter was isolated as a HindIII-NotI fragment and cloned into the same sites of pGL3B2 (see Example 2B, below). The resulting construct was designated pGL3B2-VP.

Example 2

Construction of the VEGFR-2 Promoter-Luc YG-VEGFR-2 Enhancer Expression Cassette A. Cloning and Re-engineering of VEGFR-2-locus Derived Promoter and Enhancer Sequences 1. Cloning and Re-engineering of a Novel VEGFR-2 Promoter Sequence A novel VEGFR-2 promoter sequence was isolated by PCR screening of the same mouse genomic library employed in Example 1 (see above), using primers based on a known partial VEGFR-2 promoter region.

A mouse VEGFR-2 genomic DNA sequence of 1079 bp containing a partial VEGFR-2 promoter region (nucleotide position 3,561 TO 4,487) was published previously (Ronicke et al (1996) *Cir. Res.* 79:277–285). This sequence was used to design PCR amplification primers that were able to amplify a 0.45 kb fragment (nucleotide position 4,000 to 4,455) (KF1-KR1; Table 2) and a 0.58 kb fragment (nucleotide position 3,624 to 4,206) (KF2-KR2; Table 2).

The ability of each primer pair to amplify the predicted product was then confirmed using mouse 129SvJ genomic DNA as a template. DNA sequences for these primers are shown in Table 2 above. The PCR amplification conditions employed are shown in FIG. 1.

These primers were then used for PCR screening of a mouse 129/SvJ genomic DNA BAC library in order to isolate a novel VEGFR-2 sequence. A large genomic DNA fragment of the VEGFR-2 promoter region was obtained (the "VEGFR-2 BAC clone").

Based on the VEGFR-2 restriction map that was published (Ronicke et al, supra), a 4.6 kb HindIII-XbaI fragment that covers the VEGFR-2 promoter region was subcloned from the VEGFR-2 BAC clone into vector pSK (Stratagene, La Jolla, Calif.) linearized with HindIII and XbaI. This construct was designated pSK-K6.

The pSK-K6 construct was then re-engineered to delete a 159 bp sequence from the ATG translational start codon to a downstream XbaI site, as follows.

A 0.3 kb 3' end fragment was obtained by PCR amplification of pSK-K6 using the forward primer VR2F (SEQ ID NO:30) and the reverse primer VR2R (SEQ ID NO:31). This PCR product was digested with Bsu36I and NotI, and the resulting fragment was then used to replace the 0.45 kb Bsu36I-NotI fragment of pSK-K6. The resulting construct, designated pSK-KP, contains a novel 4.5kb VEGFR-2 promoter sequence beginning at a HindIII site 5' to the ATG translational start codon, and ending at that ATG codon.

Figure 3A:
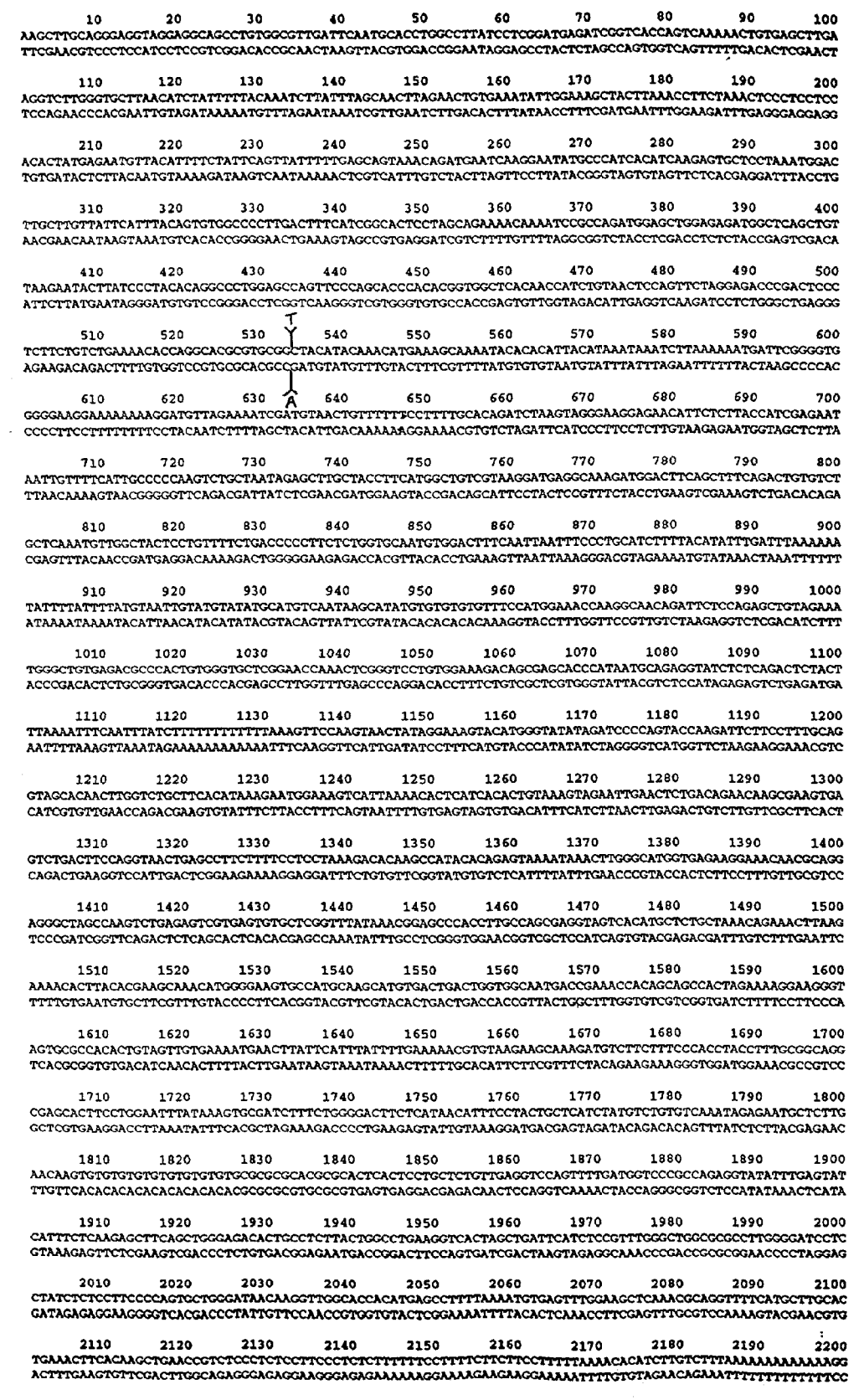

This promoter fragment was fully sequenced; and the sequence is shown in FIGS. 3A–C (SEQ ID NO:32). The present invention includes, but is not limited to, an isolated polynucleotide, and fragments thereof, having at least about 80–85%, preferably 85–90%, more preferably 90–95%, and most preferably 98–100% sequence identity to the sequence presented as SEQ ID NO:32. Exemplary fragments include, but are not limited to, polynucleotides having lengths of approximately 55–100, 100–250, 250–500, and 500–1,000. In particular, the present invention relates to a recombinant nucleic acid molecule comprising transcription control elements derived from a mouse VEGFR-2 gene locus. This invention provides a polynucleotide having X contiguous nucleotides, wherein (i) the X contiguous nucleotides have typcially at least about 95% identity to Y contiguous nucleotides derived from nucleotides 1 through 3,564 of SEQ ID NO:32, (ii) X equals Y, and (iii) X is greater than or equal to 55. X is in the range of approximately 55 to approximately 3,564 nucleotides in length including all integer values in that range. Typically the polynucleotide sequence comprises one or more transcription control element(s). The present invention may also include a nucleic acid sequence substantially complementary to said polynucleotide sequences, or fragments thereof, as well as, a nucleic acid sequence that specifically hybridizes to said polynucleotide sequences or fragments thereof. In one embodiment, the isolated polynucleotide consists of a polynucleotide having greater than 80% identity to the sequence presented as SEQ ID NO:32.

2. Cloning of a VEGFR-2 Enhancer Sequence

In a recent report, it was described that a 511 bp sequence located within the first intron of VEGFR-2 gene functions as an endothelial cell-specific expression enhancer. (Kappel et al (1999) *Blood* 12: 4284–4292). Accordingly, this VEGFR-2 enhancer sequence was amplified by PCR from the VEGFR-2 BAC clone DNA using the forward primer VEF (SEQ ID NO:33) and the reverse primer VER (SEQ ID NO:34). The 511 bp VEGFR-2 enhancer sequence is shown in FIG. 4 (SEQ ID NO:35).

The PCR product comprising the VEGFR-2 enhancer was then digested with XhoI and SalI and then cloned into the SalI site of the pSK vector. The resulting construct was designated pSK-KN.

B. Construction of the VEGFR-2 Promoter-luciferase-VEGFR-2 Enhancer Expression Cassette The following scheme for constructing the VEGFR-2 Promoter-Luc YG-VEGFR-2 Enhancer expression cassette is presented in FIG. 5.

1. Re-engineering of PGL3B

The yellow-green luciferase-containing vector pGL3B (Promega, Madison, Wis.) was re-engineered as illustrated in FIG. 5. First, pGL3B was digested with NotI and then blunt ended with T4 DNA polymerase. A PmeI linker (New England Bolas) was then ligated into the vector. The resulting vector, pGL3B-Pme, was double digested with Asp718 and HindIII and ligated with a synthetic linker that resulted from annealing two complementary oligomers, GL3B-Forward (SEQ ID NO:36) and GL3B-Reverse (SEQ ID NO:37). This construct was designated pGL3B2.

2. Insertion of the VEGFR-2 Promoter and VEGFR-2 Enhancer Sequences

After re-engineering of the pGL3B2 vector was complete, the VEGFR-2 promoter was isolated from pSK-KP (see above) as a HindIII-NotI fragment and cloned into the same sites of pGL3B2. The resulting construct was designated pGL3B2-KP. Next, the VEGFR-2 enhancer was isolated from pSK-KN as a AhoI-SalI fragment and cloned into the pGL3B2-KP vector that had been linearized with SalI. The resulting construct, containing the complete VEGFR-2 promoter-LucYG-VEGFR-2 enhancer expression cassette, was designated pGL3B2-KPN.

Example 3

Construction of the Tie-2 Promoter-Luc-Tie2 Enhancer Expression Cassette

A. Cloning and Re-engineering of Tie2-locus Derived Promoter and Enhancer Sequences 1. Cloning and Re-engineering of a Novel Tie2 Promoter Sequence A 477 bp region of the mouse Tie2 promoter has been isolated and sequenced (Fadel et al (1998) *Biochem J.* 330:335–343). Using this region, primers capable of amplifying a 0.45 kb (TF3-TR1; Table 2) and a 0.47 kb fragment (TF2-TR1; Table 2) of the Tie2 promoter were designed. The ability of each primer pair to amplify the predicted PCR product was confirmed using mouse 129SvJ genomic DNA as template. DNA sequences for these primers are shown in Table 2 above and PCR amplification conditions are shown in FIG. 1.

These primers were then used for PCR screening of the mouse 129/SvJ genomic DNA BAC library, and a large genomic DNA fragment containing a portion of the Tie2 promoter region was obtained. Based on the Tie2 genomic DNA restriction map previously published (Dumont et al (1994) *Genes and Development* 8:1897–1909), a 10.5 kb Asp718-EcoRV fragment spanning the Tie2 promoter region was subcloned from the Tie2 BAC clone which contained it into the same sites of pSK. The resulting construct was designated pSK-T67.

pSK-T67 was further engineered to delete 3.4 kb of sequence, from the ATG translational start codon to an upstream EcoRV site, as follows.

First, a 1.0 kb fragment at the 3' end of the promoter region was PCR amplified using the forward primer T2F (SEQ ID NO:38) and the reverse primer T2R (SEQ ID NO:39). The amplification product was digested with BstAPI and NotI, and the fragment used to replace the 4.0 kb BstAPI-NotI fragment of pSK-T67. The resulting construct was designated pSK-TP.

pSK-TP thus contains a 7.1 kb fragment of the Tie2 promoter sequence, from a 5' Asp718 site to the ATG translational start codon. This fragment was fully sequenced, and the sequence is shown in FIGS. 6A–D (SEQ ID NO:40).

The present invention includes, but is not limited to, an isolated polynucleotide, and fragments thereof, having at least about 80–85%, preferably 85–90%, more preferably 90–95%, and most preferably 98–100% sequence identity to the sequence presented as SEQ ID NO:40. Exemplary fragments include, but are not limited to, polynucleotides having lengths of approximately 55–100, 100–250, 250–500, and 500–1,000. In particular, the present invention relates to a recombinant nucleic acid molecule comprising transcription control elements derived from a mouse Tie-2 gene locus. This invention provides a polynucleotide having X contiguous nucleotides, wherein in a first embodiment, (A), (i) the X contiguous nucleotides have typically at least about 95% identity to Y contiguous nucleotides derived from nucleotides 1 through 6,091 of SEQ ID NO:40, (ii) X equals Y, and (iii) X is greater than or equal to 55, and/or in a second embodiment, (B), (i) the X contiguous nucleotides have at least about 90% identity to Y contiguous nucleotides derived from nucleotides 6,091 through 6,560 of SEQ ID NO:40, (ii) X equals Y, and (iii) X is greater than or equal to 250. For polynucleotide (A), X is in the range of approximately 55 to approximately 6,091 nucleotides in length including all integer values in that range. For polynucleotide (B), X is in the range of approximately 250 through approximately 469 nucleotides in length including all integer values in that range. Typically the polynucleotide sequence comprises one or more transcription control element(s). The present invention may also include a nucleic acid sequence substantially complementary to said polynucleotide sequences, or fragments thereof, as well as, a nucleic acid sequence that specifically hybridizes to said polynucleotide sequences or fragments thereof. In one embodiment, the isolated polynucleotide consists of a polynucleotide having greater than 80% identity to the sequence presented as SEQ ID NO:40.

2. Cloning of a Tie2 Enhancer Sequence

A 1.7 kb region within the first intron of the Tie2 gene was previously reported to function as an endothelial cell specific enhancer. (Schiaeger et al (1997) *PNAS USA* 94: 3058–3063). Accordingly, this 1.7 kb Tie2 enhancer region was isolated from the Tie2 Bac clone DNA by digesting with Asp718 and XhoI.

The enhancer sequence was then subcloned as a XhoI-Asp718 fragment from the Tie2 BAC clone identified above into the same sites of pSK. The Asp718 site was then converted to a SalI site using a SalI linker (New England Biolabs). The resulting construct was designated pSK-TN.

The 1.7 kb Tie2 enhancer was fully sequenced and the sequence is shown in FIG. 7 (SEQ ID NO:41).

B. Construction of the Tie2 Promoter-LucYG-Tie2 Enhancer Expression Cassette

Figure 8:
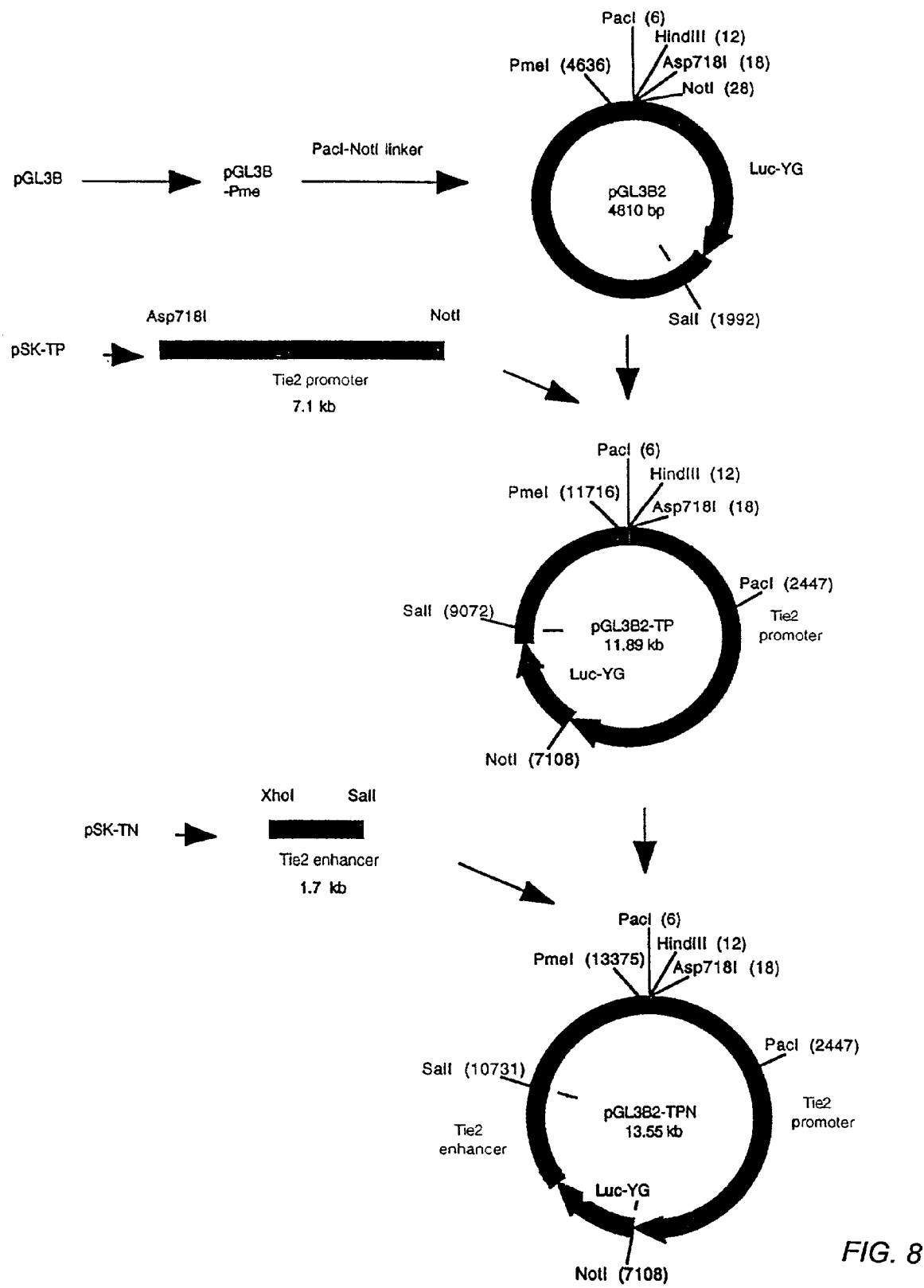
FIG. 8 is a schematic depicting construction of the pGL3B2-TPN vector construct. See Example 3B below. The Tie2 promoter is cloned into the polylinkers upstream of the Luc-YG gene.

As illustrated in FIG. 8, the Tie2 promoter was isolated from pSK-TP as a Asp718-NotI fragment and cloned into the pGL3B2 vector that was linearized with Asp718 and NotI. The resulting construct was designated pGL3B2-TP. Subsequently, the Tie2 enhancer was isolated from pSK-TN as a XhoI-SalI fragment and cloned into the pGL3B2-TP vector linearized with SalI. The resulting construct was designated pGL3B2-TPN.

Example 4

Construction of Vectors Containing the VEGF, VEGFR-2 and TIE2 Expression Cassettes Additional vector constructs containing VEGF, VEGFR-2 and TIE2 expression constructs useful in a variety of the methods of the present invention were created as described below. All have in common one of the backbone vectors pTK-LucR or pTK-LucYG.

A. Construction of the Backbone Vectors pTK-LucR and pTK-LucYG.

1. Construction of the pTK53 Starting Vector

Figure 9:
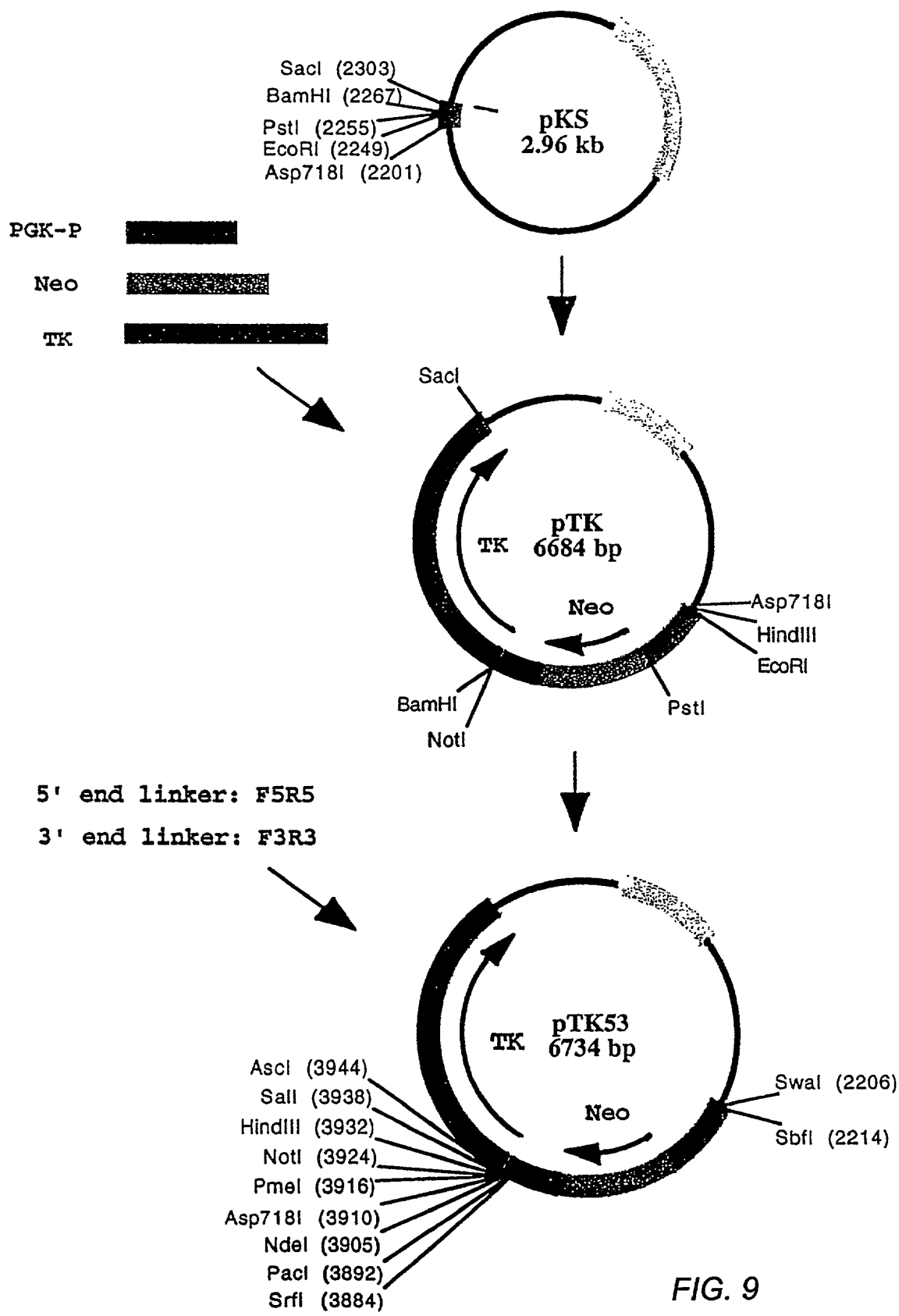
FIG. 9 is a schematic depicting construction of the pTK53 vector. Polynucleotides encoding mouse phosphoglycerate kinase 1 promoter (PGK-P), neomycin (Neo) and thymidine kinase (TK) and 5' and 3' linkers are introduced into a pKS backbone to produce the vector designated pTK53.

Initially, the vector pTK53 was constructed as illustrated in FIG. 9 by introducing sequences from the mouse phosphoglycerate kinase 1 promoter, the neomycin gene coding sequence, and the thymadine kinase gene coding sequence, as well as two synthetic polylinker sequences, into the pBluescript II KS vector (Stratagene, La Jolla, Calif.), as follows.

First, the 0.5 kb mouse phosphoglycerate kinase 1 promoter was amplified with the PGK primers PGKF (SEQ ID NO: 1) and PGK (SEQ ID NO:2) using mouse genomic DNA (Genome Systems, Inc., St. Louis, Mo.) as a template. This fragment was then double digested with EcoRI and PstI and cloned into the pBluescript II KS vector (Stratagene, La Jolla, Calif.) which was linearized with the same enzymes.

Next, the neomycin resistance gene was amplified with the PCR primers NeoF (SEQ ID NO:3) and NeoR (SEQ ID NO:4) using pNTKV1907 (Stratagene) as a template. The 1.1 kb PCR fragment obtained was double digested with PstI and BamHI and cloned into the pKS-PGK vector that was linearized with the same enzymes.

The mouse thymidine kinase gene was then cloned into the pKS-PGK-Neo vector as follows. PCR primers TKF (SEQ ID NO:5) and TKR (SEQ ID NO:6) were used to amplify the TK gene from pNTKV1907 (Stratagene). The amplified 2kb fragment obtained was next digested with BamHI and SacI and finally cloned into pKS-PGK-Neo linearized with the same enzymes. This constructed vector was designated as pTK.

Finally, synthetic linker sequences were added. A first synthetic linker, F5R5, was made by annealing two primers: a forward primer sequence F5R5F (SEQ ID NO:7) and a reverse primer sequence F5R5R (SEQ ID NO:8). This linker was inserted between the Asp718l and HindIII sites of pTK and the resulting construct was designated pTK5.

A second synthetic linker, F3R3, was made by annealing the forward primer F3R3F1 (SEQ ID NO:9) and the reverse primer F3R32 (SEQ ID NO:10). This linker was inserted between NotI and BamHI sites of pTK and the resulting construct was designated pTK53.

2. Insertion of the Luciferase Reporter Sequences LucR and LucY/G into pTK53

Schematic diagrams of the starting vector pKS and the intermediate constructs pTK and pTK53 are shown in FIG. 9.

The backbone vectors pTK-LucR and pTK-LucY/G were then constructed by introducing the luciferase reporter sequences LucR and LucY/G into pTK53.

Figure 10:
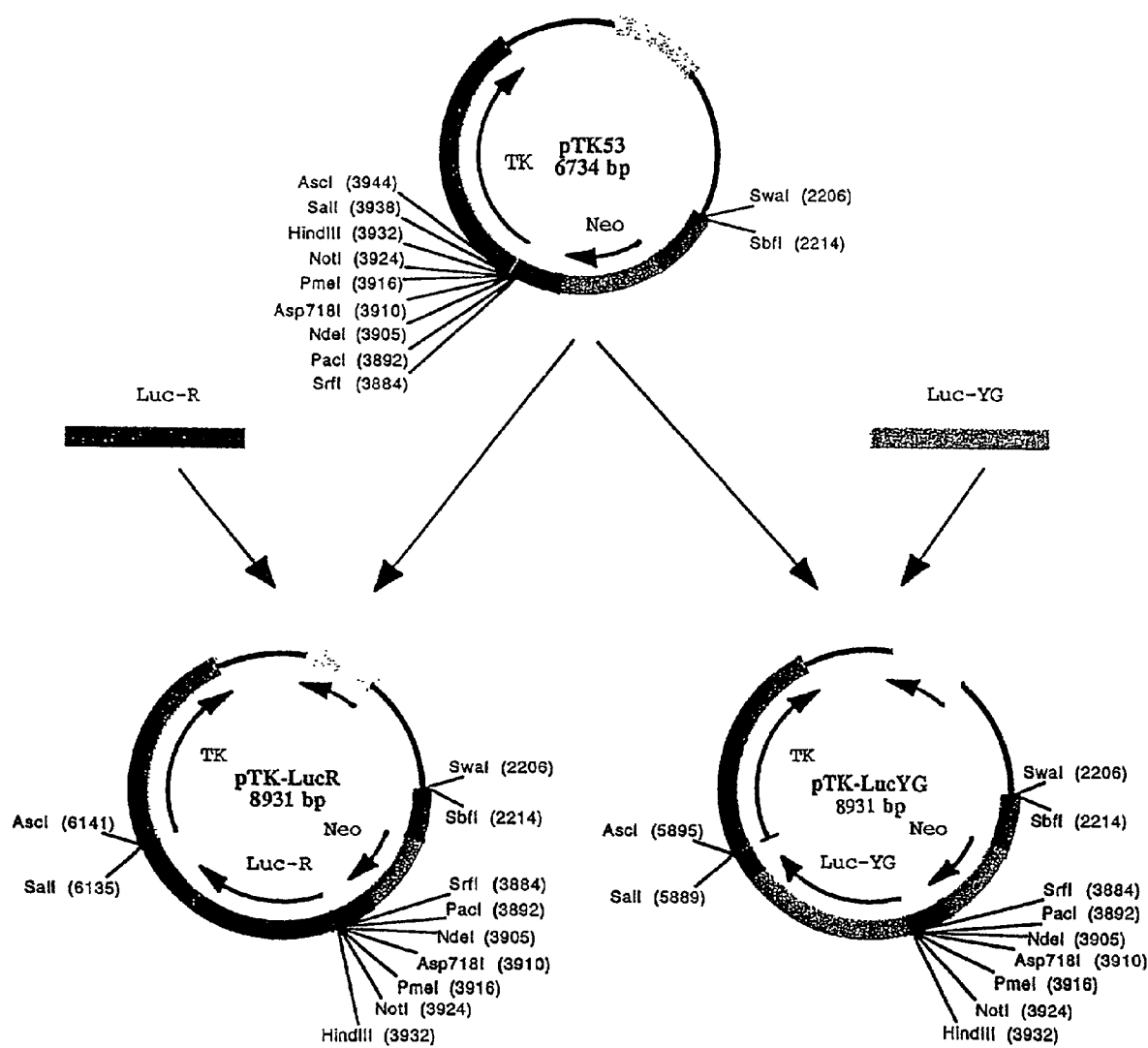
FIG. 10 is schematic depicting construction of the pTK-LucR and pTK-LucYG vectors. For pTK-LucR, a polynucleotide encoding LucR is introduced into pTK53. Thus, the pTK-LucR construct contains PGK-P, a neomycin (Neo$^r$) gene, a thymidine kinase (TK) gene and sequence encoding red luciferase (Luc-R). For pTK-LucYG, a polynucleotide encoding LucYG is introduced into pTK53. Thus, the pTK-LucYG construct contains PGK-P, a neomycin (Neo$^r$) gene, a thymidine kinase (TK) gene and a sequence encoding yellow-green luciferase (Luc-YG).

The yellow-green luciferase gene LucY/G was isolated from the vector pGL3B (Promega) and a HindIII-SalI fragment and was then cloned into pTK53 linearized with the same enzymes. A schematic diagram of the resulting backbone vector, designated pTK-LucYG (8931 bp), is shown in FIG. 10.

Similarly, the red luciferase gene LucR was isolated from the vector pGL3-red (obtained from Dr. Christopher Contag, Stanford University, Stanford, Calif.; Eames, B. F., et al., 1998, J. Invest. Med. 46 (1):94A) as a HindIII-SalI fragment and was then cloned into pTK53 linearized with the same enzymes. The resulting backbone vector, designated pTK-LucR (8931 bp), is also shown schematically in FIG. 10.

B. Insertion of Vitronectin and FosB Sequences

1. Insertion of Vitronectin Sequences into the pTK-LucYG and pTK-LucR Backbone Vectors to Produce the Intermediate Constructs pTKLG-Vn and pTKLR-Vn Vitronectin (Vn) is an abundant glycoprotein present in plasma and the extracellular matrix of most tissues. In a previous study, it was shown that heterozygous mice carrying one normal and one null VN allele and homozygous null mice completely deficient in vitronectin demonstrate normal development, fertility, and survival. These results suggest that VN is not essential for cell adhesion and migration during normal mouse development (Zheng, X., et al., Proc Natl Acad Sci USA 1995 92:12426–30). The sequence of the vitronectin gene is available in the GenBank database (Accession No. X72091; SEQ ID NO:42).

a. Insertion of the Vitronectin Sequence into the pTK-LucR Backbone Vector to Produce the Intermediate Construct pTKLR Vn The intermediate vector construct pTKLR-Vn was generated by inserting vitronectin (Vn) DNA sequences into the pTK-LucR vector constructed in Example 4A (see above).

A mouse vitronectin genomic DNA sequence of 5004 bp was obtained from the GenBank database (Accession No. X72091). The sequence served as the basis for designing the forward primer VN1F (SEQ ID NO:12) and the reverse primer VN1R (SEQ ID NO:11) which were used to PCR amplify a 1.63 kb 3' end vitronectin fragment using mouse C57BL/6 genomic DNA as a template (Genome Systems, Inc., St. Louis, Mo.). The fragment obtained was digested with SwaI and NsiI and cloned into pTK-LucR (linearized with SwaI and SbfI). This intermediate construct was designated as pTK-LucR3.

Figure 11:
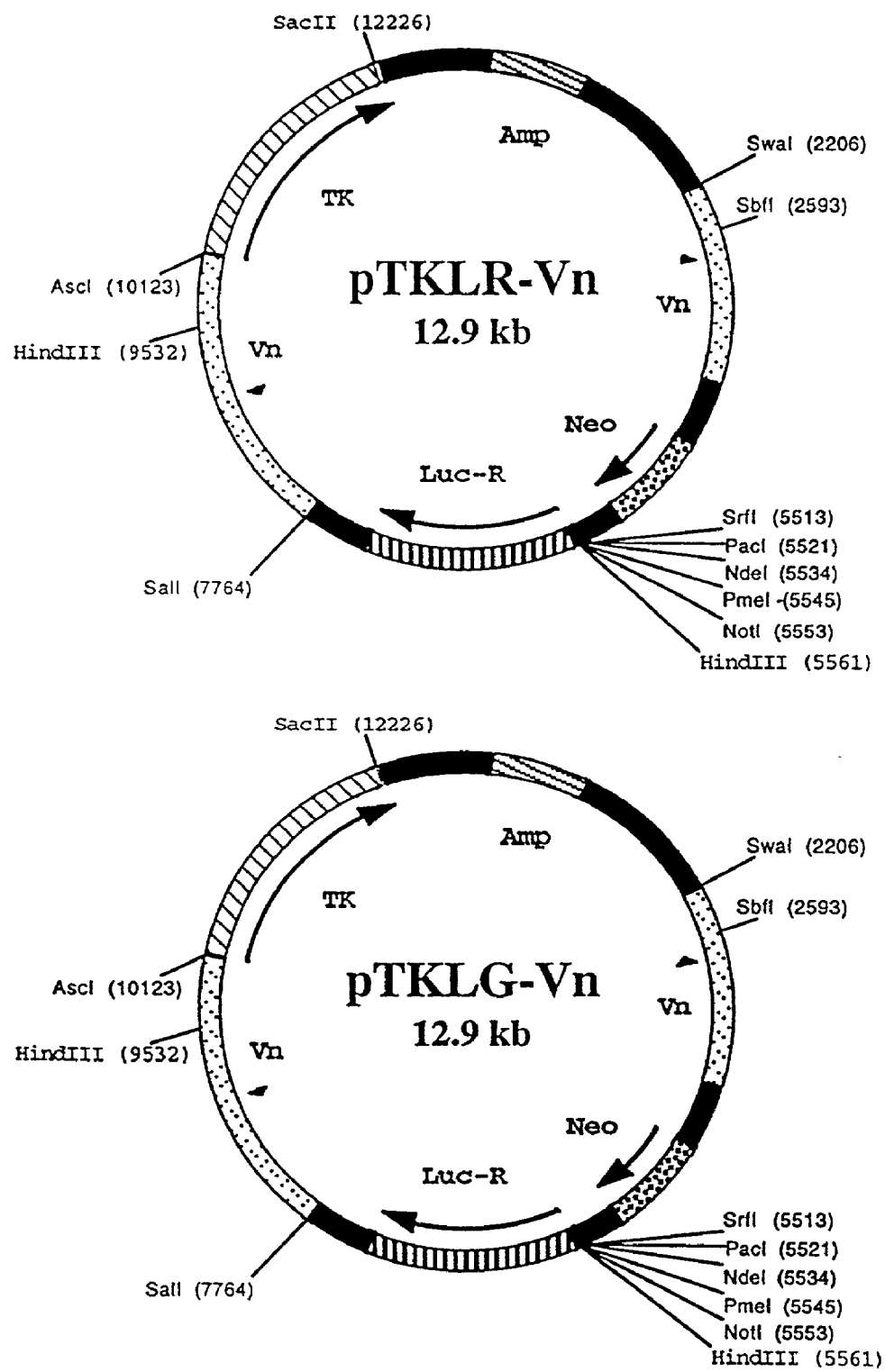
FIG. 11 is a schematic depicting the intermediate vector constructs pTKLR-Vn and pTKLG-Vn. Sequences homologous to the vitronectin gene are inserted into pTK-LucR and pTK-LucYG such that they flank the Neo$^r$ gene and the Luc-R coding sequence. The pTKLR-Vn construct contains PGK-P, a neomycin (Neo$^r$) gene, a thymidine kinase (TK) gene, a sequence encoding red luciferase (Luc-R), a 1.63 kb 3' end vitronectin gene fragment and a 2.35 kb 5' end vitronectin gene (see Example 4B(1)(a) below). The pTKLG-Vn is identical except that it contains a sequence encoding yellow-green luciferase (Luc-YG) in place of the sequence encoding red luciferase. See Example 4B(1)(b) below.

Subsequently, a 2.35 kb 5' end vitronectin fragment was PCR amplified from the same template DNA using the reverse primer VN2R (SEQ ID NO:13) and the forward primer VN2F (SEQ ID NO:14). This fragment was digested with SalI and AscI and cloned into pTK-LucR linearized with SalI and AscI. This construct was designated as pTKLR-Vn. FIG. 11 shows the restriction map of pTKLR-Vn.

The polylinker between the neomycin gene and the luciferase gene may be used to insert the VEGF promoter (see, e.g., Example 4C1 below) or other promoters or expression cassettes of interest.

b. Insertion of the Vitronectin Sequence into the pTK-LG Backbone Vector to Produce the Intermediate Construct pTKLG-Vn pTKLG-Vn was made by replacing the red luciferase gene (excised as a NotI-SalI fragment) in pTKLR-Vn with the yellow green luciferase gene (isolated as a NotI-SalI fragment) from pGL3B2 (see above). The restriction map of pTKLG-Vn is shown in FIG. 11.

The polylinker between the luciferase gene and the neomycin gene may be used to insert promoters or expression cassettes of interest.

2. Insertion of FosB Sequences into the pTK-LucYG Backbone Vector to Produce the Intermediate Construct pTKLG-Fos FosB is one of the members of the Fos family. It plays a functional role in transcriptional regulation. It has been shown that FosB mice are born at a normal frequency, are fertile and present no obvious phenotypic or histologic abnormalities (Gruda et al (1996) *Oncogene* 12:2177–2185).

A 28.8 kb genomic region that contains mouse FosB DNA was obtained from the GenBank database sequence (Accession No. AF093624). The sequence served as the basis for designing the PCR amplification primers FosB1F and FosB1R. The forward primer FosB1F (SEQ ID NO:15) and the reverse primer FosB1R (SEQ ID NO:16) were used to obtain a 1.71 kb 5' end FosB fragment using mouse C57BL/6 genomic DNA as a template. This fragment was digested with SwaI and SbfI and cloned into pTK-LucYG linearized with SwaI and SbfI. This construct was designated as pTK-LucYG3.

Figure 12:
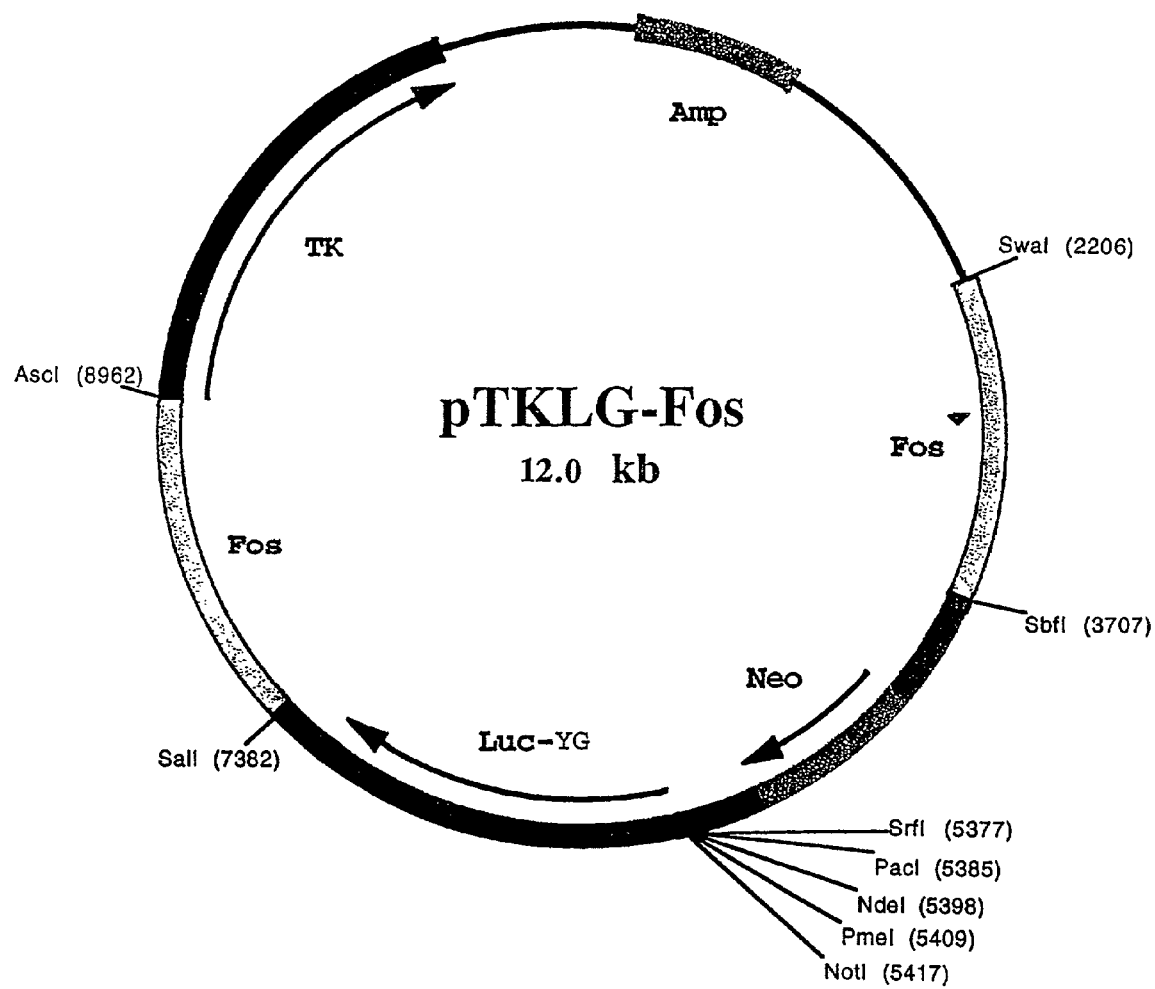
FIG. 12 is a schematic depicting the intermediate vector construct pTKLG-FosB. FosB gene sequences (SEQ ID NO:43) are inserted into pTK-LucYG such that they flank the Neo$^r$ gene and the Luc-YG coding sequence. See Example 4B(2) below.

Subsequently, a 1.58 kb 3' end FosB fragment was amplified from the same template DNA with the forward primer FosB2F (SEQ ID NO:17) and the reverse primer FosB2R (SEQ ID NO:18). This fragment was digested with SalI and AscI and cloned into pTK-LucYG linearized with SalI and AscI. The construct was designated as pTKLG-Fos, and is depicted in FIG. 12.

The polylinker between the luciferase gene and the neomycin gene may be used to insert promoters and expression cassettes of interest.

C. Insertion of Expression Cassettes

Figure 13:
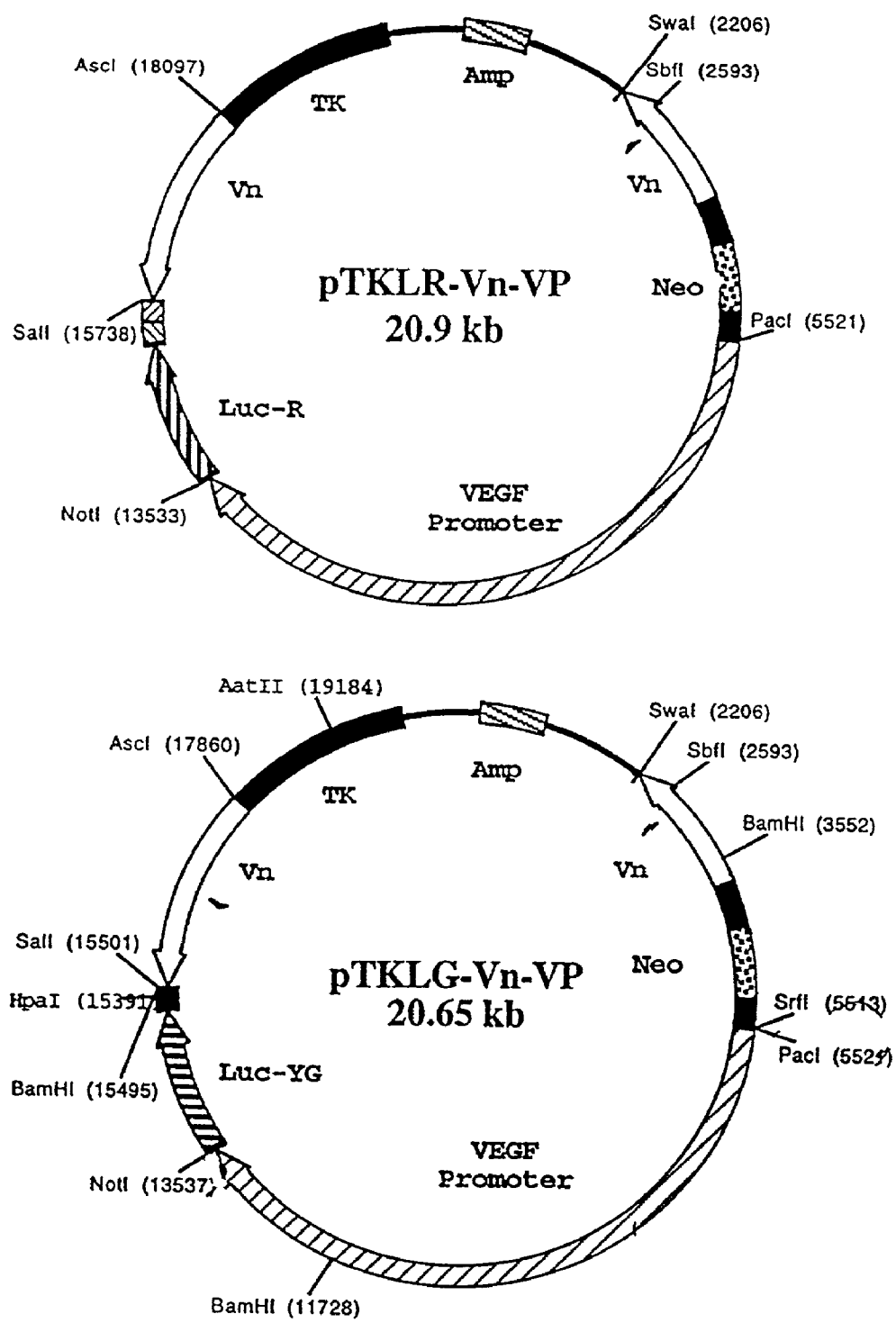
FIG. 13 is a schematic depicting the vectors pTKLR-Vn-VP and pTKLG-Vn-VP. A 7.8 kb VEGF promoter sequence (see Example 1) was cloned into the PacI and NotI sites in the polylinker regions of the pTKLR-Vn and pTKLG-Vn intermediate vector constructs, respectively. See Example 4C(1) below.

1. Introduction of the VEGF Promoter Sequence into the Intermediate Vector Constructs pTKLR-Vn and pTKLG-Vn to Create the Expression Cassette Vectors pTKLR-Vn-VP and pTKLG-Vn-VP pTKLR-Vn-VP and pTKLG-Vn-VP, depicted schematically in FIG. 13, were made by cloning the 7.8 kb PacI-NotI VEGF promoter fragment from pGL3B2-VP described above into the PacI and NotI sites in the polylinker regions of pTKLR-Vn and pTKLG-Vn, respectively.

2. Insertion of the VEGFR-2 Promoter-LucYG-VEGFR-2 Enhancer Cassette into the Intermediate Vector Constructs pTKLG-Vn and pTKLG-Fos to Create the Expression Cassette Vectors pTKLG-Vn-KPN and pTKLG-Fos-KPN The VEGFR-2 promoter-luciferase-enhancer cassette was isolated from pGL3B2-KPN as a PacI-SalI fragment and cloned into the same sites of pTKLG-Vn. The resulting construct was designated pTKLG-Vn-KPN. See FIG. 14.

Similarly, the VEGFR-2 promoter-luciferase-enhancer cassette was isolated from pGL3B2-KPN (see above) as a PacI-SalI fragment and cloned into the same sites of pTKLG-Fos. See FIG. 12. The resulting construct was designated pTKLG-Fos-KPN. See FIG. 14.

3. Insertion of the Tie2 Promoter-LucYG-Tie2 Enhancer Cassette into the Intermediate Vector Construct pTKLG-Fos to Create the Expression Cassette Vector pTKLG-Fos-TPN.

Figure 15:
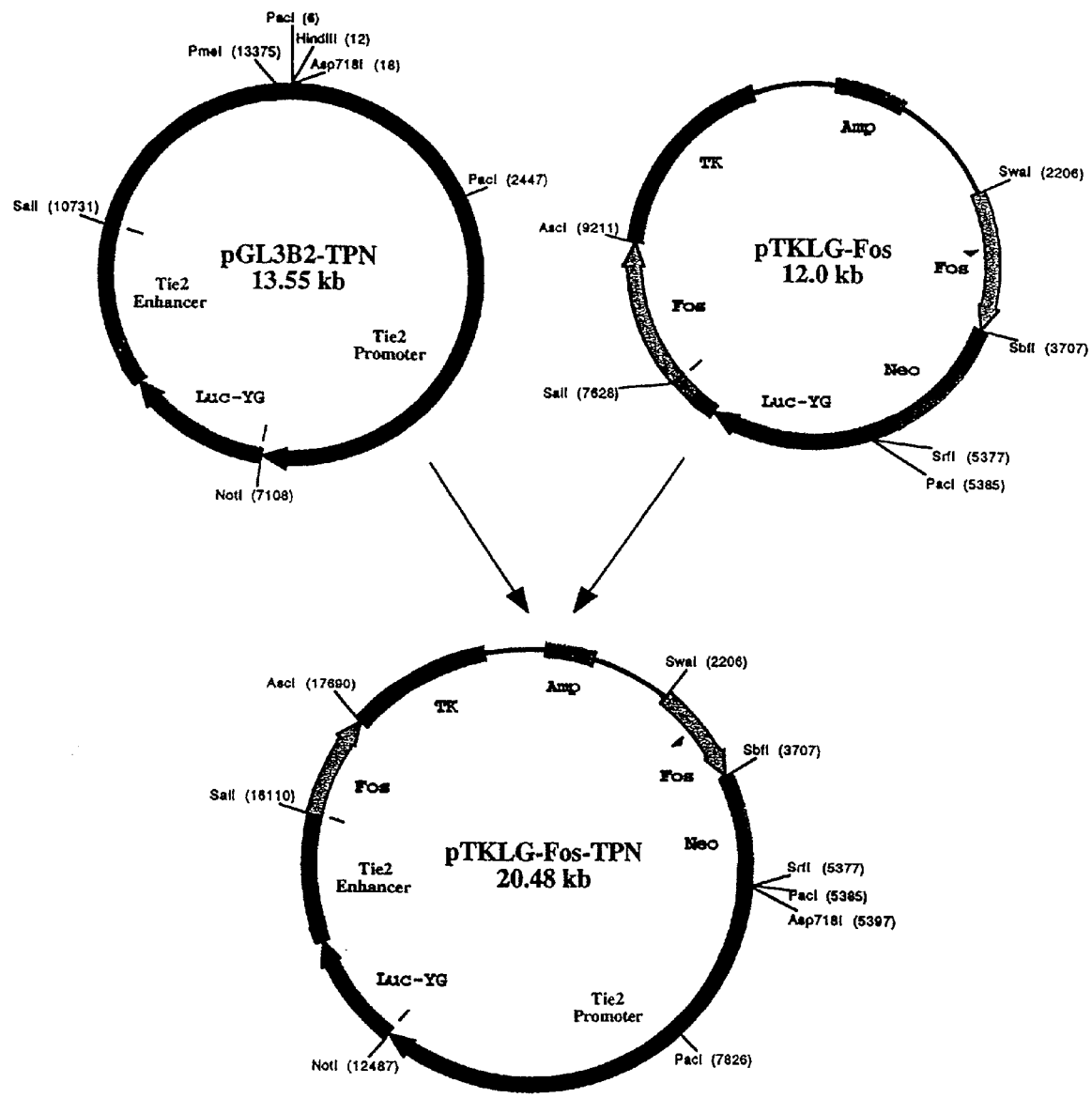
FIG. 15 is a schematic depicting engineering of the pTKLG-Fos-TPN construct using pGL3B2-TPN (FIG. 8) and pTKLG-Fos (FIG. 12). See Example 4C(3) below.

The Tie2 promoter-Luciferase-enhancer cassette was isolated from pGL3B2-TPN as a PacI-SalI fragment and cloned into the pTKLG-Fos vector linearized with PacI and SalI. The resulting construct was designated pTKLG-Fos-TPN. See FIG. 15.

Example 5

High Through-Put Screening of Putative Angiogenesis Modulating Compounds via the VEGFR-2 Promoter Sequence Putative angiogenesis-affecting compounds can be screened by monitoring their ability to modulate VEGFR-2 promoter-mediated bioluminescence in transfected cells. Vascular endothelial cells that are transfected with VEGFR2-Luc constructs, such as pGL3B2-KPN or pTKLG-Vn-KPN, are useful for high-through-put screening of compounds that can inhibit VEGFR2 promoter-mediated gene expression. This approach provides a means for discovering compounds capable of modulating angiogenesis and neoplasticity.

Briefly, transfected vascular endothelial cells prepared in the preceding example are plated into 96 well plates and used for high-through-put screening of a compound library. The compounds that reduce luciferase activity are selected for secondary screening. Upon confirmation by the secondary screening procedure, the candidate compounds are further tested in the VEGFR2-LucYG transgenic mouse models as described in Example 14 below.

As an example, the expression construct pGL3B2-KPN (see Example 2 above) was used to transiently transfect primary bovine endothelial cells (Clonetics) using lipofectamine (Promega). The cells were seeded onto 96-well plastic culturing plates (Nunc) prior to transfection. The transfection was carried out according to the manufacture's instructions (Promega). Plasmid pRL-TK (Promega), containing Renilla luciferase driven by the thymidine kinase promoter, was used as an internal control in all transfection experiments. The primary bovine endothelial cells were cultured in EGM-2 MV medium (Clonetics) at 37 C in 5% $CO_2$, 95% air. After transfection, the cells were lysed with passive lysis buffer (Promega) and assayed with the Dual-Luciferase Reporter Assay System (Promega) for luciferase activity.

Several angiogenesis and neoplasticity inhibitors (Sigma) were then tested for their effects on VEGFR-2 promoter-mediated luciferase expression in the transfected primary bovine endothelial cells described above. The tested compounds included the neoplasticity inhibitor mithramycin, and angiogenesis inhibitors 2-methoxyestradiol, thalidomide, and fumagillin.

Figure 16A:
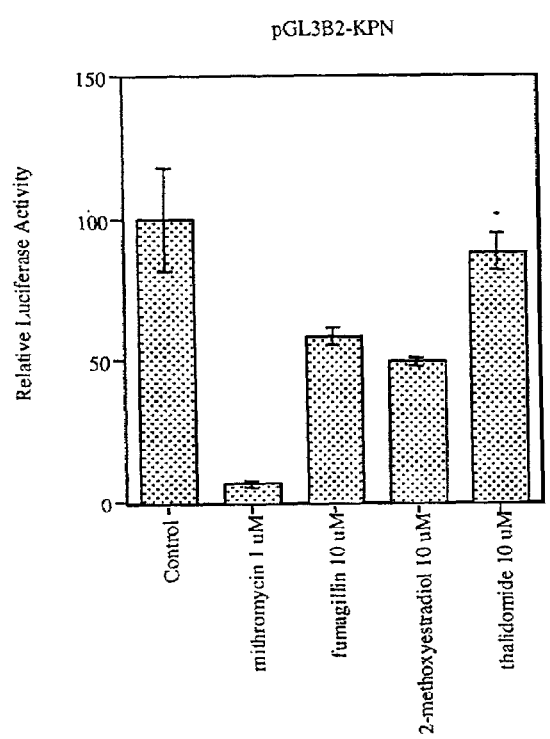
FIGS. 16A and 16B are graphical representations of transfection experiments performed to study the effect of neoplasticity and angiogenesis inhibitors on VEGFR2 (FIG. 16A) and Tie2 (FIG. 16B) promoter expression in endothelial cells. See Example 5 and Example 6 below.

Briefly, 24 hours after transfection with pGL3B2-KPN, the cells were treated with selected angiogenesis and neoplasticity inhibitors for 36 hours and assayed for luciferase activity. Cells treated with mithramycin (1 μM), fumagillin (10 μM) and 2-methoxyestradiol (10 μM) all showed significant decrease of luciferase activity, indicating that these compounds can inhibit VEGFR2 expression mediated by the 4.5 kb VEGFR-2 promoter. See FIG. 16A.

These results suggest that sequences derived from the 4.5 kb VEGFR-2 promoter are useful for high-through-put screening for compounds capable of modulating VEGFR-2-mediated angiogenesis.

Example 6

High Through-Put Screening of Putative Angiogenesis Modulating Compounds Via the Tie2 Promoter Sequence Putative angiogenesis-affecting compounds can be screened by monitoring their ability to modulate Tie-2 promoter-mediated bioluminescence in transfected cells. Vascular endothelial cells that are transfected with Tie2-Luc constructs (e.g., pGL3B2-TP) are useful for high-through-put screening of compounds that can inhibit Tie2 promoter-mediated gene expression. These approaches provide a means for discovering compounds capable of modulating angiogenesis and neoplasticity.

Briefly, transfected vascular endothelial cells prepared in the preceding example are plated into 96 well plates and used for high-through-put screening of a compound library. The compounds that reduce luciferase activity are selected for secondary screening.

As an example, the expression construct pGL3B2-TP prepared above (see Example 3B above) was used to transiently transfect primary bovine endothelial cells (Clonetics) using lipofectamine (Promega). The cells were seeded onto 96-well plastic culturing plates (Nunc) prior to transfection. The transfection was carried out according to the manufacture's instructions (Promega). Plasmid pRL-TK (Promega), containing Renilla luciferase driven by the thymidine kinase promoter, was used as an internal control in all transfection experiments. The primary bovine endothelial cells were cultured in EGM-2 MV medium (Clonetics) at 37 C in 5% $CO_2$, 95% air. After transfection, the cells were lysed with passive lysis buffer (Promega) and assayed with the Dual-Luciferase Reporter Assay System (Promega) for luciferase activity.

Several angiogenesis and neoplasticity inhibitors (Sigma) were then tested for their effects on the expression of Tie-2 expression in the transfected primary bovine endothelial cells described above.

Figure 16B:
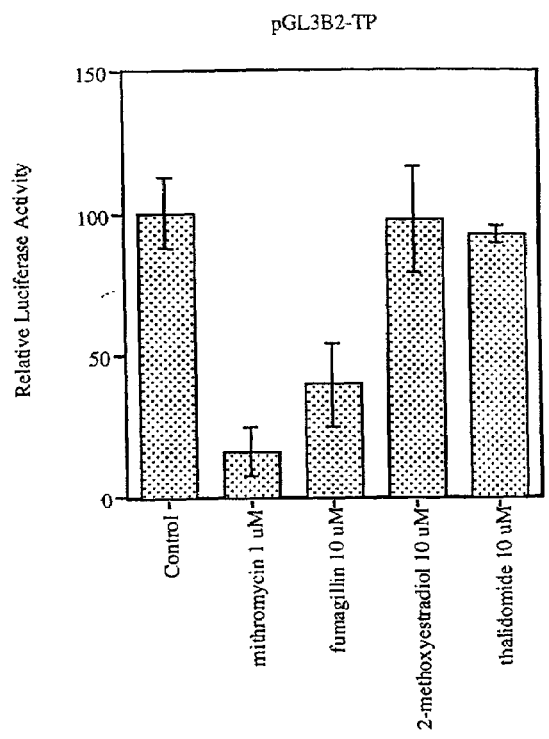
Figures 17A, 17B, 17C, 17D:
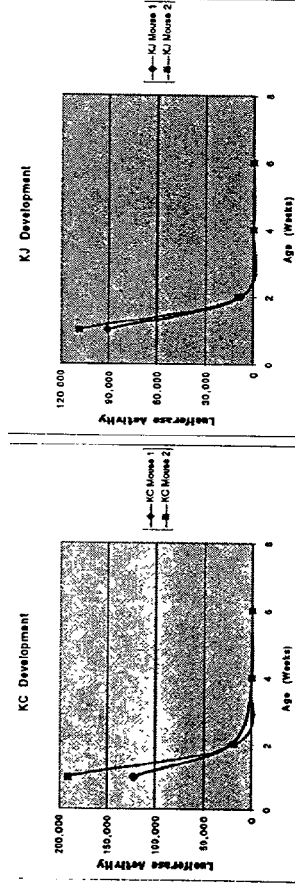
FIGS. 17A through 17D present graphical representation of the results of bioluminescent imaging of VEGFR-2 transgenic mice from four founders over the course of 1–6 week development period (FIG. 17A, transgenic KC.

Briefly, 24 hours after transfection with pGL3B2-TP, the cells were treated with selected angiogenesis and neoplasticity inhibitors for 36 hours and assayed for luciferase activity. The tested compounds included the neoplasticity and angiogenesis inhibitors mithramycin, 2-methoxyestradiol, thalidomide and fumagillin. Cells treated with mithramycin (1 μM) and fumagillin (10 μM) showed significant decrease of luciferase activity, indicating that these compounds can inhibit Tie2 expression mediated by the 7.1 kb Tie2 promoter. See FIG. 16B.

These results suggest that sequences derived from the 7.1 kb Tie2 promoter are useful for screening compounds that may be capable of modulating Tie2-mediated angiogenesis.

Example 7

In vivo Monitoring of VEGFR-2-Mediated Angiogenesis During Development

Four lines of transgenic mice carrying the VEGFR-2 promoter-LucYG-VEGFR-2 enhancer expression cassette were obtained using pGL3B2-KPN combined with known methods for generating transgenic mice (see the discussion above). These animals ("founders") were bred to non-transgenic mates to produce litters of from 8 to 10 pups ("F1 animals").

Two F1 animals from each of the four VEGFR2 founders (designated KA, KC, KG and KJ) were continuously imaged from the age of one to six weeks according to the methods described in U.S. Pat. No. 5,650,135 to Contag et al. All of the mice imaged exhibited rapid reduction in VEGFR-2-mediated expression of bioluminescence over the course of development. All mice showed high level of signal when imaged at the age of 1 week. The signal decreased dramatically in all the mice when they were imaged at the age of 2 weeks. Further decrease of the signal was observed when the mice were imaged at 4 weeks and the signals decreased to basal levels when the mice reached 6 weeks. The observed signal intensities were quantified. As shown in FIGS. 17A, 17B, 17C, and 17D, the KC, KJ, KG and KA individuals, respectively, showed 7,000-, 7,000-, 1300-, and 20–1000 fold reductions, respectively, in the luciferase signals observed during the monitored development period.

These experiments demonstrate that the expression cassettes and transgenic animals of the present invention may be used to monitor VEGFR-2 promoter-mediated expression of bioluminescence in vivo over the course of development.

Example 8

In vivo Monitoring of VEGFR-2-Mediated Angiogenesis During Estrus

Figure 18A:
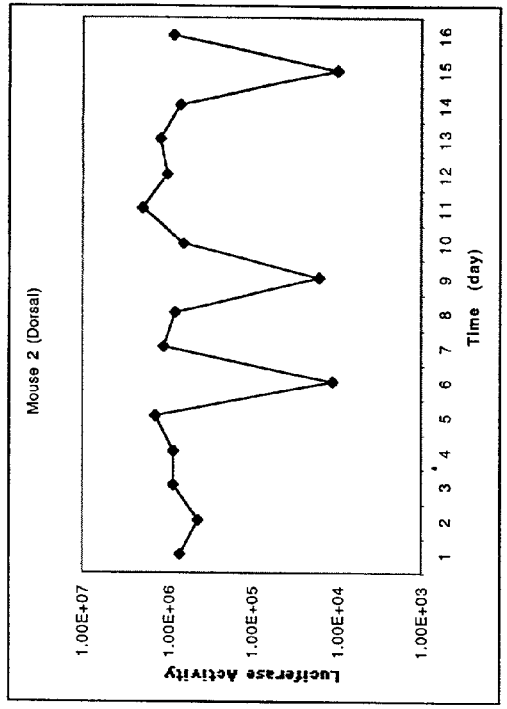
FIGS. 18A through 18D present graphical representation of the results of bioluminescent imaging of 2 female VEGFR-2 KA transgenic mice over the course of several estrus cycles (FIGS. 18A and 18B, mouse 1 and 2 dorsal views, respectively, and FIGS. 18C and 18D, mouse 1 and 2 ventral views, respectively). See Example 8 below.
Figure 18B:
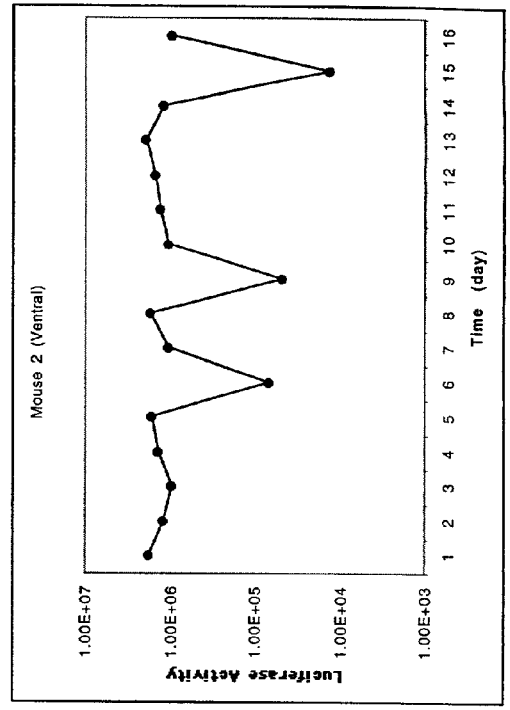
Figure 18C:
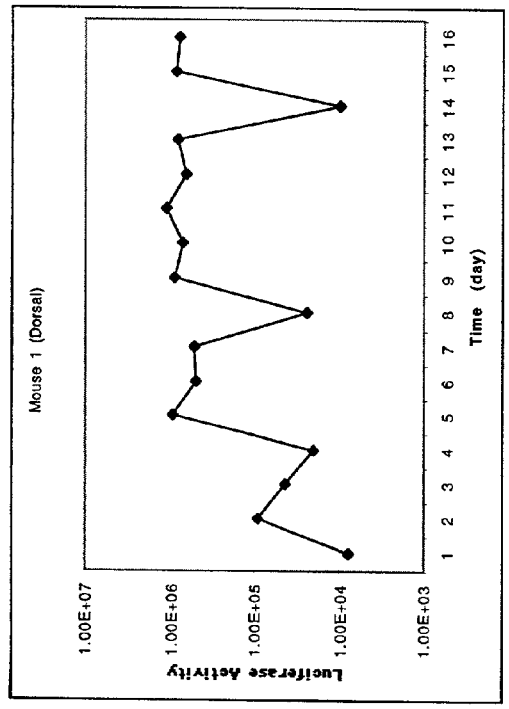
Figure 18D:
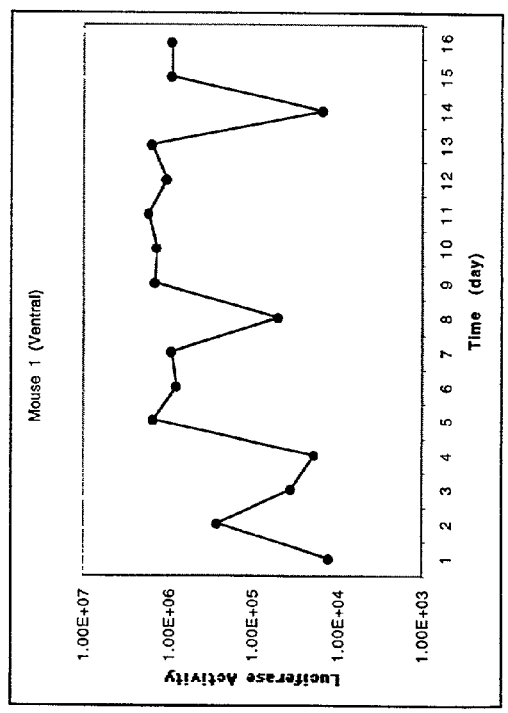

Two female VEGFR2 transgenic F1 mice from founder KA (See Example 7 above) were subjected to in vivo imaging of bioluminescence both dorsally and ventrally over a 16 day period according to the methods described in U.S. Pat. No. 5,650,135 to Contag et al. The results are presented graphically in FIGS. 18A–18D (FIGS. 18A and 18B, mouse 1 and 2 dorsal views, respectively, and FIGS. 18C and 18D, mouse 1 and 2 ventral views, respectively). Both mice exhibited cyclic variation in the levels of bioluminescence detected over periods of from 3 to 6 days. In general, higher levels of luminescence were detectable ventrally as compared to dorsally. The signals appeared to be localized in the ovary (dorsal view) and uterus (ventral view). Both ovaries were clearly visible in most of the dorsal views. The uterus, connecting tubes and ovaries were visible in some of the ventral views. Quantification of the signals showed more than a 100 fold difference in signal intensity over the course of the estrus cycle.

These results demonstrate that it is possible to monitor changes in VEGFR-2 promoter-mediated bioluminescence expression that occur during estrus in female mice carrying the VEGFR-2-Luc transgene cassette. They may be applied in a number of ways. For example, the transgenic mice may be used with the in vivo imaging protocol described to test the efficacy of estrogen antagonists (see the following example), to screen for endocrine disrupters, and to test the efficacy of compounds targeted to estrogen-dependent tumors.

Example 9

Examining the Effect of Endocrine Disrupters on VEGFR-2 Promoter-Mediated Angiogenesis During Estrus The effect of the known estrogen antagonist ICI 182 780 (Tocris Cookson Ltd. Bristol, UK) on gene expression mediated by the VEGFR-2 promoter was investigated using the methods described in the preceding example.

A mature female VEGFR2 transgenic F1 mouse from founder KA (See Example 7 above) was imaged daily for 16 days according to the methods described in U.S. Pat. No. 5,650,135 to Contag et al. The bioluminescence signal remained high for a maximum of from 3–5 days, dropping back to a basal level for the interim periods.

Figure 19C:
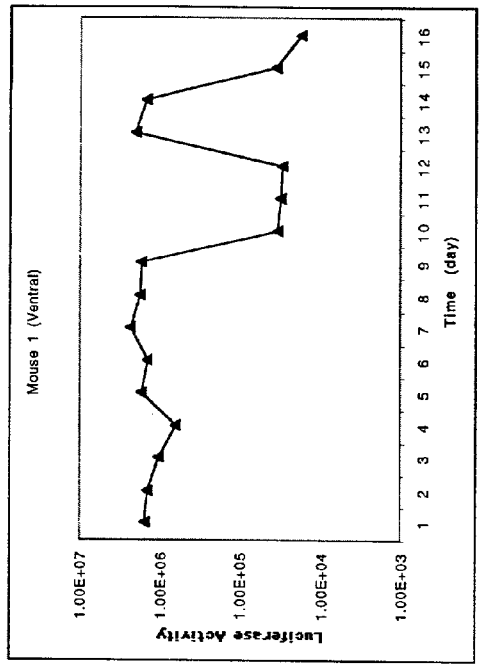
FIGS. 19A through 19D present graphical representation of the results of bioluminescent imaging of a female VEGFR-2 KA transgenic mouse treated with estrogen antagonist ICI 182 780 over the course of several estrus cycles (FIGS. 19A and 19B, dorsal and ventral views, respectively, before treatment.
Figure 19D:
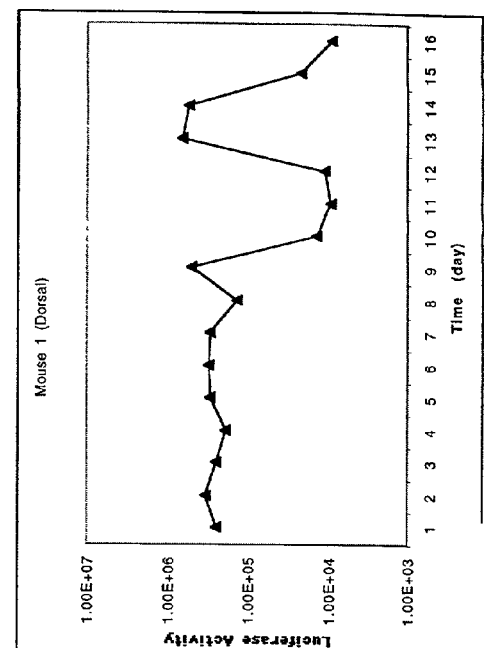
Figure 19A:
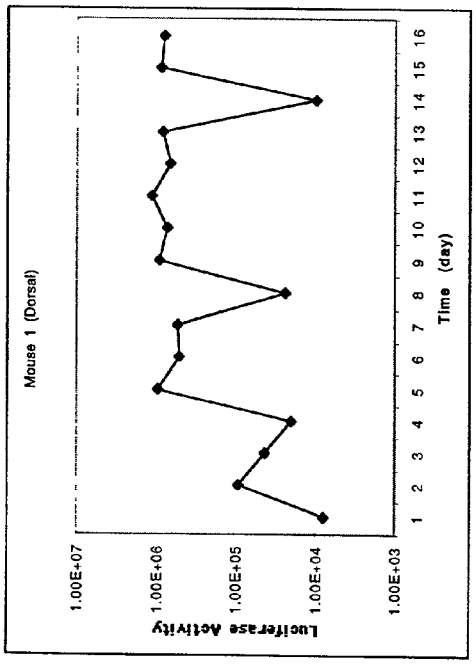
Figure 19B:
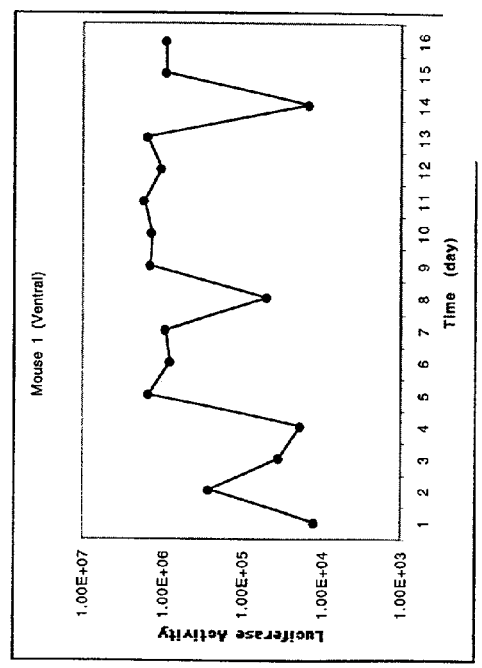

The same mouse was subsequently treated with ICI 182 780 by subcutaneous injection at a dosage of 30mg/kg/day for another 16 day period, and was imaged daily for the duration of the treatment. After an initial lag of several days following commencement of treatment, the uterine signal remained high for 9 days before dropping back to basal level. See FIGS. 19A–19D (FIGS. 19A and 19B, dorsal and ventral views, respectively, before treatment; FIGS. 19C and 19D, ventral and dorsal views, respectively, after treatment).

These results suggest that transgenic animals carrying the expression constructs of the present invention may be used to investigate the effects of endocrine disrupting compounds, including but not limited to estrogen antagonists such as ICI 182 789, on VEGFR-2-mediated gene expression during the estrus cycle.

Example 10

Examining the Effect of Growth Factors on VEGFR-2 Promoter-Mediated Angiogenesis The effect of the growth factors on gene expression mediated by the VEGFR-2 promoter was investigated.

Transgenic mice carrying the VEGFR-2 promoter-LucYG-VEGFR-2 enhancer expression cassette were obtained using pGL3B2-KPN by known methods for generating transgenic mice (see the discussion above). These founder animals were bred to non-transgenic mates to produce litters of from 8 to 10 F1 animals.

Figure 20:
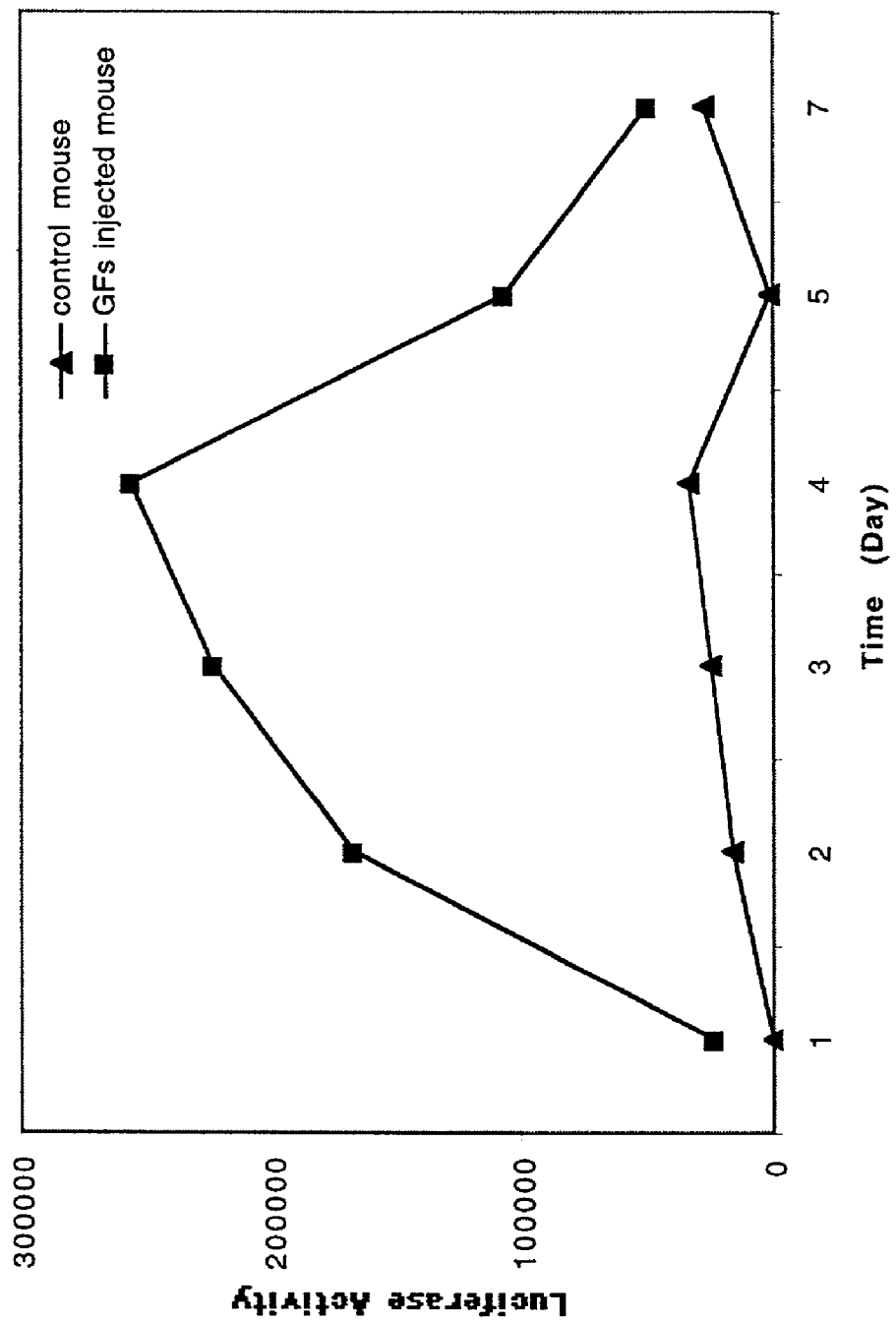
FIG. 20 is a graphical representation of the results of bioluminescent imaging of a VEGFR-2 transgenic mouse (founder KC) implanted with growth factor-containing matrigel and a control mouse. See Example 10 below.

A mature F1 mouse carrying the VEGFR-2 promoter-LucYG-VEGFR-2 enhancer expression cassette was injected into the center of the abdominal midline with 500 µl of matrigel containing a growth factor cocktail (2 fig VEGF, 0.5 µg bFGF, 0.5 µg aFGF). A control F1 mouse carrying the VEGFR-2 promoter-LucYG-VEGFR-2 enhancer expression cassette was injected with matrigel alone. Both mice were imaged for 7 days after the matrigel injection. In the mouse that were injected with the growth factor containing matrigel, an induction of VEGFR2 mediated luciferase signal was detected 1 day after the matrigel injection. This signal went up at day 2 and reached a peak at day 4. By day 7, the signal dropped back to the basal level. This growth factor-mediated luciferase induction was absent in the mouse that was injected with matrigel alone. See FIG. 20.

This experiment demonstrates that transgenic animals carrying the expression constructs of the present invention may be used to investigate the effects of growth factors on VEGFR-2 gene expression during the angiogenesis process.

Example 11

Monitoring of VEGF Promoter-Mediated Bioluminescence in C57BL/6J-Tyr$^{c-2J/+}$ Mice During Tumor Development Using Tumor Cell Lines Stably Transfected with pTKLG-Vn-VP The pTKLG-Vn-VP vector construct described in Example 4 above was used to stably transfect several tumor cell lines including LL/2 (Lewis lung carcinoma), B 16-F1 (mouse melanoma) and T241 (mouse fibrosarcoma) to generate tumor cell lines expressing VEGF-mediated bioluminescence. The transfection was accomplished using lipofectamine as described in the manufacturer's instructions (Promega).

All tumor cells were cultured in DMEM medium plus 10% fetal bovine serum (Gibco BRL) at 37° C. in 5% $CO_2$ and 95% air. After transfection, cells were selected with G418 (Gibco BRL) in a concentration range of 600–800 µg/ml. After 2–3 weeks of selection, stable clones were recovered and tested for luciferase expression.

Figure 21:
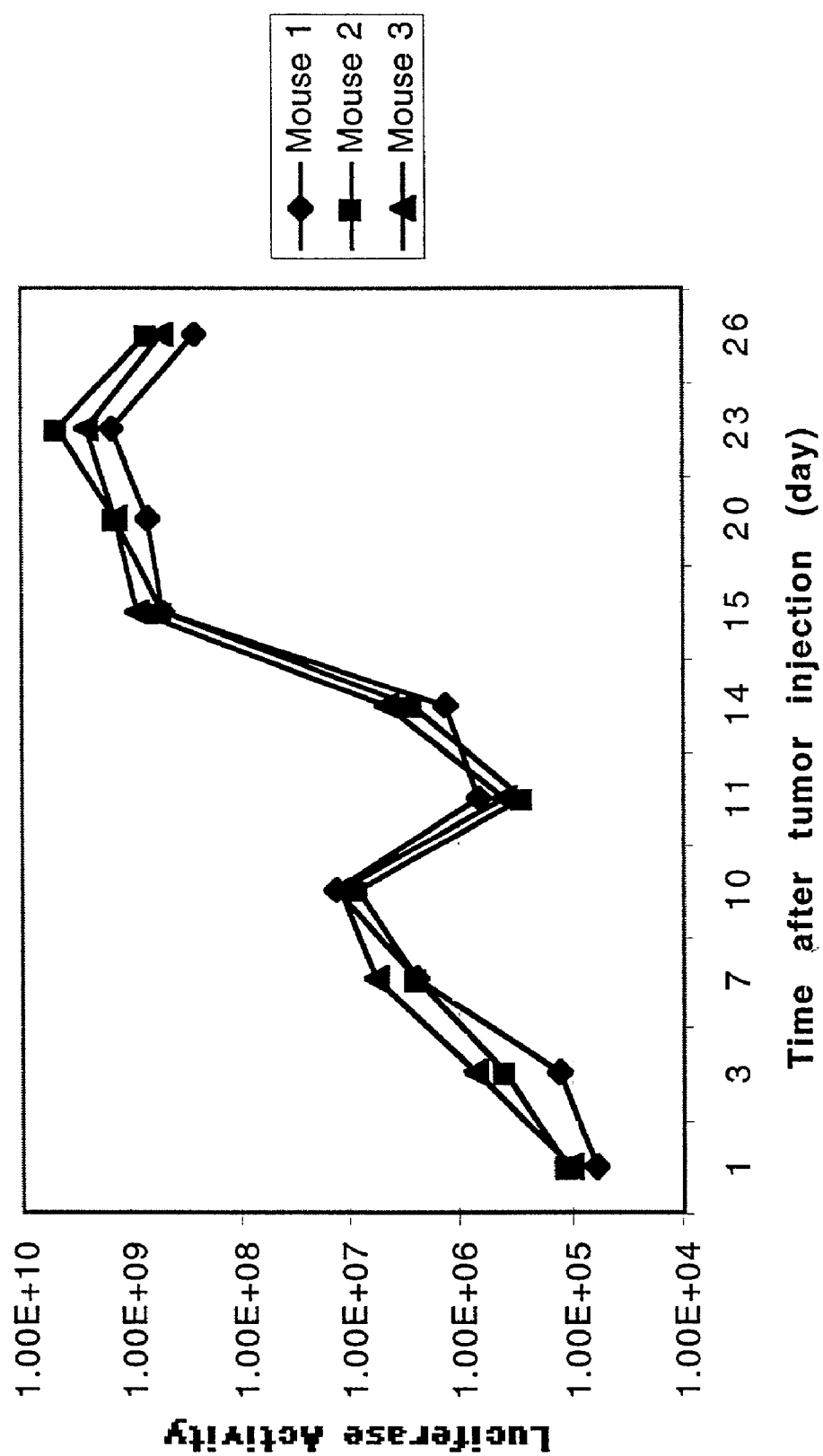
FIG. 21 is a graphical representation of the results of bioluminescent imaging of C57BL/6J-Tyr$^{c-2J/+}$ mice implanted with LL/w cells stably transfected with the VEGF-Luc construct pTKLG-Vn-VP. See Example 11 below.

A luciferase-expressing LL/2 clone was selected, and $1 \times 10^6$ cells from this clone were injected into C57BL/6J-Tyr$^{c-2J/+}$ mice and monitored for luciferase activity for a period of 26 days. In three separate injection sites (FIG. 21, Mouse 1, solid diamonds; Mouse 2, solid squares; and Mouse 3, solid triangles), luciferase activities were detected 1 day after the injection. The signal reached a peak at day 10, followed by a decrease of the signal at day 11. The signal went up again from day 14 and reached a second peak at day 23. By day 26, the signal started to drop again and the mice died a few days after the last image. See FIG. 21.

This experiment demonstrates that stable tumor cells generated with the VEGF expression vector pTKLG-Vn-VP of the present invention can be used to investigate VEGF gene expression during tumor development.

Example 12

High Through-Put Screening of Putative Angiogenesis and Neoplasticity-Modulating Compounds Via the VEGF Promoter Sequence

The tumor cells stably transfected with pTKLG-Vn-VP that were generated in the preceding example are useful for high-through-put screening of compounds that can inhibit VEGF promoter-mediated gene expression. This approach provides a means for discovering compounds capable of modulating angiogenesis and neoplasticity.

Briefly, the stably transfected tumor cells or transfected vascular endothelial cells prepared in the preceding example are plated into 96 well plates and used for primary screening of a compound library. The compounds that reduce luciferase activity are selected for secondary screening. Upon confirmation by the secondary screening, the candidate compounds are further tested in the VEGF-Luc transgenic mice model or mice carrying VEGF-luc stable tumor cells, as described in Example 13 below.

Example 13

In vivo Monitoring of the Effects of Angiogenesis-Affecting Compounds on Tumor-Induced Angiogensis Mediated by VEGF

The effects of anti-angiogenesis compounds on tumor-induced VEGF expression may be tested in mice carrying the VEGF promoter expression cassettes of the present invention.

Transgenic mice carrying the VEGF promoter expression cassette are obtained by direct injection of the DNA into nuclei of zygotes derived from FVB mice. The FVB/VEGF transgenic mice are then bred with C57BL/6J-Tyr$^{c-2J/+}$ mice to generate hybrid transgenic mice. The hybrid transgenic animals carry the VEGF-Luc transgene and also allow the growth of C57BL/6-derived tumor cells. C57BL/6-derived tumor cells, including but not limited to B16F1 (melanoma), LL/2 (Lewis Lung carcinoma), and T241 (mouse fibrosarcoma) cells are then introduced into the hybrid transgenic mice.

The effects of a variety of putative anti-tumorigenic anti-angiogenic agents, including SU5416, PD173034, TNP-470, 2-methoxyestradiol, paclitaxel and PTK787, are then tested by administering 2 doses per compound to each of 3 tumor-carrying hybrid VEGF transgenic mice. The mice are imaged according to the methods described in U.S. Pat. No. 5,650,135 to Contag et al., and the results compared with those obtained for untreated controls.

Alternatively, non-transgenic mice, such as C57BL/6J-Tyr$^{c-2J/+}$ mice, can be implanted with tumor cells that have been stably transfected with the VEGF-Luc construct pTKLG-Vn-VP, including but not limited to, stably transfected B16F1 (melanoma) LL/2 (Lewis Lung carcinoma) and T241 (mouse fibrosarcoma) cells. The effects of the putative anti-tumorigenic anti-angiogenic agents listed above on VEGF expression are then tested by administering 2 doses per compound to each of 3 tumor-carrying mice. The mice are imaged according to the methods described in U.S. Pat. No. 5,650,135 to Contag et al., and the results are compared with those obtained for untreated controls.

Example 14

In vivo Monitoring of the Effects of Angiogenesis-Modulating Compounds on Tumor Induced Angiogenesis Mediated by VEGFR-2

The effects of anti-angiogenesis compounds on VEGFR-2 expression induced by implanted growth factor-containing matrigel and by implanted tumor cells may be tested in mice carrying the VEGFR-2 promoter expression cassettes of the present invention.

Transgenic mice carrying the VEGFR2 promoter expression cassette are obtained by direct injection of the DNA into nuclei of zygote derived from FVB mice. The FVB/VEGFR2 transgenic mice are then bred with C577BL/6J-Tyr$^{c-2J/+}$ mice to generate hybrid mice that carry the VEGFR2-luc transgene and that allow the growth of C57BL/6 derived tumor cells. C57BL/6 derived tumor cells, including but not limited to B16F1 (melanoma) LL/2 (Lewis Lung carcinoma) and T241 (mouse fibrosarcoma) cells, are then introduced into the transgenic mice as discussed in Example 10 above.

The effects of a variety of putative anti-tumorigenic anti-angiogenic agents, including SU5416, PD173034, TNP-470, 2-methoxyestradiol, paclitaxel and PTK787, are then tested by administering 2 doses per compound to each of 3 tumor-carrying hybrid VEGFR2 transgenic mice. The mice are imaged according to the methods described in U.S. Pat. No. 5,650,135 to Contag et al., and the results compared with those obtained for untreated controls.

Alternatively, FVB/VEGFR2 transgenic mice, are implanted with growth factor-containing matrigel as discussed in Example 10. The effects of the putative anti-tumorigenic anti-angiogenic agents listed above on VEGFR2 expression during growth factor-induced angiogenesis process are then tested by administering 2 doses per compound to the matrigel-carrying mice. The mice are imaged according to the methods described in U.S. Pat. No. 5,650,135 to Contag et al., and the results are compared with those obtained for untreated controls.

As is apparent to one of skill in the art, various modification and variations of the above embodiments can be made without departing from the spirit and scope of this invention. These modifications and variations are within the scope of this invention.

What is claimed is:

1. An isolated polynucleotide comprising either nucleotides 1 through 3,762 of SEQ ID NO:44 or a nucleic acid sequence that is at least 95% identical to the nucleotide sequence 1 through 3,762 of SEQ ID NO:44, wherein said isolated polynucleotide controls transcription of a gene operably linked thereto.

2. An isolated polynucleotide consisting of either SEQ ID NO:44 or a nucleic acid sequence that is at least 95% identical to the sequence of SEQ ID NO:44, wherein said isolated polynucleotide controls transcription of a gene operably linked thereto.

3. An expression cassette comprising:
   (a) the isolated polynucleotide of claim 1 comprising a transcription control element; and
   (b) a reporter sequence, operably linked to said transcription control element.

4. The expression cassette of claim 3, wherein said reporter sequence encodes a light-generating protein.

5. An expression cassette comprising:
   (a) the isolated polynucleotide of claim 2 comprising a transcription control element; and
   (b) a reporter sequence, operably linked to said transcription control element.

6. The expression cassette of claim 5, wherein said reporter sequence encodes a light-generating protein.

7. A vector comprising
   (a) the isolated polynucleotide of claim 1 comprising a transcription control element;
   (b) a reporter sequence, operably linked to said transcription control element; and
   (c) a vector backbone.

8. The vector of claim 7, wherein said reporter sequence encodes a light-generating protein.

9. The vector of claim 7, wherein said vector backbone comprises an origin of replication.

10. The vector of claim 7, wherein said vector is a shuttle vector.

11. The vector of claim 7, wherein said vector backbone further comprises a selectable marker.

12. An isolated cell comprising the expression cassette of claim 3.

* * * * *